(12) United States Patent
Clube

(10) Patent No.: US 11,891,629 B2
(45) Date of Patent: Feb. 6, 2024

(54) PROPAGATOR CELLS AND METHODS FOR PROPAGATING PHAGE, IN PARTICULAR FOR DELIVERING CRISPR-CAS COMPONENTS VIA PROBIOTIC ORGANISMS

(71) Applicant: SNIPR Technologies Limited, Peterborough (GB)

(72) Inventor: Jasper Clube, London (GB)

(73) Assignee: SNIPR TECHNOLOGIES LIMITED, Peterborough (GB)

(*) Notice: Subject to any disclaimer, the term of this patent is extended or adjusted under 35 U.S.C. 154(b) by 655 days.

(21) Appl. No.: 16/637,656

(22) PCT Filed: Aug. 8, 2018

(86) PCT No.: PCT/EP2018/071454
§ 371 (c)(1),
(2) Date: Feb. 7, 2020

(87) PCT Pub. No.: WO2019/030257
PCT Pub. Date: Feb. 14, 2019

(65) Prior Publication Data
US 2021/0230559 A1 Jul. 29, 2021

(30) Foreign Application Priority Data
Aug. 8, 2017 (GB) .................... 1712733

(51) Int. Cl.
*C12N 7/00* (2006.01)
*A61K 35/74* (2015.01)

(52) U.S. Cl.
CPC ............... *C12N 7/00* (2013.01); *A61K 35/74* (2013.01); *C12N 2310/20* (2017.05); *C12N 2795/00023* (2013.01); *C12N 2795/00032* (2013.01); *C12N 2795/00052* (2013.01); *C12N 2800/80* (2013.01)

(58) Field of Classification Search
CPC .................................................. C12N 2310/20
See application file for complete search history.

(56) References Cited

U.S. PATENT DOCUMENTS

| 9,701,964 | B2 | 7/2017 | Clube |
|---|---|---|---|
| 10,195,273 | B2 | 2/2019 | Clube |
| 10,300,138 | B2 | 5/2019 | Clube |
| 10,300,139 | B2 | 5/2019 | Clube |
| 10,363,308 | B2 | 7/2019 | Clube |
| 10,463,049 | B2 | 11/2019 | Clube |
| 10,506,812 | B2 | 12/2019 | Clube |
| 10,524,477 | B2 | 1/2020 | Clube |
| 10,561,148 | B2 | 2/2020 | Clube |
| 10,582,712 | B2 | 3/2020 | Clube |
| 10,596,255 | B2 | 3/2020 | Clube |
| 10,603,379 | B2 | 3/2020 | Clube |
| 10,624,329 | B2 | 4/2020 | Broughton et al. |
| 2001/0026795 | A1 | 10/2001 | Merril |
| 2002/0001590 | A1 | 1/2002 | Kelly |
| 2002/0044922 | A1 | 4/2002 | Mardh |
| 2002/0058027 | A1 | 5/2002 | Nelson |
| 2005/0118719 | A1 | 6/2005 | Schmidt |
| 2011/0136688 | A1 | 6/2011 | Scholl |
| 2015/0140001 | A1 | 5/2015 | Lee |
| 2016/0160186 | A1 | 6/2016 | Parsley |
| 2016/0333348 | A1 | 11/2016 | Clube |
| 2017/0196225 | A1 | 7/2017 | Clube |
| 2017/0246221 | A1 | 8/2017 | Clube |
| 2018/0064114 | A1 | 3/2018 | Clube |
| 2018/0064115 | A1 | 3/2018 | Clube |
| 2018/0070594 | A1 | 3/2018 | Clube |
| 2018/0084785 | A1 | 3/2018 | Clube |
| 2018/0084786 | A1 | 3/2018 | Clube |
| 2018/0140698 | A1 | 5/2018 | Clube |
| 2018/0146681 | A1 | 5/2018 | Clube |
| 2018/0273940 | A1 | 9/2018 | Sommer |
| 2018/0303934 | A1 | 10/2018 | Clube |
| 2018/0326057 | A1 | 11/2018 | Clube |
| 2018/0326093 | A1 | 11/2018 | Clube |
| 2019/0133135 | A1 | 5/2019 | Clube |
| 2019/0134194 | A1 | 5/2019 | Clube |
| 2019/0160120 | A1 | 5/2019 | Haaber |
| 2019/0230936 | A1 | 8/2019 | Clube |
| 2019/0240325 | A1 | 8/2019 | Clube |
| 2019/0240326 | A1 | 8/2019 | Clube |
| 2019/0321468 | A1 | 10/2019 | Clube et al. |
| 2019/0321469 | A1 | 10/2019 | Clube et al. |
| 2019/0321470 | A1 | 10/2019 | Clube |
| 2020/0030444 | A1 | 1/2020 | Clube |
| 2020/0068901 | A1 | 3/2020 | Clube |
| 2020/0077663 | A1 | 3/2020 | Clube |
| 2020/0087660 | A1 | 3/2020 | Sommer |
| 2020/0102551 | A1 | 4/2020 | Barrangou |
| 2020/0115716 | A1 | 4/2020 | Martinez |
| 2020/0121787 | A1 | 4/2020 | Clube |
| 2020/0128832 | A1 | 4/2020 | Clube |
| 2020/0164070 | A1 | 5/2020 | Clube |
| 2020/0205416 | A1 | 7/2020 | Clube |
| 2020/0254035 | A1 | 8/2020 | Haaber |
| 2020/0267992 | A1 | 8/2020 | Clube |
| 2020/0337313 | A1 | 10/2020 | Clube |
| 2021/0147827 | A1 | 5/2021 | Clube |

FOREIGN PATENT DOCUMENTS

| EP | 3132035 | B8 | 4/2020 |
|---|---|---|---|
| EP | 3633032 | A2 | 4/2020 |
| EP | 3634442 | A1 | 4/2020 |
| EP | 3634473 | A1 | 4/2020 |
| WO | 200069269 | A1 | 11/2000 |

(Continued)

OTHER PUBLICATIONS

Braun et al., Chapter 1 Bacterial Cell Surface Receptors, 1981; Organization of Prokaryotic Cell Membranes pp. 1-73 (Year: 1981).*

(Continued)

*Primary Examiner* — Brian Gangle
*Assistant Examiner* — Lakia J Jackson-Tongue
(74) *Attorney, Agent, or Firm* — MORRISON & FOERSTER LLP

(57) ABSTRACT

The invention provides propagator cells and methods for propagating phage and transduction particles.

21 Claims, 1 Drawing Sheet

(56) References Cited

FOREIGN PATENT DOCUMENTS

| WO | 200193904 A1 | 12/2001 |
|---|---|---|
| WO | 200207742 A2 | 1/2002 |
| WO | 200207742 A3 | 8/2002 |
| WO | 2014124226 A1 | 8/2014 |
| WO | 2015159086 A1 | 10/2015 |
| WO | 2015159087 A1 | 10/2015 |
| WO | 2016177682 A1 | 11/2016 |
| WO | 2016205276 A1 | 12/2016 |
| WO | WO 2016/205276 A1 * | 12/2016 |
| WO | 2017112620 A1 | 6/2017 |
| WO | 2018217351 A1 | 11/2018 |
| WO | 2018217981 A1 | 11/2018 |
| WO | 2018226853 A1 | 12/2018 |
| WO | 2020072248 A1 | 4/2020 |
| WO | 2020072250 A1 | 4/2020 |
| WO | 2020072253 A1 | 4/2020 |
| WO | 2020072254 A1 | 4/2020 |

OTHER PUBLICATIONS

Ainsworth, S. et al. (May/Jun. 2014). "Differences in Lactococcal Cell Wall Polysaccharide Structure Are Major Determining Factors in Bacteriophage Sensitivity," mBio 5(3):e00880-14, 11 pages.

Bae, H.-W. et al. (2013). "Complete Genome Sequence of Pseudomonas aeruginosa Podophage MPK7, Which Requires Type IV Pili for Infection," Genome Announce 1(5):e00744-13, 1 page.

Baptista, C. et al. (Jul. 2008, e-pub. May 16, 2008). "C Phage SPP1 Reversible Adsorption to Bacillus Subtilis Cell Wall Teichoic Acids Accelerates Virus Recognition of Membrane Receptor Yueb," J Bacteriol 190(14):4989-4996.

Bebeacua, C. et al. (Nov. 2013). "Structure, Adsorption to Host, and Infection Mechanism of Virulent Lactococcal Phage p2," J Virol 87(22):12302-12312.

Beveridge, T.J. et al. (Dec. 1991). "Surface Layers of Bacteria," Microbiol Rev 55(4):684-705.

Black, P.N. (Jun. 1988). "The fadL Gene Product of *Escherichia coli* Is an Outer Membrane Protein Required for Uptake of Long-Chain Fatty Acids and Involved in Sensitivity to Bacteriophage T2," J Bacteriol 170(6):2850-2854.

Bradbeer, C. et al. (1976), "Transport of Vitamin B12 in *Escherichia coli*: Common Receptor System for Vitamin 312 and Bacteriophage BF23 on the Outer Membrane of the Cell Envelope," J Bacteriol 125(3):1032-1039.

Braun, V. et al. (Aug. 1973). "Characterization of the Receptor Protein for Phage T5 and Colicin M in the Outer Membrane of *E. coli* B," FEBS Lett 34(1):77-80.

Braun, V. et al. (Sep. 27, 1973). "A Common Receptor Protein for Phage T5 and Colicin M in the Outer Membrane of *Escherichia coli* B," Biochim Biophys Acta 323(1):87-97.

Budzik, J.M. et al. (May 2004). "Isolation and Characterization of a Generalized Transducing Phage for Pseudomonas Aeruginosa Strains Pao1 and PA14," J Bacteriol 186(10):3270-3273.

Casjens, S.R. et al. (Feb. 2005). The Generalized Transducing *Salmonella bacteriophage* ES18: Complete Genome Sequence and DNA Packing Strategy, J. Bacteriology 187(3):1091-1104.

Chapot-Chartier, M.-P. et al. (Apr. 2, 2010). "Cell Surface of Lactococcus lactis Is Covered by a Protective Polysaccharide Pellicle," J Biol Chem 285(14):10464-10471.

Chatterjee, S. et al. (Nov. 15, 2012). "Interaction of Bacteriophage λ With Its *E. coli* Receptor LamB," Viruses 4:3162-3178.

Chaturongakul, S. et al. (Aug. 20, 2014). "Phage-Host Interplay: Examples From Tailed Phages and Gram-Negative Bacterial Pathogens," Front Microbiol 5(442):1-8.

Choi, Y. et al. (2013). "Identification and Characterization of a Novel Flagellum-Dependent *Salmonella*-Infecting Bacteriophage, iEPS5," Appl Environ Microb 79(16):4829-4837.

Click, E.M. et al. (Apr. 1998). "The ToIQRA Proteins Are Required for Membrane Insertion of the Major Capsid Protein of the Filamentous Phage f1 During Infection," J Bacteriol 180(7):1723-1728.

Clokie, M.R. et al. (Jan./Feb. 2011). "Phages in Nature," Bacteriophage 1(1):31-45.

Cvirkaite-Krupovic, V. (2010). "Entry of the Membrane-Containing Bacteriophages Into Their Hosts," Ph.D. Dissertation University of Helsinki., 52 pages.

Datta, D.B. et al. (Sep. 1977). "Major Proteins of the *Escherichia coli* Outer Cell Envelope Membrane as Bacteriophage Receptors," J Bacterial 131(3):821-829.

Daugelavicius, R. et al. (Apr. 2005). "Penetration of Enveloped Double-Stranded RNA Bacteriophages Φ13 and Φ6 Into Pseudomonas syringae Cells," J Virol 79(8):5017-5026.

Daugelavicius, R. et al. (Aug. 1997). "The IncP Plasmid-Encoded Cell Envelope Associated DNA Transfer Complex Increases Cell Permeability," J Bacterial 179(16):5195-5202.

Davison, S. et al. (Oct. 2005). "Identification of the Bacillus anthracis γ Phage Receptor," J Bacteriol 187(19):6742-6749.

Douglas, J.L. et al. (Apr. 1971). "Cell Wall Polymers and Phage Lysis of Lactobacillus plantarum," Biochemistry 10(9):1551-1555.

Drozdz, M. et al. (2012, e-pub. Nov. 18, 2011). "Novel Non-Specific DNA Adenine Methyltransferases," Nucleic Acids Res. 40(5):2119-2130.

Edwards, P. et al. (Sep. 1991). "A Transducing Bacteriophage for Caulobacter crescentus Uses the Paracrystalline Surface Layer Protein as a Receptor," J Bacterial 173(17):5568-5572.

Fehmel, F. et al. (1975). "*Escherichia coli* Capsule Bacteriophages VII. Bacteriophage 29-Host Capsular Polysaccharide Interactions," J Virol 16(3):591-601.

Feige, U. et al. (Jul. 1976). "On the Structure of the *Escherichia coli* C Cell Wall Lipopolysaccharide Core and on Its ΦX174 Receptor Region," Biochem Bioph Res Co 71(2):566-573.

Filippov, A.A. et al. (Sep. 28, 2011). "Bacteriophage-Resistant Mutants in Yersinia pestis: Identification of Phage Receptors and Attenuation for Mice," PLoS One 6:e25486, 11 pages.

Gaidelyte, A. et al. (Apr. 2006). "The Entry Mechanism of Membranecontaining Phage Bam35 Infecting Bacillus thuringiensis," J Bacteriol 188(16):5925-5934.

Garbe, J. et al. (Dec. 2011). "Sequencing and Characterization of Pseudomonas Aeruginosa Phage JG004," BMC Microbiol 11:102, 12 pages.

Garen, A. et al. (1951). "First Two Steps of the Invasion of Host Cells by Bacterial Viruses," J Exp Med pp. 177-189.

German, G.J. et al. (May 11, 2001). "The ToIC Protein of *Escherichia coli* Serves as a Cell-Surface Receptor for the Newly Characterized TLS Bacteriophage," J Mol Biol 308(4):579-585.

Ghannad, M.S. et al. (Mar.-Apr. 2012). "Bacteriophage: Time to Re-Evaluate the Potential of Phage Therapy as a Promising Agent to Control Multidrug-Resistant Bacteria Iran," J Basic Med Sci 15(2):693-701.

Goldberg, E. et al. (1994). "Chapter 34: Recognition, Attachment and Injection," in Molecular Biology of Bacteriophage T4 Washington American Society for Microbiology pp. 347-356.

Guerrero-Ferreira, R.C. et al. (2011). "Alternative Mechanism For Bacteriophage Adsorption to the Motile Bacterium Caulobacter crescentus," P Natl Acad Sci USA pp. 1-7.

Hancock, R.E.W. et al. (1976). "Nature of the Energy Requirement for the Irreversible Adsorption of Bacteriophages T1 and Φ80 to *Escherichia coli*," J Bacteriol 125(2):409-415.

Hannig, G. et al. (Feb. 1998). "Strategies for Optimizing Heterologous Protein Expression in *Escherichia coli*," Trends in Biotechnology 16:54-60.

Hantke, K. (Jan. 1978). "Major Outer Membrane Proteins of *E. coli* K12 Serve as Receptors for the Phages T2 (Protein la) and 434 (Protein lb)," Mol Gen Genet 164(2):131-135.

Hantke, K. et al. (Jan. 1975). "Membrane Receptor Dependent Iron Transport in *Escherichia coli*," FEES Lett. 49(3):301-305.

Hantke, K. et al. (Jul. 1978). "Functional Interaction of the tonA/tonB Receptor System in *Escherichia coli*," J Bacteriol 135(1):190-197.

Hashemolhosseini, S. et al. (Jul. 1994). "Alterations of Receptor Specificities of Coliphages of the T2 Family," J Mol Biol 240(2):105-110.

(56) References Cited

OTHER PUBLICATIONS

Heller, K. et al. (Jan. 1982). "Polymannose O-Antigens of *Escherichia coli*, the Binding Sites for the Reversible Adsorption of Bacteriophage T5+ via the L-Shaped Tail Fibers," J Virol 41(1):222-227.
Heller, K.J. (Nov. 1984). "Identification of the Phage Gene for Host Receptor Specificity by Analyzing Hybrid Phages of T5 and BF23," Virology 139(1):11-21.
Heller, K.J. (Sep. 1992). "Molecular Interaction Between Bacteriophage and the Gram-Negative Cell Envelope," Arch Microbiol 158(4):235-248.
Henning, U. et al. (1994). "Chapter 23: Receptor Recognition by T-Even-Type Coliphages," Karam JD, in Molecular Biology of Bacteriophage T4 Washington American Society for Microbiology pp. 291-298.
Heo, Y.-J. et al. (2007). "Genome Sequence Comparison and Superinfection Between Two Related Pseudomonas aeruginosa Phages, D3112 and MP22," Microbiology 153:2885-2895.
Hill, C. et al. (Jul. 1991). "In Vivo Genetic Exchange of a Functional Domain From a Type II A Methylase Between Lactococcal Plasmid pTR2030 amd a Vori;emt Bacterop[jage," J Bacteriol. 173(14):4363-4370.
Ho, T.D. et al. (Feb. 2001). "OmpC Is the Receptor for Gifsy-1 and Gifsy-2 Bacteriophages of *Salmonella*," J Bacteriol 183(4):1495-1498.
Hyman, P. et al. (2010). "Chapter 7—Bacteriophage Host Range and Bacterial Resistance," Advances in Applied Microbiology 70:217-248.
Iida, S. et al. (Mar. 1987). "Two DNA Antirestriction Systems of Bacteriophage P1, darA, and darB: Characterization of darA-Phages," Virology. 157(1):156-166.
Iwashita, S. et al. (1973). "Smooth Specific Phage Adsorption: Endorhamnosidase Activity of Tail Parts of P22," Biochem Bioph Res Co 55(2):403-409.
Iwashita, S. et al. (Sep. 10, 1976). "Deacetylation Reaction Catalyzed by *Salmonella* phage C341 and Its Baseplate Parts," J Biol Chem 251(17):5361-5365.
Jarrell, K.F. et al. (May 1981). "Isolation and Characterization of a Bacteriophage Specific for the Lipopolysaccharide of Rough Derivatives of Pseudomonas Aeruginosa Strain PAO," J Virol 38(2):529-538.
Kaneko, J.N. et al. (Jul. 2009). "Identification of ORF636 in Phage ΦSLT Carrying Panton-Valentine Leukocidin Genes, Acting as an Adhesion Protein for a Poly(Glycerophosphate) Chain of Lipoteichoic Acid on the Cell Surface of *Staphylococcus aureus*," J. Bacteriol 191(14):4674-4680.
Killmann, H. et al. (Jun. 2001). "FhuA Barrel-Cork Hybrids Are Active Transporters and Receptors," J Bacteriol 183(11):3476-3487.
Kim, M. et al. (2012, e-pub. Aug. 29, 2012). "Spontaneous and Transient Defence Against Bacteriophage by Phase-Variable Glucosylation of O-Antigen in *Salmonella enterica* serovar Typhimurium," Mol Microbiol 86(2):411-425.
Kivela, H.M. et al. (Feb. 2008, e-pub. Dec. 14, 2007). "Genetics for Pseudoalteromonas Provides Tools to Manipulate Marine Bacterial Virus PM2," J Bacteriol 190(4):1298-1307.
Labrie, S.J. et al. (May 2010, e-pub. Mar. 29, 2010). "Bacteriophage Resistance Mechanisms," Nat Rev Microbiol 8:317-327.
Le, S. et al. (Jul. 9, 2013). "Mapping the Tail Fiber as the Receptor Binding Protein Responsible for Differential Host Specificity of Pseudomonas aeruginosa Bacteriophages PaP1 and JG004," PloS One 8(7):e68562, 8 pages.
Letellier, L. et al. (May 1, 2004). "Main Features on Tailed Phage, Host Recognition and DNA Uptake," Front Biosci 9:1228-1239.
Levskaya, A. et al. (Nov. 24, 2005). "Synthetic Biology: Engineering *Escherichia coli* to See Light," Nature 438(7067):441-442.
Lindberg, A.A. (1973). "Bacteriophage Receptors," Annu Rev Micro Biol 27:205-241.
Lindberg, A.A. (1977). "Chapter 8: Bacterial Surface Carbohydrates and Bacteriophage Adsorption," in Sutherland I Surface Carbohydrates of the Prokaryotic Cell London Academic Press pp. 289-356.

Lobocka, M.B. et al. (Nov. 2004). "Genome of Bacteriophage P1," J. Bacteriol. 186(21):7032-7068.
Mahony, J. et al. (2015). "Gram-Positive Phage-Host Interactions," Front Microbiol 6(61):1-2.
Manning, P.A. et al. (1978). "Outer Membrane Proteins of *Escherichia coli* K-12: Isolation of a Common Receptor Protein for Bacteriophage T6 and Colicin K," Mol Gen Genet 158:279-286.
Manning, P.A. et al. (Sep. 1976). "Outer Membrane of *Escherichia coli* K-12: Differentiation of Proteins 3A and 3B on Acrylamide Gels and Further Characterization of con (tolG) Mutants," J Bacteriol 127(3):1070-1079.
Marti, R. et al. (2013, e-pub. Jan. 15, 2013). "Long Tail Fibres of the Novel Broad-Host-Range T-Even Bacteriophage S16 Specifically Recognize *Salmonella* OmpC," Mol Microbiol 87(4):818-834.
McGrath, S. et al. (May 1999). "Molecular Characterization of a Phage-Encoded Resistance System in Lactococcus lactis," Applied Environmental Microbiology. 65(5):1891-1899.
Meadow, P.M. et al. (1978). "Receptor Sites for R-Type Pyocins and Bacteriophage E79 in the Core Part of the Lipopolysaccharide of Pseudomonas Aeruginosa PACI," J Gen Microbiol 108:339-343.
Molineux, I.J. (2001). "No Syringes Please, Ejection of Phage T7 DNA From the Virion Is Enzyme Driven," Mol. Microbiol 40(1):1-8.
Molineux, I.J. et al. (Mar. 2013, e-pub. Feb. 4, 2013). "Popping the Cork: Mechanism of Phage Genome Ejection," Nat Rev Microbiol 11:194-204.
Monteville, M.R. et al. (Sep. 1994). "Lactococcal bacteriophages Require a Host Cell Wall Carbohydrate and a Plasma Membrane Protein for Adsorption and Ejection of DNA," Appl Environ Microb 60(9):3204-3211.
Morona, R. et al. (Aug. 1984). "Host Range Mutants of Bacteriophage Ox2 Can Use Two Different Outer Membrane Proteins of *Escherichia coli* K-12 as Receptors," J Bacteriol 159(2):579-582.
Morona, R. et al. (Nov. 1986). "New Locus (ttr) in *Escherichia coli* K-12 Affecting Sensitivity to Bacteriophage T2 and Growth on Oleate as the Sole Carbon Source," J Bacteriol 168(2):534-540.
Munsch-Alatossava, P. et al. (Dec. 24, 2013). "The Extracellular Phage-Host Interactions Involved in the Bacteriophage LL-H Infection of *Lactobacillus delbrueckii* ssp. *lactis* ATCC 15808," Front Microbial 4(408):1-5.
Mutoh, N. et al. (Nov. 1978). "Role of Lipopolysaccharide and Outer Membrane Protein of *Escherichia coli* K-12 in the Receptor Activity for Bacteriophage T4," J Bacteriol 136(2):693-699.
Norris, J.S. et al. (2000). "Prokaryotic Gene Therapy to Combat Multidrug Resistant Bacterial Infection," Gene Therapy 7:723-725.
O'Loughlin, J.L. et al. (Feb. 19, 2015). Analysis of the Campylobacter jejuni Genome by Smrt DNA Sequencing Identifies Restriction-Modification Motifs PLoS One. e0118533, 18 pages.
Pickard, D. et al. (Nov. 2010, e-pub. Sep. 3, 2010). "A Conserved Acetyl Esterase Domain Targets Diverse Bacteriophages to the Vi Capsular Receptor of *Salmonella enterica* Serovar Typhi," J Bacterial 192(21):5746-5754.
Picken, R.N. et al. (1977). "Bacteriophage-Resistant Mutants of *Escherichia coli* K12. Location of Receptors Within the Lipopolysaccharide," J Gen Microbiol 102:305-318.
Prehm, P. et al. (1976). "On a Bacteriophage T3 and T4 Receptor Region Within the Cell Wall Lipopolysaccharide of *Echerichia coli* B," J Mol Biol 101:277-281.
Rakhuba, D.V. et al. (2010). "Bacteriophage Receptors, Mechanisms of Phage Adsorption and Penetration Into Host Cell Pol," J Microbiol 59(3):145-155.
Randall-Hazelbauer, L. et al. (Dec. 1973). "Isolation of the Bacteriophage Lambda Receptor From *Escherichia coli*," J Bacterial 116(3):1436-1446.
Reske, K. et al. (1973). "Enzymatic Degradation of O-Antigenic Lipopolysaccharides by Coliphage Ω8," Eur J Biochem 36:167-171.
Ricci, V. et al. (Mar. 2010, e-pub. Jan. 15, 2010). "Exploiting the Role of TolC in Pathogenicity: Identification of a Bacteriophage for Eradication of *Salmonella serovars* from Poultry," Applied and Envir. Microbiology 76(5):1704-1706.

(56) References Cited

OTHER PUBLICATIONS

Riede, I. (Jan. 1987). "Receptor Specificity of the Short Tail Fibres (gp12) of T-Even Type *Escherichia coli* Phages," Mol Gen Genetics 206:110-115.
Roa, M. (Nov. 1979). "Interaction of Bacteriophage K10 With Its Receptor, The lamB Protein of *Escherichia coli*," J Bacterial 140(2):680-686.
Roberts et al. (Jan. 2015, e-pub. Nov. 5, 2015). "Rebase—A Database for DNA Restriction and Modification: Enzymes, Genes and Genomes," Nucleic Acids Res 43(D1):D298-D299.
Roberts, R. J. et al.(2003). "Survey and Summary: a Nomenclature for Restriction Enzymes, DNA Methyltransferases, Homing Endonucleases and Their Genes," Nucleic Acids Res. 31(7):1805-1812.
Russel, M. et al. (Nov. 1988). "Low-Frequency Infection of F-Bacteria by Transducing Particles of Filamentous Bacteriophages," J Bacterial 170(11):5312-5316.
Sandulache, R. et al. (1985). "The Cell Wall Receptor for Bacteriophage Mu G(−) in Erwinia and *Escherichia coli* C," FEMS Microbiol Lett 28:307-310.
Sandulache. R. et al. (Oct. 1984). "Cell Wall Receptor for Bacteriophage Mu G(+)," J Bacterial 160(1):299-303.
Schade, S.Z. et al. (Jun. 1967). "How Bacteriophage x Attacks Motile Bacteria," J Virol 1(3):599-609.
Schwartz, M. (1980). "Chapter 4: Interaction of Phages With Their Receptor Proteins," Virus Receptors pp. 59-94.
Sharma, S. et al. (2017). Bacteriophages and Its Applications: an Overview,: Folia Microbiol 62:17-55.
Shaw, D.R.D. et al. (Oct. 1971). "O-Acetyl Groups as a Component of the Bacteriophage Receptor on *Staphylococcus aureus* Cell Walls," J Bacterial 108(1):584-585.
Shin, H. et al. (Aug. 21, 2012). "Receptor Diversity and Host Interaction of Bacteriophages Infecting *Salmonella enterica* Serovar Typhimurium," PLoS One 7(8):e43392, 11 pages.
Skurray, R.A. et al. (Sep. 1974). "Con-Mutants: Class of Mutants in *Escherichia coli* K-12 Lacking a Major Cell Wall Protein and Defective in Conjugation and Adsorption of a Bacteriophage," J Bacterial 119(3):726-735.
Srivastava, P. et al. (Apr. 2005). "Gene Expression Systems in Corynebacteria," Protein Expr Purif 40(2):221-229.
Stirm, S. et al. (Sep. 1971). "Bacteriophage Particles With Endo-Glycosidase Activity," J Virol 8(3):343-346.
Sukupolvi, S. (1984). "Role of Lipopolysaccharide in the Receptor Function for Bacteriophage Ox2," FEMS Microbial Lett 21:83-87.
São-José, C. et al. (Dec. 2004). "Bacillus subtilis Operon Encoding a Membrane Receptor for Bacteriophage SPP1," J Bacterial 186(24):8337-8346.
Takeda, K. et al. (1973). "Receptor Splitting Enzyme of *Salmonella* Phage ε34," Annu Rep Inst Virus Res 16:25-26.
Temple, G.S. et al. (1986). "Isolation and Characterization of a Lipopolysaccharide-Specific Bacteriophage of Pseudomonas aeruginosa," Microbios. 45(183):81-91.
Terpe, K. (2006, e-pub. Jun. 22, 2006). "Overview of Bacterial Expression Systems for Heterologous Protein Production: From Molecular and Biochemical Fundamentals to Commercial Systems," Appl. Microbiol, Biotechnol. 72:211-222.
Thurow, H. et al. (May 1975). "Bacteriophage-Borne Enzymes in Carbohydrate Chemistry: Part I—On the Glycanase Activity Associated With Particles of Klebsiella Bacteriophage No. 11," Carbohyd Res 41(1):257-271.
U.S. Appl. No. 16/626,035, filed Dec. 23, 2019, for Clube et al. (not submitted herewith pursuant to the waiver of 37 C.F.R. 1.98(a)(2)(iii) issued by the Office on Sep. 21, 2004).
U.S. Appl. No. 90/014,230, filed Dec. 3, 2018, for Clube et al. (not submitted herewith pursuant to the waiver of 37 C.F.R. 1.98(a)(2)(iii) issued by the Office on Sep. 21, 2004).
Van Alphen, L. et al. (Mar. 1977). "Major Outer Membrane Protein d of *Escherichia coli* K12: Purification and In Vitro Activity of Bacteriophage k3 and f-pilus Mediated Conjugation," FEBS Lett 75(1):285-290.
Verhoef, C. et al. (1977). "Mapping of a Gene for a Major Outer Membrane Protein of *Escherichia coli* K12 With the Aid of a Newly Isolated Bacteriophage," Mol Gen Genet. 150:103-105.
Vidaver, A.K. et al. (May 1973). "Bacteriophage Φ6: a Lipid-Containing Virus of Pseudomonas phaseolicola," J Virol 11(5):799-805.
Vinga, I. et al. (2006). "Chapter 9: Bacteriophage Entry in the Host Cell," in Modern Bacteriophage Biology and Biotechnology 1:165-205.
Vinga, I. et al. (2012, e-pub. Dec. 15, 2011). "Role of Bacteriophage SPP1 Tail Spike Protein gp21 on Host Cell Receptor Binding and Trigger of Phage DNA Ejection," Mol Microbiol 83(2):289-303.
Wayne, R. et al. (Feb. 1975). "Evidence for Common Binding Sites for Ferrichrome Compounds and Bacteriophage 180 in the Cell Envelope of *Escherichia coli*," J Bacteriol 121(2):497-503.
Wendlinger, G. et al. (1996). "Bacteriophage Receptors on Listeria monocytogenes Cells Are the N-Acetylglucosamine and Rhamnose Substituents of Teichoic Acids or the Peptidoglycan Itself," Microbiology 142:985-992.
Westwater, C. et al. (Apr. 2003). "Use of Genetically Engineered Phage to Deliver Antimicrobial Agents to Bacteria: an Alternative Therapy for Treatment of Bacterial Infections," Antimicrobial Agents and Chemotherapy 47(4):1301-1307.
Wright, A. et al. (1980). "Chapter 3: Lipopolysaccharide as a Bacteriophage Receptor," in Virus Receptors London Chapman & Hall pp. 27-57.
Xia, G. et al. (Aug. 2011, e-pub. Jun. 3, 2011). "Wall Teichoic Acid-Dependent Adsorption of Staphylococcal siphovirus and myovirus," J Bacteriol 193(15):4006-4009.
Xiang, Y. et al. (May 15, 2009). "Crystallographic Insights Into the Autocatalytic Assembly Mechanism of a Bacteriophage Tail Spike," Mol Cell 34:375-386.
Yokota, S.-I. et al. (Sep. 1994). "Identification of the Lipopolysaccharide Core Region as the Receptor Site for a Cytotoxin-Converting Phage, ΦCTX, of Pseudomonas aeruginosa," J Bacteriol 176(17):5262-5269.

\* cited by examiner

PROPAGATOR CELLS AND METHODS FOR PROPAGATING PHAGE, IN PARTICULAR FOR DELIVERING CRISPR-CAS COMPONENTS VIA PROBIOTIC ORGANISMS

CROSS REFERENCE TO RELATED APPLICATIONS

This application is a national stage application under 35 U.S.C. § 371 of International Application No. PCT/EP2018/071454, filed internationally on Aug. 8, 2018, which claims priority benefit to United Kingdom Application No. 1712733.3, filed Aug. 8, 2017, the contents of which are incorporated herein by reference in their entirety.

BACKGROUND

Bacteriophages (phages) are a phylum of viruses that infect bacteria, and are distinct from the animal and plant viruses. Phages can have either a "lytic" life cycle, a "lysogenic" life cycle that can potentially become lytic, or a "non-lytic" life cycle. Phages replicating through the lytic cycle cause lysis of the host target bacterial cell as a normal part of their life cycles. Phages replicating through the lysogenic cycles are called temperate phages, and can either replicate by means of the lytic life cycle and cause lysis of the host bacterium, or they can incorporate their DNA into the host bacterial DNA and become noninfectious prophages. Bacteriophages are bacterial viruses that only infect and multiply within their specific bacterial hosts. Host specificity is generally found at strain level, species level, or, more rarely, at genus level. This specificity allows for directed targeting of dangerous bacteria using phages. The adsorption of bacteriophages onto host cells is, in all but a few rare cases, a sine qua non condition for the onset of the infection process.

The natural capability of phages to infect and kill bacteria, together with the specificity of the phage-bacterial interactions, is the basic phenomena on which the concept of phage therapy is built. Therefore, phages that possess lytic life cycle are suitable candidates for phage therapy. The use of phage in food production has recently become an option for the food industry as a novel method for biocontrol of unwanted pathogens, enhancing the safety of especially fresh and ready-to-eat food products.

International Patent Application No. WO 00/69269 discloses the use of certain phage strain for treating infections caused by Vancomycin-sensitive as well as resistant strains of *Enterococcus faecium*, and International Patent Application No. WO 01/93904 discloses the use of bacteriophage, alone or in combination with other anti-microbial means, for preventing or treating gastrointestinal diseases associated with the species of the genus *Clostridium*.

US Patent Application No. 2001/0026795 describes methods for producing bacteriophage modified to delay inactivation by the host defense system, and thus increasing the time period in which the phage is active in killing the bacteria.

US Patent Application No. 2002/0001590 discloses the use of phage therapy against multi-drug resistant bacteria, specifically methicillin-resistant *Staphylococcus aureus*, and International Patent Application No. WO 02/07742 discloses the development of bacteriophage having multiple host range.

The use of phage therapy for the treatment of specific bacterial-infectious disease is disclosed, for example, in US Patent Application Nos. 2002/0044922; 2002/0058027 and International Patent Application No. WO 01/93904.

However, commercial scale production of bacteriophage compositions for therapeutic use is still limited. In current techniques, the titer of the phage composition is low, usually in the range of $10^9$-$10^{11}$ pfu/ml on a laboratory scale, and $10^7$-$10^9$ on a commercial scale, whereas the titer typically required for therapeutic use is still limited. In current techniques, the titer of the phage composition is low, usually in the range of $10^9$-$10^{11}$ pfu/ml on a laboratory scale, and $10^7$-$10^9$ on a commercial scale, whereas the titer typically required for phage therapy is $10^{12}$ pfu/ml. Additionally, to reach the desirable titer, very large volumes of liquid are required.

US20160333348 describes the use of CRISPR/Cas systems delivered to host target bacterial cells using phage as vectors. In principle, phage can be grown at volume in the cognate host cell using standard bacterial culture techniques and equipment. Growth of such phage or lytic phage in the target host cells may, however, be hampered by host cell killing by the resident phage by lysis and/or by CRISPR/Cas targeting of host DNA or by any other anti-host mechanism or agent encoded by the phage nucleic acid and which is active in host cells.

As bacteriophage use in industrial application grows there is a need for commercial quantities of identified bacteriophage. Therefore, there is a need for a method for production of phage that provides good yield titer and/or reduces manufacturing volume.

SUMMARY OF THE INVENTION

The invention provides a solution by providing propagator cells for propagating phage. To this end, the invention provides:

In a First Configuration

A method of producing a population of phage, wherein the phage are of a first type capable of infecting cells of a first bacterial species or strain (host cells) by binding a cell-surface receptor comprised by bacteria of said species or strain, the method comprising
  (a) Providing a population of second cells comprising the receptor on the surface thereof, wherein the second cells are of a second species or strain, wherein the second species or strain is different from the first species or strain;
  (b) Infecting the second cells with phage of said first type;
  (c) Propagating the phage in the second cells, thereby producing the population of phage; and
  (d) Optionally isolating phage of said population.

In a Second Configuration

A cell (propagator cell) for propagating phage, wherein the phage are of a first type capable of infecting cells of a first bacterial species or strain (host cells) by binding a cell-surface receptor comprised by bacteria of said species or strain, the propagator cell comprising the receptor on the surface thereof, wherein the propagator cell is of a second species or strain, wherein the second species or strain is different from the first species or strain, whereby the propagator cell is capable of being infected by phage of said first type for propagation of phage therein.

In a Third Configuration

A population of propagator cells according to the invention, optionally comprised in a fermentation vessel for culturing the propagator cells and propagating phage of said first type.

BRIEF DESCRIPTION OF THE DRAWINGS

FIG. 1. A bacterial production strain (1) was engineered to express a receptor (2) recognized by a helper phage (line X) while non-receptor containing cells (line Y) served as control. Both lines were then transformed with a CGV and infected with a helper phage to produce CGC-PLP (3). Only in line X harbouring the helper phage receptor, CGV-PLP was produced (4) that could be used to deliver DNA to a target cell population expressing the phage receptor FIG. 2. Delivery of CGV to target cells ATCC43888 (obtained from ATCC) or EMG-2 (obtained from Coli Genetic Stock Center, CGSC) both expressing the receptor recognized by the CGV-PLP. Lysates used for the infection was produced on production strains harboring the receptor for the helper phage (filled bars) or the control strain with no receptor (open bars). Only the production strain with the receptor where the helper phage was able to infect and produce CGV-PLP was able to produce a CGV-PLP lysate capable of infecting the target cell population.

DETAILED DESCRIPTION

Figure 1:
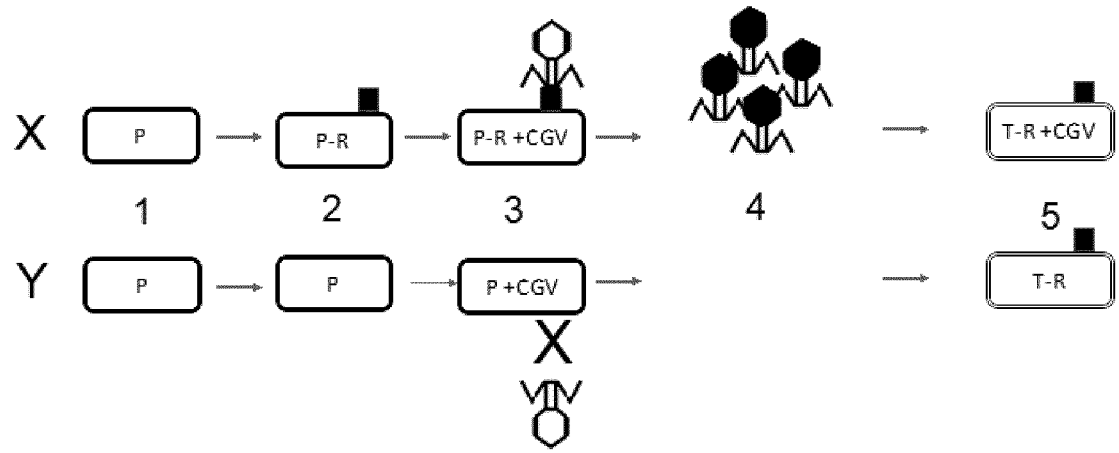
FIG. 1.

The invention recognises the advantage of artificially altering receptors expressed by bacterial cells (or selecting cells according to the profile of receptors naturally expressed), for example in the use of cells that can be cultured at scale and are useful for propagating and growing up useful phage populations at scale (eg, commercial scale). Such phage, for example, may encode a HM-crRNA or gRNA as described in US20160333348, which phage are useful for killing host bacterial cells comprised by humans, animals, plants, foodstuffs, beverages, cosmetics, environments (eg, soil, waterway, water reservoir or oil recovery environments), such as those applications described in US20160333348, the disclosure of which is incorporated herein by reference.

Proteinaceous receptors are mainly outer membrane proteins; sugar moieties include those that compose the cell wall, pellicles, teichoic and LTA. The receptor of the invention is, for, example selected from any of these.

Bacteriophage adsorption initiates the infection process. Through a series of interactions between binding proteins of the bacteriophage (phage) and receptors on the bacterial cell surface, the virus recognizes a potentially sensitive host and then positions itself for DNA ejection. Phage adsorption is thus not only a crucial step in the infection process, but also represents the initial point of contact between virus and host and dictates host range specificity.

Bacteriophage adsorption generally consists of three steps: initial contact, reversible binding and irreversible attachment (Duckworth 1987). The first step involves random collisions between phage and host caused by Brownian motion, dispersion, diffusion or flow (Kokjohn and Miller 1992). In the reversible step, binding to bacterial surface components is not definitive and the phage can desorb from the host. This process, firstly identified by Garen and Puck (1951) through experimental observations of phage detachment after elution, may serve to keep the phage close to the cell surface as it searches for a specific receptor (Kokjohn and Miller 1992). The specific connection between bacterial receptor and phage-binding domains is sometimes mediated by an enzymatic cleavage. This step triggers conformational rearrangements in other phage molecules that allow the insertion of the genetic material into the host (for further details on the mechanism of phage genome ejection, see the review by Molineux and Panja (2013)).

Numerous review studies have highlighted the extensive range of host-associated receptors (proteins, sugars and cell surface structures) that bacteriophages target during adsorption (Lindberg 1977; Schwartz 1980; Wright, McConnell and Kanegasaki 1980; Heller 1992; Frost 1993; Henning and Hashemolhosseini 1994; Vinga et al. 2006; Rakhuba et al. 2010; Chaturongakul and Ounjai 2014). The nature and location of the host cell receptors recognised by bacteriophages varies greatly depending on the phage and host. They range from peptide sequences to polysaccharide moieties. In fact, bacteriophages have been shown to bind to receptors located in the walls of both Gram-positive (Xia et al. 2011) and Gram-negative bacteria (Marti et al. 2013), in bacterial capsules or slime layers (Fehmel et al. 1975), and in appendages [e.g. pili (Guerrero-Ferreira et al. 2011) and flagella (Shin et al. 2012)]. This diversity in receptors and structures involved is a testament to the multiplicity of mechanisms developed by phages and hosts to overcome the evolutionary strategies adopted by their counterparts. It is not unexpected to encounter so many possibilities considering the diversity and staggering amount of phages estimated to populate the different environments of the planet (Clokie et al. 2011). Nevertheless, in all cases, adsorption has so far been shown to involve either constituents of the bacterial cell wall or protruding structures. In an embodiment, therefore, a receptor in the present invention can be any such receptor mentioned in this paragraph or elsewhere in this disclosure.

Optionally, the receptor comprises lipopolysaccharide (LPS), a heptose moiety, the host's glycosylated cell wall teichoic acid (WTA), YueB, or a receptor recognized by a tail fiber protein of the phage or gp21 of the phage.

Receptors in the Cell Wall of Gram-Positive Bacteria

Peptidoglycan, or murein, is an important component of the bacterial cell wall and is often involved in bacteriophage adsorption. It is a polymer composed of multiple units of amino acids and sugar derivatives-N-acetylglucosamine and N-acetylmuramic acid. These sugar constituents are connected through glycosidic bonds, forming glycan tetrapeptide sheets that are joined together through the cross-linking of amino acids. The cross-linking occurs through peptide bonds between diaminopimelic acid (an amino acid analog) and D-alanine, or through short peptide interbridges. These interbridges are more numerous in Gram-positive bacteria, leading to their characteristically thicker cell walls.

Another main component of the cell wall of Gram-positive bacteria that can be involved in phage adsorption is teichoic acid-polysaccharides composed of glycerol phosphate or ribitol phosphate and amino acids. They are bonded to the muramic acid of peptidoglycans. When teichoic acids are bonded to the lipids of the plasma membrane, they are called lipoteichoic acids (LTA). Further details of the composition of cell walls of bacteria can be found in Tortora, Funke and Case (2007), Willey, Sherwood and Woolverton (2008), Pommerville (2010) and Madigan et al. (2012).

The majority of the receptors so far identified are associated either with peptidoglycan or teichoic acid structures (Table 1). Out of 30 phages targeting Gram-positive bacteria reported in Table 1, only 10 utilize other structures for adsorption. Among these 10 phages, 9 display interactions with residues of either teichoic acid (phage SPP1) or peptidoglycan (phages 5, 13, c2, h, m13, kh, L and p2) for reversible binding. This highlights the important role these structures may play in the adsorption of phage to Gram-positive bacteria.

Optionally, the receptor of the invention is peptidoglycan, murein, teichoic acid or lipoteichoic acid (LTA). Optionally, the phage is a phage of a family listed in Table 1 (and optionally the host is the host for the phage as listed in Table 1 and/or the receptor is the receptor for the phage as listed in Table 1). Optionally, the phage is a phage listed in Table 1 (and optionally the host is the host for the phage as listed in Table 1 and/or the receptor is the receptor for the phage as listed in Table 1). In an embodiment, the host and second cells are gram-positive cells. Optionally the host and/or second cells are of a species or strain listed in Table 1 (where the host and second cell species or strains are different). Preferably when the host is a gram-positive bacteria, the receptor is a peptidoglycan. Alternatively, preferably when the host is a gram-positive bacteria, the receptor is a teichoic acid.

TABLE 1

| Phages | Family | Main host | Receptor(s) | References |
|---|---|---|---|---|
| Y | Siphoviridae | *Bacillus anthracis* | Membrane surface-anchored protein gamma phage receptor (GamR) | Davison et al. (2005) |
| SPP1 | Siphoviridae | *Bacillus subtilis* | Glucosyl residues of poly(glycerophosphate) on WTA for reversible binding and membrane protein YueB for irreversible binding | São-José, Baptista and Santos (2004), Baptista, Santos and São-José (2008) |
| $29 | Podoviridae | *Bacillus subtilis* | Cell WTA (primary receptor) | Xiang et al. (2009) |
| Bam35 | Tectiviridae | *Bacillus thuringiensis* | N-acetyl-muramic acid (MurNAc) of peptidoglycan in the cell wall | Gaidelyte et al. (2006) |
| LL-H | Siphoviridae | *Lactobacillus delbrueckii* | Glucose moiety of LTA for reversible adsorption and negatively charged glycerol phosphate group of the LTA for irreversible binding | Munsch-Alatossava and Alatossava (2013) |
| B1 | Siphoviridae | *Lactobacillus plantarum* | Galactose component of the wall polysaccharide | Douglas and Wolin (1971) |
| B2 | Siphoviridae | *Lactobacillus plantarum* | Glucose substituents in teichoic acid | Douglas and Wolin (1971) |
| 513c2hml3khL | Siphoviridae | *Lactococcus lactis* | Rhamnose[a] moieties in the cell wall peptidoglycan for reversible binding and membrane phage infection protein (PIP) for irreversible binding | Monteville, Ardestani and Geller (1994) |
| φLC3TP901ermTP901-1 | Siphoviridae | *Lactococcus lactis* | Cell wall polysaccharides | Ainsworth, Sadovskaya and Vinogradov (2014) |
| p2 | Siphoviridae | *Lactococcus lactis* | Cell wall saccharides for reversible attachment and pellicle[b] phosphohexasaccharide motifs for irreversible adsorption | Bebeacua et al. (2013) |
| A511 | Myoviridae | *Listeria monocytogenes* | Peptidoglycan (murein) | Wendlinger, Loessner and Scherer (1996) |

TABLE 1-continued

| Phages | Family | Main host | Receptor(s) | References |
|---|---|---|---|---|
| A118 | Siphoviridae | *Listeria monocytogenes* | Glucosaminyl and rhamnosyl components of ribitol teichoic acid | Wendlinger, Loessner and Scherer (1996) |
| A500 | Siphoviridae | *Listeria monocytogenes* | Glucosaminyl residues in teichoic acid | Wendlinger, Loessner and Scherer (1996) |
| φ812φK | Myoviridae | *Staphylococcus aureus* | Anionic backbone of WTA | Xia et al. (2011) |
| 52A | Siphoviridae | *Staphylococcus aureus* | O-acetyl group from the 6-position of muramic acid residues in murein | Shaw and Chatterjee (1971) |
| Wφ13φ47φ77φSa2m | Siphoviridae | *Staphylococcus aureus* | N-acetylglucosamine (GlcNAc) glycoepitope on WTA | Xia et al. (2011) |
| φSLT | Siphoviridae | *Staphylococcus aureus* | Poly(glycerophosphate) moiety of LTA | Kaneko et al. (2009) |

[a] Monteville, Ardestani and Geller (1994) noted that since phages can also bind to glucose and galactose moieties in the cell wall, these might, to a lesser extent, be involved in the adsorption mechanism;
[b] Pellicle is a protective polysaccharide layer that covers the cell surface of Lactococcus lactis(Chapot-Chartier et al. 2010).

Receptors in the Cell Wall of Gram-Negative Bacteria

In Gram-negative bacteria, the peptidoglycan layer is relatively thin and is located inward of the outer membrane, the major component of the cell wall. These two layers are connected by Braun's lipoproteins. The outer membrane is a sophisticated structure composed of a lipid bilayer ornamented with proteins, polysaccharides and lipids; the latter two molecules form the LPS layer. LPSs are complexes that consist of three parts: lipid A, the core polysaccharide and the O-polysaccharide. Lipid A is, in general, composed of fatty acids attached to glucosamine phosphate disaccharides. The core polysaccharide is connected to the lipid A through a ketodeoxyoctonate linker. The core polysaccharide and the O-polysaccharide (O-chain or O-antigen) contain several units of sugar residues extending outward to the outer membrane. Cells that contain all three components of the LPS are denominated as smooth (S) type and those that lack the O-polysaccharide portion are distinguished as rough (R) type. In general, the saccharides composing the O-antigen are highly variable and those of the core polysaccharide are more conserved among species. Because of this, phages specific to only S-type strains tend to target the O-polysaccharide and, thus, have generally a narrower host range when compared to those able to adsorb to R-type cells (Rakhuba et al. 2010).

Table 2(a) compiles Gram-negative bacterial receptors located in the cell wall that interact with phage receptor-binding proteins (RBPs). Interestingly, in coliphages there is no preference for proteinaceous or polysaccharide receptors: some phages adsorb on cell wall proteins, some on sugar moieties and others require both structures for adsorption. In the case of *Salmonella* phages, the picture is not so different: some use proteins, some sugar moieties and some both types of receptors. On the other hand, *Pseudomonas* phages commonly adsorb onto polysaccharide receptors. Although definitive conclusions cannot be drawn from such a small sample size, it should be noted that *Pseudomonas* can have two LPS moieties, a short chain LPS named A band and a longer B-band LPS (Beveridge and Graham 1991).

Optionally, the receptor is a host cell wall protein. Optionally, the receptor is a saccharide. Optionally, the receptor comprises O-antigen, LPS lipid A or LPS core polysaccharide. In an example, the receptor is smooth LPS or rough LPS. Optionally, the host cells are S-type bacteria and the receptor comprises O-antigen of the host. Optionally, the host cells are R-type bacteria and the receptor comprises LPS lipid A of the host.

Optionally, the receptor is a host cell wall protein. Optionally, the receptor is a saccharide. Optionally, the receptor comprises O-antigen, LPS lipid A or LPS core polysaccharide. In an example, the receptor is smooth LPS or rough LPS. Optionally, the host cells are S-type bacteria and the receptor comprises O-antigen of the host. Optionally, the host cells are R-type bacteria and the receptor comprises LPS lipid A of the host.

In an example, the host is *E coli* and the phage are coliphage, wherein the receptor is a polysaccharide receptor and/or a host cell wall protein receptor. In an example, the second cells are engineered to express *E coli* polysaccharide receptor and/or an *E coli* cell wall protein receptor, wherein the *E coli* is optionally of the same strain as the host cells.

In an example, the host is *Salmonella*, wherein the receptor is a polysaccharide receptor and/or a host cell wall protein receptor. In an example, the second cells are engineered to express *Salmonella* polysaccharide receptor and/or a *Salmonella* cell wall protein receptor, wherein the *Salmonella* is optionally of the same strain as the host cells.

In an example, the host is *Pseudomonas*, wherein the receptor is a polysaccharide receptor. In an example, the second cells are engineered to express *Pseudomonas* polysaccharide receptor, wherein the *Pseudomonas* is optionally of the same strain as the host cells.

Optionally, the phage is a phage of a family listed in Table 2 (and optionally the host is the host for the phage as listed in Table 2 and/or the receptor is the receptor for the phage as listed in Table 2). Optionally, the phage is a phage listed in Table 2 (and optionally the host is the host for the phage as listed in Table 2 and/or the receptor is the receptor for the phage as listed in Table 2).

In an embodiment, the host and second cells are gram-negative cells. Preferably, the second cells are *E coli* cells. Optionally the host and/or second cells are of a species or strain listed in Table 2 (where the host and second cell species or strains are different).

In an example, the host is *E coli* and the phage are coliphage, wherein the receptor is a polysaccharide receptor and/or a host cell wall protein receptor. In an example, the second cells are engineered to express *E coli* polysaccharide receptor and/or an *E coli* cell wall protein receptor, wherein the *E coli* is optionally of the same strain as the host cells.

In an example, the host is *Salmonella*, wherein the receptor is a polysaccharide receptor and/or a host cell wall protein receptor. In an example, the second cells are engineered to express *Salmonella* polysaccharide receptor and/or a *Salmonella* cell wall protein receptor, wherein the *Salmonella* is optionally of the same strain as the host cells.

In an example, the host is *Pseudomonas*, wherein the receptor is a polysaccharide receptor. In an example, the second cells are engineered to express *Pseudomonas* polysaccharide receptor, wherein the *Pseudomonas* is optionally of the same strain as the host cells.

Optionally, the phage is a phage of a family listed in Table 2 (and optionally the host is the host for the phage as listed in Table 2 and/or the receptor is the receptor for the phage as listed in Table 2). Optionally, the phage is a phage listed in Table 2 (and optionally the host is the host for the phage as listed in Table 2 and/or the receptor is the receptor for the phage as listed in Table 2).

In an embodiment, the host and second cells are gram-negative cells. Preferably, the second cells are *E coli* cells. Optionally the host and/or second cells are of a species or strain listed in Table 2 (where the host and second cell species or strains are different).

Table 2(b) reports cases where phages not only adsorb onto bacterial surfaces but also enzymatically degrade the sugar moieties in the O-chain structure. It should be noted that all these phages belong to the Podoviridae family.

TABLE 2

Receptors in the cell wall of Gram-negative bacteria. Host names are ordered alphabetically.

| Phages | Family | Main host | Receptor(s) | References |
|---|---|---|---|---|
| (a) Receptors that bind to RBP of phages | | | | |
| φCr30 | Myoviridae | *Caulobacter crescentus* | Paracrystalline surface (S) layer protein | Edwards and Smit (1991) |
| 434 | Siphoviridae | *Escherichia coli* | Protein Ib (OmpC) | Hantke (1978) |
| BF23 | Siphoviridae | *Escherichia coli* | Protein BtuB (vitamin $B_{12}$ receptor) | Bradbeer, Woodrow and Khalifah (1976) |
| K3 | Myoviridae | *Escherichia coli* | Protein d or 3A (OmpA) with LPS | Skurray, Hancock and Reeves (1974); Manning and Reeves (1976); Van Alphen, Havekes and Lugtenberg (1977) |
| K10 | Siphoviridae | *Escherichia coli* | Outer membrane protein LamB (maltodextran selective channel) | Roa (1979) |
| Me1 | Myoviridae | *Escherichia coli* | Protein c (OmpC) | Verhoef, de Graaff and Lugtenberg (1977) |
| Mu G(+) | Myoviridae | *Escherichia coli* | Terminal Glcα-2Glα1- or GlcNAcα1-2Glcα1 - of the LPS | Sandulache, Prehm and Kamp (1984) |
| Mu G(−) | Myoviridae | *Escherichia coli* | Terminal glucose with a β1,3 glycosidic linkage | Sandulache et al. (1985) |
| | | *Erwinia* | Terminal glucose linked in β1,6 configuration | |
| M1 | Myoviridae | *Escherichia coli* | Protein OmpA | Hashemolhosseini et al. (1994) |
| Ox2 | Myoviridae | *Escherichia coli* | Protein OmpA[a] | Morona and Henning (1984) |
| ST-1 | Microviridae | *Escherichia coli* | Terminal Glcα-2Glcα1- or GlcNAcα1-2Glcα1 - of the LPS | Sandulache, Prehm and Kamp (1984) |

TABLE 2-continued

Receptors in the cell wall of Gram-negative bacteria. Host names are ordered alphabetically.

| Phages | Family | Main host | Receptor(s) | References |
|---|---|---|---|---|
| TLS | Siphoviridae | *Escherichia coli* | Antibiotic efflux protein TolC and the inner core of LPS | German and Misra (2001) |
| TuIa | Myoviridae | *Escherichia coli* | Protein Ia (OmpF) with LPS | Datta, Arden and Henning (1977) |
| TuIb | Myoviridae | *Escherichia coli* | Protein Ib (OmpC) with LPS | |
| TuII* | Myoviridae | *Escherichia coli* | Protein II* (OmpA) with LPS | |
| T1 | Siphoviridae | *Escherichia coli* | Proteins TonA (FhuA, involved in ferrichrome uptake) and TonB[b] | Hantke and Braun (1975, 1978); Hancock and Braun (1976) |
| T2 | Myoviridae | *Escherichia coli* | Protein Ia (OmpF) with LPS and the outer membrane protein FadL (involved in the uptake of long-chain fatty acids) | Hantke (1978); Morona and Henning (1986); Black (1988) |
| T3 | Podoviridae | *Escherichia coli* | Glucosyl-α-1,3-glucose terminus of rough LPS | Prehm et al. (1976) |
| T4 | Myoviridae | *Escherichia coli* K-12 | Protein O-8 (OmpC) with LPS | Prehm et al. (1976); Mutoh, Furukawa and Mizushima (1978); Goldberg, Grinius and Letellier (1994) |
| | | *Escherichia coli* B | Glucosyl-α-1,3-glucose terminus of rough LPS | |
| T5 | Siphoviridae | *Escherichia coli* | Polymannose sequence in the O-antigen and protein FhuA | Braun and Wolff (1973); Braun, Schaller and Wolff (1973); Heller and Braun (1982) |
| T6 | Myoviridae | *Escherichia coli* | Outer membrane protein Tsx (involved in nucleoside uptake) | Manning and Reeves (1976, 1978) |
| T7 | Podoviridae | *Escherichia coli* | LPS[c] | Lindberg (1973) |
| U3 | Microviridae | *Escherichia coli* | Terminal galactose residue in LPS | Picken and Beacham (1977) |
| λ | Siphoviridae | *Escherichia coli* | Protein LamB | Randall-Hazelbauer and Schwartz (1973) |
| φX174 | Microviridae | *Escherichia coli* | Terminal galactose in the core oligosaccharide of rough LPS | Feige and Stirm (1976) |
| φ80 | Siphoviridae | *Escherichia coli* | Proteins FhuA and TonB[b] | Hantke and Braun (1975,1978); Wayne and Neilands (1975); Hancock and Braun (1976) |
| PM2 | Corticoviridae | *Pseudoalteromonas* | Sugar moieties on the cell surface[d] | Kivela et al. (2008) |
| E79 | Myoviridae | *Pseudomonas aeruginosa* | Core polysaccharide of LPS | Meadow and Wells (1978) |

TABLE 2-continued

Receptors in the cell wall of Gram-negative bacteria. Host names are ordered alphabetically.

| Phages | Family | Main host | Receptor(s) | References |
|---|---|---|---|---|
| JG004 | Myoviridae | *Pseudomonas aeruginosa* | LPS | Garbe et al. (2011) |
| φCTX | Myoviridae | *Pseudomonas aeruginosa* | Core polysaccharide of LPS, with emphasis on L-rhamnose and D-glucose residues in the outer core | Yokota, Hayashi and Matsumoto (1994) |
| φPLS27 | Podoviridae | *Pseudomonas aeruginosa* | Galactosamine-alanine region of the LPS core | Jarrell and Kropinski (1981) |
| φ13 | Cystoviridae | *Pseudomonas syringae* | Truncated O-chain of LPS | Mindich et al. (1999); Daugelavicius et al. (2005) |
| ES18 | Siphoviridae | *Salmonella* | Protein FhuA | Killmann et al. (2001) |
| Gifsy-1Gifsy-2 | Siphoviridae | *Salmonella* | Protein OmpC | Ho and Slauch (2001) |
| SPC35 | Siphoviridae | *Salmonella* | BtuB as the main receptor and O12-antigen as adsorption-assisting apparatus | Kim and Ryu (2012) |
| SPN1SSPN2TCWSPN4B SPN6TCW SPN8TCW SPN9TCW SPN13U | Podoviridae | *Salmonella* | O-antigen of LPS | Shin et al. (2012) |
| SPN7CSPN9C SPN10H SPN12C SPN14 SPN17T SPN18 | Siphoviridae | *Salmonella* | Protein BtuB | |
| vB_SenM-S16 (S16) | Myoviridae | *Salmonella* | Protein OmpC | Marti et al. (2013) |
| L-413CP2 vir1 | Myoviridae | *Yersinia pestis* | Terminal GlcNAc residue of the LPS outer core. HepII/HepIII and HepI/Glc residues are also involved in receptor activity[e] | Filippov et al. (2011) |
| φJA1 | Myoviridae | *Yersinia pestis* | Kdo/Ko pairs of inner core residues. LPS outer and inner core sugars are also involved in receptor activity[e] | |
| T7$_{Yp}$ Y (YpP-Y) | Podoviridae | *Yersinia pestis* | HepI/Glc pairs of inner core residues. HepII/HepIII and Kdo/Ko pairs are also involved in receptor activity[e] | |
| Pokrovskaya YepE2YpP-G | Podoviridae | Yersinia pestis | HepII/HepIII pairs of inner core residues. HepI/Glc residues are also involved in receptor activity[e] | |

TABLE 2-continued

Receptors in the cell wall of Gram-negative bacteria. Host names are ordered alphabetically.

| Phages | Family | Main host | Receptor(s) | References |
|---|---|---|---|---|
| φA1122 | Podoviridae | *Yersinia pestis* | Kdo/Ko pairs of inner core residues. HepI/Glc residues are also involved in receptor activity[e] | |
| PST | Myoviridae | *Yersinia pseudotuberculosis* | HepII/HepIII pairs of inner core residues[e] | |
| (b) Receptors in the O-chain structure that are enzymatically cleaved by phages | | | | |
| Ω8 | Podoviridae | *Escherichia coli* | The α-1,3-mannosyl linkages between the trisaccharide repeating unit α-mannosyl-1,2-α-mannosyl-1,2-mannose | Reske, Wallenfels and Jann (1973) |
| c341 | Podoviridae | *Salmonella* | The O-acetyl group in the mannosyl-rhamnosyl-O)-acetylgalactose repeating sequence | Iwashita and Kanegasaki (1976) |
| P22 | Podoviridae | *Salmonella* | α-Rhmanosyl 1-3 galactose linkage of the O-chain | Iwashita and Kanegasaki (1973) |
| $\varepsilon^{34}$ | Podoviridae | *Salmonella* | [-β-Gal-Man-Rha-] polysaccharide units of the O-antigen | Takeda and Uetake (1973) |
| Sf6 | Podoviridae | *Shigella* | Rha II 1-α-3 Rha III linkage of the O-polysaccharide. | Lindberg et al. (1978) |

[a]Sukupolvi (1984) suggested that LPS is also required for adsorption of phage Ox2 on *E. coli* and *S. typhimurium*, although the study verified that isolated OmpA is enough to inactivate the phage and that the binding is not increased with the addition of LPS to the protein.
[b]According to Rakhuba et al. (2010), TonB is not a receptor itself, but acts as a mediator of electrochemical potential transmission; Vinga et al, (2006) stated that TonB is a membrane protein required for genome entry; Letellier et al. (2004) explained that TonB is part of a protein complex involved in the energy transduction from the electron transfer chain in the cytoplasmic membrane to the outer membrane receptors and speculated that it possibly might be critical for the genome injection through its interaction with FhuA.
[c]Rhakuba et al. (2010) mentioned proteins FhuA and TonB as the receptors for T7; Molineux (2001) reported that 'Bayer patches', described as adhesion sites between the cytoplasmic membrane and the outer envelope of Gram-negative bacteria, are the proposed receptors for T7.
[d]In 2010 the same group suggested that the adsorption of the phage on the sugar moieties of the host is an initial interaction, and that the true receptor is a protein molecule or protein complex (Cvirkaite-Krupovic 2010).
[e]Kdo, 2-keto-3-deoxy-octulosonic acid; Ko, D-glycero-D-talo-oct-2-ulosonic acid; Hep, heptulose (ketoheptose); Glc, glucose; Gal, galactose; GlcNAc, N-acetylglucosamine (from Filippov et al. 2011).

Receptors in Other Structures of Gram-Negative Bacteria

In this section, bacterial structures, other than cell wall moieties, that also serve as receptors for phages are discussed. These include structures such as flagella, pili and capsules. They can be found in species from both Gram stains. See Table 3 for examples.

Optionally, the receptor of the invention is a flagellum, pilus or capsule component (eg, a component listed in Table 3 in the listed species or as found in a host that is of a different species to that listed). Optionally, the phage is a phage of a family listed in Table 3 (and optionally the host is the host for the phage as listed in Table 3 and/or the receptor is the receptor for the phage as listed in Table 3). Optionally, the phage is a phage listed in Table 3 (and optionally the host is the host for the phage as listed in Table 3 and/or the receptor is the receptor for the phage as listed in Table 3).

Flagella are long thin helical structures that confer motility to cells. They are composed of a basal body, a flagellar hook and a flagellar filament composed of subunits of flagellin proteins (Willey, Sherwood and Woolverton 2008). Table 3(a) reports phages attaching to flagellar proteins. The adhesion of phages to the filament structure is generally reversible and the flagellum's helical movement causes the phage to move along its surface until they reach the bacterial wall. Irreversible adsorption occurs, then, on receptors located on the surface of the bacterium, near the base of the flagellum (Schade, Adler and Ris 1967; Lindberg 1973; Guerrero-Ferreira et al. 2011). Interestingly, some phages (φCbK and φCb13) were observed to contain filaments protruding from their capsids that are responsible for reversible binding onto the host's flagellum; irreversible adsorption occurs only when the phage's tails interact with pili portals on the cell pole (Guerrero-Ferreira et al. 2011). Because for these phages irreversible adsorption occurs on the pilus, even if they interact with the flagellum, they were reported in Table 3(b), which focuses on phages interacting with receptors in pili and mating pair formation structures.

Pili are rod-shaped filamentous appendages used for bacterial conjugation (Lindberg 1973). They extend from the donor cell and attach to receptors on the wall of the recipient cell. A depolymerization of the pilus causes its retraction, bringing both cells closer to each other. Further adhesion of the cells is achieved through binding proteins on their surfaces; genetic material is transferred through this conjugating junction (Madigan et al. 2012). Adsorption to the pilus structure has been so far associated with phages that belong to orders different from Caudovirales (Table 3b). In fact, according to Frost (1993), the families Cystoviridae and Inoviridae compose the majority of phages that adsorb onto pili structures. Interestingly, phages can be selective towards certain parts of the pili. That is the case for F-type phages, whose adsorption occur only on the tip of the pilus (Click and Webster 1998). In other phages, such as 06, the attachment happens at the sides (shaft) of the structure (Daugelavicius et al. 2005).

Capsules are flexible cementing substances that extend radially from the cell wall. They act as binding agents between bacteria and/or between cells and substrates (Beveridge and Graham 1991). Slime layers are similar to capsules, but are more easily deformed. Both are made of sticky substances released by bacteria, and their common components are polysaccharides or proteins (Madigan et al. 2012). Adsorption of phages to capsules or slime layers is mediated by enzymatic cleavage of the exopolysaccharides that compose the layers. The hydrolysis of the layer is a reversible step, whereas irreversible binding is achieved through bonding of the phage with receptors on the cell wall (Rakhuba et al. 2010). As can be seen in Table 3(c), the few phages identified to have RBP recognizing exopolysaccharides are mostly of Podoviridae morphology.

In an example, the host is *Salmonella* (eg, *S enterica* Serovar *Typhimurium*) and the receptor is selected from

TABLE 3

Receptors in bacterial complexes other than cell wall structures. Host names are ordered alphabetically.

| Phages | Family | Main host | Receptor(s) | References |
|---|---|---|---|---|
| (a) Receptors in flagella | | | | |
| SPN2T SPN3C SPN8T SPN9T SPN11T SPN13B SPN16C | Siphoviridae | *Salmonella* | Flagellin protein FliC | Shin et al. (2012) |
| SPN4SSPN5T SPN6T SPN19 | Siphoviridae | *Salmonella* | Flagellin proteins FliC or FljB | |
| iEPS5 | Siphoviridae | *Salmonella* | Flagellal molecular ruler protein Flik | Choi et al. (2013); Chaturongakul and Ounjai (2014) |
| (b) Receptors in pili and mating pair formation structures | | | | |
| φCbK φCb13 | Siphoviridae | *Caulobacter crescentus* | Initial contact between phage head filament and host's flagellum followed by pili portals on the cell pole | Guerrero-Ferreira et al. (2011) |
| FdFff1M13 | Inoviridae | *Escherichia coli* | Tip of the F pilus followed by ToIQRA complex in membrane after pilus retraction | Loeb (1960); Caro and Schnos Click and Webster (1998) (1966); Russel et al. (1988); |
| PRD1 | Tectiviridae | *Escherichia coli* | Mating pair formation (Mpf) complex in the membrane | Daugelavicius et al. (1997) |
| φ6 | Cystoviridae | *Pseudomonas* | Sides of the type IV pilus | Vidaver, Koski and Van Etten (1973); Daugelavicius et al. (2005) |
| MPK7 | Podoviridae | *Pseudomonas aeruginosa* | Type IV pili (TFP) | Bae and Cho (2013) |
| MP22 | Siphoviridae | *Pseudomonas aeruginosa* | Type IV pili (TFP) | Heo et al. (2007) |
| DMS3 | Siphoviridae | *Pseudomonas aeruginosa* | Type IV pili (TFP) | Budzik et al. (2004) |
| (c) Receptors in bacterial capsules | | | | |
| 29 | Podoviridae | *Escherichia coli* | Endoglycosidase hydrolysis in β-D-glucosido-(1,3)-D-glucuronic acid bonds in the capsule composed of hexasaccharides repeating units | Strim et al. (1971); Fehmel et al. (1975) |
| K11 | Podoviridae | *Klebsiella* | Hydrolysis of β-D-glucosyl-(1-3)-β-D-glucuronic acid linkages. The phage is also able to cleave α-D-galactosyl-(1-3)-β-D-glucose bonds | Thurow, Niemann and Stirm (1975) |
| Vi I | Myoviridae | *Salmonella* | Acetyl groups of the Vi exopolysaccharide capsule (a polymer of α-1,4-linked N-acetyl galactosaminuronate) | Pickard et al. (2010) |
| Vi II | Siphoviridae | *Salmonella* | Acetyl groups of the Vi exopolysaccharide capsule (a polymer of α-1,4-linked N-acetyl galactosaminuronate) | |
| Vi IIIVi IVVi VVi VIVi VII | Podoviridae | *Salmonella* | Acetyl groups of the Vi exopolysaccharide capsule (a polymer of α-1,4-linked N-acetyl galactosaminuronate) | | flagella, vitamin $B_{12}$ uptake outer membrane protein, BtuB and lipopolysaccharide-related O-antigen. In an example the receptor is a flagellum or BtuB and the phage are Sipho-viridae phage. In an example the receptor is O-antigen of LPS and the phage are Podoviridae phage. Optionally, the receptor is FliC host receptor or FljB receptor.

Optionally, the host is S enterica or P aeruginosa. Optionally, the receptor is the receptor of the host as listed in Table 4.

TABLE 4

Specific host receptors for Salmonella and P. aeruginosa phages.

| | Specific host receptors | Reference |
|---|---|---|
| S. enterica | Flagellar proteins | |
| | FliC and FljB | Shin et al. (2012) |
| | FliK | Choi et al. (2013) |
| | Outermembrane proteins | |
| | OmpC | Ho and Slauch (2001), Marti et al. (2013) |
| | BtuB | Kim and Ryu (2011) |
| | TolC | Ricci and Piddock (2010) |
| | FhuA | Casjens et al. (2005) |
| | Surface antigens | |
| | O-antigen | Shin et al. (2012) |
| | Vi-antigen | Pickard et al. (2010) |
| P. aeruginosa | Surface antigens | |
| | O-antigen | Le et al. (2013) |
| | Vi-antigen | Temple et al. (1986), Hanlon et al. (2001) |
| | Type IV pili | |
| | PilA | Bae and Cho (2013), Heo et al. (2007) |

The O-antigen structure of *Salmonella* O66 has been established, which reportedly differs from the known O-antigen structure of *Escherichia coli* O166 only in one linkage (most likely the linkage between the O-units) and O-acetylation. The O-antigen gene clusters of *Salmonella* O66 and *E. coli* O166 were found to have similar organizations, the only exception being that in *Salmonella* O66, the wzy gene is replaced by a non-coding region. The function of the wzy gene in *E. coli* O166 was confirmed by the construction and analysis of deletion and trans-complementation mutants. It is proposed that a functional wzy gene located outside the O-antigen gene cluster is involved in *Salmonella* O66 O-antigen biosynthesis, as has been reported previously in Salmonellasero groups A, B and D1. The sequence identity for the corresponding genes between the O-antigen gene clusters of SalmonellaO66 and *E. coli* O166 ranges from 64 to 70%, indicating that they may originate from a common ancestor. It is likely that after the species divergence, *Salmonella* O66 got its specific O-antigen form by inactivation of the wzy gene located in the O-antigen gene cluster and acquisition of two new genes (a wzy gene and a prophage gene for O-acetyl modification) both residing outside the O-antigen gene cluster.

In an example, the second cells are engineered to comprise an expressible *E coli* (eg, *Escherichia coli* O166) wzy gene. In an example, the second cells do not comprise an expressible *E coli* (eg, *Escherichia coli* O166) wzy gene. Optionally, the host cells are *E coli* or *Salmonella* (eg, *Salmonella* O66) cells.

In an example, the phage or particle comprises a phage genome or a phagemid, eg, wherein the genome or phagemid comprises DNA encoding one or more proteins or nucleic acids of interest, such as crRNAs for targeting host cell genomes or antibiotics for killing host cells.

In an alternative, instead of bacteria, the host and second cells (propagator cells) are archaeal cells and the disclosure herein relating to bacteria instead can be read as applying mutatis *mutandis* to archaea.

Target host strains or species of bacteria may comprise restriction-modification system (R-M system), such as R-M comprising restriction endonucleases, that can recognize and cut or otherwise destroy or degrade invading nucleic acid. Host DNA is protected by the action of methyltransferases that methylate host DNA and protect it from the R-M system. It may be desirable, therefore, to provide second bacterial cells (propagator cells) that do not comprise an R-M system or whose genome is devoid of nucleic acid encoding one or more restriction endonucleases which are encoded by host cells. Additionally or alternatively, the second cells comprise nucleic acid encoding one or more methyltransferases which are encoded by host cells, optionally all or substantially all (eg, at least 50, 60, 70 80 or 90%) of all of the methyltransferases encoded by host cells. Optionally, the second cells comprise nucleic acid encoding 1, 2,3 4, 5, 6, 7, 8, 9 or 10 or (or at least 1, 2,3 4, 5, 6, 7, 8, 9 or 10) methyltransferases encoded by host cells.

Advantageously, to produce phage or transduction particles targeting a specific bacterial host population, it may be beneficial to produce the phage or particles in a strain of bacteria related to the target host strain, for example to produce phage or particle nucleic acid (eg, DNA) that can evade host cell defence mechanisms, such as R-M systems or restriction endonuclease action. Optionally, therefore, the host cells and second cells (propagator cells) are cells of the same species (or the same strain of species except that the second cells comprise one or more genetic modifications that are not found in the genomes of host cells; such modification can be deletion of one or more protospacer sequences, for example wherein the host cells comprise such sequence(s) and the phage or particles express crRNA that recognize the sequences in the host cells to guide Cas and to modify the protospacer sequence(s)). For example, modification of the DNA of the phage or particles by methyltransferases in the second bacteria can be useful to shield the DNA against restriction modification once the phage or particles subsequently infect the target host cells where the latter also comprise methyltransferases in common with the second cells. By adapting (or choosing) the second cells as per the invention to display a surface receptor that is also displayed on the host cells, the invention enables phage or particle production in a strain that may display beneficial DNA modification against restriction modification subsequently by the target host bacteria. Usefully, the protospacer sequence(s) to which (in one embodiment) crRNAs encoded by the phage or particles are targeted in the target host bacteria may be deleted or naturally absent in the genome of the second bacteria, such that Cas-mediated cutting of the second cell genomes does not take place during the production of the phage or particles.

A heterologous methyltransferase (MTase) can be used to confer on a production bacterium (propagator bacterium or second cells herein) a similar methylation pattern as that of a target host bacterium. See, for example, WO2016205276, which incorporated herein by reference, for example to provide illustration of how to provide production strain genomes comprising desirable MTases for use in the present invention). In bacteria and archaea, some DNA methyltransferases can be separated into three distinct classes depending on the location of the modification and type of reaction they catalyze. N6-methyladenine (m6A) and N4-methylcytosine (m4C) result from methylation of the amino moiety of adenine and cytosine, respectively, while 5-methylcytosine (m5C) is the result of methylation at the C5 position of cytosine.

A non-limiting example of a DNA MTase useful with the invention includes LlaPI from phage ϕ50, which can be introduced to protect against type II R-M systems in lactococci (Hill et al. J Bacteriol. 173(14):4363-70 (1991)). Optionally, the production bacterium encodes and expresses one or more DNA modification enzymes that catalyse methylation of adenines, eg, to produce N6-methyladenine (m6A). Optionally, the production bacterium encodes and expresses one or more DNA modification enzymes that catalyse methylation of cytosines, eg, to produce N4-methylcytosine (m4C) or 5-methylcytosine (m5C). Optionally, the production bacterium encodes and expresses one or more DNA modification enzymes that catalyse acetimidation of adenine residues. Some R-M systems are sensitive to adenine methylation. Polypeptides that acetimidate the adenine residues in the phage or particle DNA will protect the DNA against such systems. Non-limiting examples of polypeptides that can acetimidate adenine residues in the production host bacteria include the mom gene from phage Mu and the Mu-like prophage sequences (see, *Haemophilus influenzae* Rd (FluMu), *Neisseria meningitidis* type A strain Z2491 (Pnmel) and *H. influenzae* biotype *aegyptius* ATCC 111 16), which converts adenine residues to N(6)-methyladenine, thereby protecting against adenine sensitive restriction enzymes. The methylation patterns conferred by individual methyltransferases can be assessed using established DNA sequencing technologies such as Pacbio SMRT sequencing (O'Loughlin et al. PLoS One. 2015:e0118533). Once generated, the production strain can be used to produce bacteriophage particles for DNA delivery into the target strain.

Bacterial "restriction-modification systems" (R-M systems) comprise (1) methyltransferases that methylate DNA at specific sequences and/or (2) restriction enzymes that cleave DNA that are unmethylated (Types I, II, and III) or methylated (Type IV). The R-M systems constitute a bacterial defence system wherein DNA with foreign methylation patterns is cleaved in multiple locations by the restriction enzymes of the R-M systems. Most: bacteria comprise more than one R-M system. Roberts, R. J. et al. Nucleic Acids Res. 31, 1805-1812 (2003). Type I methyltransferases require the presence of a compatible specificity protein for functionality. Type II and type III methyltransferases do not require any additional proteins to function. Thus, methyltransferases and restriction enzymes useful with this invention (either as targets for modification or inhibition, or as heterologous polypeptides to be expressed in a production bacterium, thereby modifying the R-M system of the production bacterium) can include any methyltransferase or restriction enzyme comprised in a bacterial restriction-modification system (e.g.. Type I, II, III, or IV). Thus, in an example, the genome of the production bacterium (second or propagator cell) encodes a Type I methyltransferase that is also encoded by the host bacterium. Additionally or alternatively, in an example, the genome of the production bacterium (second or propagator cell) encodes a Type II methyltransferase that is also encoded by the host bacterium. Additionally or alternatively, in an example, the genome of the production bacterium (second or propagator cell) encodes a Type III methyltransferase that is also encoded by the host bacterium. Additionally or alternatively, in an example, the genome of the production bacterium (second or propagator cell) encodes a Type IV methyltransferase that is also encoded by the host bacterium.

In an example, two or more (e.g., 2, 3, 4, 5, 6, 7, 8, 9, 10, 11, 12, 13, 14 or 15) nucleic acid sequences encoding enzymes of the endogenous restriction modification system of a production bacterium are disrupted or altered in activity (eg, reduced or eliminated in activity).

A production bacterium (ie, second cell or propagator cell) can be a gram positive or gram negative bacterium. Thus, for example, production bacterium is an *Escherichia coli, Bacillus subtilis, Lactobacillus rhamnosus, Salmonella enteria, Streptococcus thermophilus, Listeria, Campylobacter* or *Staphylococcus aureus* bacterium. In an example, the production bacterium is an *E. coli* strain MG1655, Nissle, BW25113, BL21, TOP10, or MG1655 Δdam Δdcm ΔhsdRMS.

The activity of an enzyme of an endogenous R-M system may be disrupted using methods well known in the art or later developed for disrupting the function and activity of a polypeptide. Such methods can include, but are not limited to, generating point mutations (e.g., missense, or nonsense, or insertions or deletions of single base pairs that result in frame shifts), insertions, deletions, and/or truncations. In some embodiments, a polypeptide inhibitor may be used to disrupt or suppress the activity of an enzyme of a bacterial restriction modification system (R-M system). Such polypeptide inhibitors are known in the art. Polypeptide inhibitors may be encoded, for example, within the phage or particle DNA and/or packaged as proteins in the phage or particle. For example, P1 phage encodes two polypeptide inhibitors that inhibit Type I restriction enzymes found in *E. coli* (Lobocka et al. J. Bacteriol. 186, 7032-7068 (2004)). In some embodiments, an endogenous R-M system may be inhibited or disrupted by the introduction of polypeptide inhibitors, polypeptides that stimulate the activity of the host methylation enzymes to accelerate the methylation and protection of the delivered DNA.

Inhibitors of R-M system enzymes include but are not limited to proteins that degrade a REase (restriction endonuclease), thereby preventing the host R-M enzyme system from cleaving the phage or particle DNA. Non-limiting examples of an R-M enzyme inhibitor that may be used with this invention to disrupt or modify the activity of an endogenous bacterial R-M system enzyme include (a) orf18 from *Enterococcus faecalis*, which produces the protein ArdA that inhibits all major classes of type I R-M systems; and (b) gp0.3 from bacteriophage T7 produces the protein Ocr that sequesters the type I R-M enzyme EcoKI. Additional non-limiting examples of proteins that may be used to block the activity of an enzyme of an R-M system include masking proteins. Masking proteins are packaged into the phage head and upon DNA injection bind the phage DNA, thereby masking R-M recognition sites. Non-limiting examples of masking proteins useful with this invention include DarA and DarB proteins (Iida et al. Virology. 1 57(1): 156-66 (1987)). These proteins are expressed by the P1 bacteriophage during the lytic cycle and are packaged into the head. Upon DNA injection to a host bacterium, they bind and mask the Type I R-M recognition sites.

In addition to or in the alternative, an endogenous R-M system of a production bacterium can be altered/modified through the expression of at least one heterologous methyltransferase. Any methyltransferase that alters the endogenous methylation pattern of a production host bacterium so that the methylation pattern of the production host bacterium is substantially similar to the methylation pattern of the target host bacterium can be used with this invention. The heterologous methyltransferase may be from the same or a different organism as long as it confers a methylation pattern substantially similar to the production host bacterium as the target bacterial strain. A non-limiting example of a DNA MTase useful with the invention includes LlaPI from phage 050, which can be introduced to protect against type II R-M systems in lactococci (McGrath et al. Applied Environmental Microbiology. 65:1891-1899 (1999)). The methylation patterns conferred by individual methyltransferases are then assessed using established DNA sequencing technologies such as Pacbio SMRT sequencing (O'Loughlin et al. PLoS One. 2015:e0118533). Once generated, the production strain is used to produce phage or particles for DNA delivery into the target host strain.

Further heterologous DNA modification enzymes can be expressed in a production bacterium so that the R-M system of the production bacterium is made substantially similar to the R-M system of the target host bacterium. Examples of such DNA modification enzymes useful for this purpose include those that encode polypeptides that convert the adenine residues in the DNA to acetamidoadenine. Polypeptides that convert the adenine residues in the phage or particle DNA to acetamidoadenine will protect the DNA against restriction enzymes that are sensitive to adenine methylation. Non-limiting examples of polypeptides that can convert the adenine residues in the DNA to acetamidoadenine in the production bacteria include the mom gene from phage Mu and the Mu-like prophage sequences (see, *Haemophilus influenzae* Rd (FluMu), *Neisseria meningitidis* type A strain Z2491 (Pnme 1) and *H. influenzae* biotype *aegyptius* ATCC 1 1116; (Drozdz et al. Nucleic Acids Res. 40(5):2119-30 (2012)), which converts adenine residues to N(6)-methyladenine, thereby protecting against adenine-sensitive restriction enzymes.

In some embodiments, the polynucleotides encoding polypeptide inhibitors and other DNA modification enzymes as described herein can be introduced into the phage or particle genome directly for use in protecting the delivered DNA from the R-M system of the target host bacterium.

Accordingly, in some embodiments, the invention provides a method of increasing the efficiency of introducing a heterologous nucleic acid of interest into a target host bacterium via bacteriophage or transduction particles, comprising introducing at least one heterologous nucleic acid of interest into a phage or particle DNA prior to introduction of a production bacterium, wherein the production host bacterium has been modified to disrupt at least one enzyme of an endogenous R-M system and/or to comprise a polynucleotide encoding at least one heterologous methyltransferase, thereby methylating said phage or particle DNA and producing phage or particle DNA comprising the at least one heterologous nucleic acid of interest having a modified methylation pattern (as compared to phage or particle DNA produced in a production bacterium without said altered methylating activity); producing a phage or particle comprising said recombinant DNA comprising the at least one heterologous nucleic acid of interest; and infecting a target host bacterium with said bacteriophage or particle, wherein the target host bacterium has a methylation pattern (or R-M system(s)) that is identical, similar to or substantially similar to that of the production bacterium, thereby increasing the efficiency of introducing said heterologous nucleic acid of interest into said target host bacterium as compared to introducing said heterologous nucleic acid of interest using a bacteriophage grown in a control production bacterium (wherein the control production host bacterium has not had its methylation activity altered to be identical, similar or substantially similar with that of the target host bacterium). In some aspects, the production bacterium can be modified to alter its R-M system (e.g., disrupt at least one enzyme of an endogenous R-M system and/or to comprise a polynucleotide encoding at least one heterologous methyl transferase) after infection by the phage or particle.

In some embodiments a method of increasing the efficiency of introducing a heterologous nucleic acid of interest into a target host bacterium via a phage or transduction particle is provided, comprising: infecting a production bacterium with a bacteriophage or particle comprising DNA comprising at least one heterologous nucleic acid of interest, wherein the production bacterium has altered methylating activity via disruption of at least one enzyme of an endogenous R-M system and/or expression of at least one heterologous methyltransferase, thereby methylating said DNA; producing a bacteriophage particle comprising bacteriophage or particle DNA having a modified methylation pattern and comprising/encoding the at least one heterologous nucleic acid of interest; and infecting a target host bacterium with said bacteriophage or particle, wherein the target host bacterium has a methylation pattern (or R-M system(s)) that is identical, similar or substantially similar with that of the production host bacterium, thereby increasing the efficiency of introducing said heterologous nucleic acid of interest into said target host bacterium as compared to introducing said heterologous nucleic acid of interest using a bacteriophage or particle produced in a control production bacterium (wherein the control production bacterium has not had its methylation activity altered to be identical, similar substantially similar to that of the target host bacterium as described herein). In some aspects, the production bacterium can be modified to alter its R-M system (e.g., disrupt at least one enzyme of an endogenous R-M system and/or to comprise a polynucleotide encoding at least one heterologous methyltransferase) after infection by the bacteriophage or particle.

In an example, the target host bacterium is chosen on the basis of having a DNA methylation pattern substantially similar to a production host bacterium's restriction-modification system(s) (R-M system).

A methylation pattern is determined by the type of methylation (e.g. m4C) present in the bacterium as well as the particular sequence that is methylated (e.g. GmATC). Thus, the level of similarity (whether it is natural or the result of modifications) between methylation patterns refers to the frequency by which target sites having the appropriate type of methylation. Thus, a substantially similar methylation pattern means having at least about 20% or greater similarity (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or more, or any range or value therein) between the target sites having the appropriate type of methylation as described herein. Thus, in some embodiments, a methylation pattern can be between about 20% to 99% or more similar, about 30% to 99% or more % similar, about 40% to 99% or more similar, about 50% to 99% or more similar, about 60% to 99% or more similar, about 70% to 99% or more similar, about 80% to 99% or more similar, about 85% to 99% or more similar, about 90% to 99% or more similar, or about 95% to 99% or more similar, between host and target bacteria. Substantial similarity between methylation patterns of a target host bacterium and the introduced DNA (bacteriophage or particle DNA that has been modified) means that the introduced DNA is less degraded than that of an introduced DNA that does not share a substantially similar methylation pattern with the target host bacterium. In some embodiments, the methylation pattern of a production bacterium and a target bacterium can be identical.

In some embodiments, the invention provides a bacteriophage or particle comprising DNA that comprise a modified DNA methylation pattern that is identical, similar or substantially similar to a target host bacterium's R-M system(s) and wherein at least one heterologous nucleic acid of interest is integrated into the bacteriophage or particle DNA (genome). Thus, for example, a bacteriophage or transduction particle DNA having a modified methylation pattern (that is substantially similar to a target host bacterium's R-M system(s)) can comprise (1) a polynucleotide encoding a CRISPR array or (2) a Type II CRISPR-Cas system comprising: (a) a polynucleotide encoding a Cas9 polypeptide; (b) a polynucleotide encoding a CRISPR array; and/or c) a tracr nucleic acid. In some embodiments, the polynucleotide encoding a CRISPR array (a) and the tracr nucleic acid (c) can be fused to one another. In additional embodiments, a bacteriophage or particle DNA having a modified methylation pattern (that is identical, similar or substantially similar to a target host bacterium's R-M system(s)) can comprise (1) a polynucleotide encoding a CRISPR array or (2) a recombinant Type I CRISPR-Cas system comprising: (a) a polynucleotide encoding a CRISPR array; and/or (b) at least one polynucleotide encoding one or more Type I CRISPR polypeptides. In some embodiments, the at least one heterologous nucleic acid of interest can be integrated into the bacteriophage or particle DNA (e.g., genome) at a dispensable site of integration or at a complemented site of integration.

As used herein, "dispensable site" means a site in the DNA or genome that is not necessary for maintenance of the bacteriophage or particle genome, the generation of phage or particles, and the delivery of packaged DNA. Thus, any site in a bacteriophage or particle genome that is not required for carrying out such functions can be used as a "landing" site for integrating a nucleic acid of interest. Some exemplary dispensable sites include, but are not limited to, (a) a phage-encoded restriction-modification system (e.g., res/mod in P1 phage), (b) a gene that blocks superinfection (e.g., simABC), (c) an inhibitor of a restriction-modification system (e.g., darA in P1 phage), (d) an insertion sequence element (e.g., IS1 in P1 phage), (e) an addiction system (e.g., phd/doc in P1 phage) or (f) any combination thereof.

A "complemented site" or a "complementable site" as used herein means an
  indispensible site in the bacteriophage or particle DNA or genome that is necessary for maintenance of the bacteriophage or particle genome, the generation of phage or particles, and the delivery of packaged DNA but which can be complemented by a complementing polynucleotide encoding the nucleic acid that is disrupted by the integration (complemented site of integration) of the nucleic acid of interest. The complementing polynucleotide can be integrated into the genome of the production bacterium or it can be comprised on a plasmid in the production bacterium. Accordingly, when the nucleic acid of interest is integrated into a complemented site of a bacteriophage or particle DNA, the production bacterium can comprise on a plasmid or in its genome a polynucleotide encoding a complement to the complemented site in the bacteriophage or particle DNA. Exemplary complemented sites can include, but are not limited to, (a) an activator of the lytic cycle (e.g., coi in P1 phage), (b) a lytic gene (e.g., kilA in P1 phage), (c) a tRNA (e.g., tRNA1,2 in P1 phage), (d) a particle component (e.g., cixL and cixR tail fiber genes in P1 phage), or (e) any combination thereof.

In an embodiment, the methylation pattern of a production strain, such as *Escherichia coli* MG1655 or *Bacillus subtilis* 168, is altered by deleting its endogenous restriction-modification systems and introducing heterologous methyltransferase genes as follows. The restriction-modification genes are identified through means that are known in the art, such as through the online REBASE database (Roberts et al. Nucleic Acids Res 43:D298-D299. doi.org/10.1093/nar/gku1046). These restriction-modification systems can be deleted using standard recombineering strategies known in the art. Once deleted, foreign methyltransferase genes are inserted into replicative plasmids or recombineered into the host genome under the control of a constitutive or inducible promoter. These genes are obtained directly from the target strain using the natural sequence or a sequence codon-optimized for the production host. Alternatively, heterologous methyltransferase genes can be used to confer a similar methylation patterns as the target strain. The methylation patterns conferred by individual methyltransferases are then assessed using established DNA sequencing technologies such as PacBio SMRT sequencing (O'Loughlin et al. PLoS One. 2015:e0118533.). Once generated, the production strain is used to produce bacteriophage or transduction particles for DNA delivery into the target host strain.

Promoters:

Promoters can include, for example, constitutive, inducible, temporally regulated, developmentally regulated, chemically regulated promoters for use in the preparation of recombinant nucleic acid constructs, polynucleotides, expression cassettes and vectors comprising the polynucleotides and recombinant nucleic acid constructs of the invention. These various types of promoters are known in the art.

Thus, in some embodiments, expression herein according to the invention can be made constitutive, inducible, temporally regulated, developmentally regulated, chemically regulated promoters using the recombinant nucleic acid constructs of the invention operatively linked to the appropriate promoter functional in an organism of interest. In representative embodiments, repression can be made reversible using the recombinant nucleic acid constructs of the invention operatively linked to, for example, an inducible promoter functional in an organism of interest.

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Exemplary promoters include useful with this invention include promoters functional in bacteria. A promoter useful with bacteria can include, but is not limited to, L-arabinose inducible (araBAD, $P_{BAD}$) promoter, any lac promoter, L-rhamnose inducible (rhaP$_B$AD) promoter, T7 RNA polymerase promoter, trc promoter, tac promoter, lambda phage promoter ($P_L$,$P_L$-9G-50), anhydrotetracycline-inducible (tetA) promoter, trp, lpp, phoA, recA, proU, cst-1, cadA, nar, lpp-lac, cspA, T7-lac operator, T3-lac operator, T4 gene 32, T5-lac operator, nprM-lac operator, Vhb, Protein A, corynebacterial-*E. coli* like promoters, thr, hom, diphtheria toxin promoter, sig A, sig B, nusG, SoxS, katb, alpha-amylase (Pamy), Ptms, P43 (comprised of two overlapping RNA polymerase a factor recognition sites, σA, σB), Ptms, P43, rplK-rplA, ferredoxin promoter, and/or xylose promoter. (See, K. Terpe Appl. Microbiol, Biotechnol. 72:211-222 (2006); Hannig et al. Trends in Biotechnology 16:54-60 (1998); and Srivastava Protein Expr Purif 40:221-229 (2005)).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the RNAs and/or the polypeptides of the invention to be synthesized only when, for example, an organism is treated with the inducing chemicals. Depending upon the objective, the promoter may be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya et al. 2005. Nature 438:441-442).

Statements

By way of illustration, the invention provides the following Statements.

1. A method of producing a population of phage, wherein the phage are of a first type capable of infecting cells of a first bacterial species or strain (host cells) by binding a cell-surface receptor comprised by bacteria of said species or strain, the method comprising
    (a) Providing a population of second cells comprising the receptor on the surface thereof, wherein the second cells are of a second species or strain, wherein the second species or strain is different from the first species or strain;
    (b) Infecting the second cells with phage of said first type;
    (c) Propagating the phage in the second cells, thereby producing the population of phage; and
    (d) Optionally isolating phage of said population.

Preferably, the second cells are bacterial cells. Alternatively, the second cells are archaeal cells; eukaryotic cells, yeast cells, CHO cells or HEK293 cells.

In an embodiment, the receptor comprises a protein that is encoded by an expressible exogenous nucleotide sequence (ie a non wild-type sequence of the second bacteria), wherein the exogenous sequence is comprises by the genome of the second bacteria. For example, the nucleotide sequence is identical to or at least 85, 90, 95 or 98% identical to a nucleotide sequence comprised by host cells.

In another embodiment, the receptor comprises a sugar moiety that is produced by the action of one or more enzymes in the second bacteria, wherein the genome of the second bacteria comprise one or more expressible exogenous nucleotide sequences (ie a non wild-type sequence of the second bacteria) encoding one or more of the enzyme(s). For example, each nucleotide sequence is identical to or at least 85, 90, 95 or 98% identical to a nucleotide sequence comprised by host cells.

Optionally, the second species or strain do not naturally express the receptor. The host and/or second cells may be engineered cells. The host and/or second cells may be non-naturally-occurring bacterial cells. The host and/or second cells may be non-wild-type cells.

Optionally the host cells comprise an expressible exogenous nucleotide sequence (eg, chromosomally integrated) encoding the receptor.

In an alternative, instead of infecting the second cells with the phage in step (b), phage-encoding DNA is introduced by other means into the second cells, eg, by electroporation. In an example, step (c) comprises culturing the second cells, eg, in a culture vessel, such as a steel fermentation tank.

The second cells comprise cellular machinery operable to replicate DNA encoding the phage.

In an example, the host cells are pathogenic to humans (eg, the host cells are *C difficile* cells) and/or the second cells are non-pathogenic to humans or are cells of a gut commensal species (eg, the second cells are *Lactobacillus* cells, such as *L lactis* or *reuteri* cells). For example, the second cells are carrier cells, eg, as described in US20160333348 (this specific disclosure being incorporated herein by reference). In an example, the invention provides a method of treating or preventing a host cell infection in a human or animal subject (eg, an infection of the gut of the subject), the method comprising administering a population of said second cells to the subject (eg, to populate the gut of the subject) wherein the cells are carrier cells comprising said phage (eg, prophage) of the first type, wherein the phage encode cRNAs or gRNAs that target a protospacer sequence in host cells comprised by the subject (eg, host cells comprised by the gut of the subject), wherein the second cells are carriers for phage that infect host cells in the subject, wherein phage nucleic acid encoding said crRNAs or gRNAs are produced in host cells thereby forming an active CRISPR/Cas system in the host cells, whereby Cas is guided by the crRNAs or gRNAs to a protospacer sequence comprised by the host cells genome to modify (eg, cut) host cell DNA thereby killing host cells or inhibiting host cell growth or proliferation, whereby the infection is treated or prevented. In an embodiment, such a method is for treating or preventing a disease or condition of the subject, wherein the disease or condition is associated or caused by the host cell infection, whereby the disease or condition is treated or prevented. The host cells and/or the second cells can be any such cells disclosed herein.

2. The method of Statement 1, wherein the phage comprise a nucleotide sequence encoding crRNAs (or single guide RNAs) that are operable with Cas (and tracrRNA where necessary) in bacteria of said host cell strain or species to form an active CRISPR/Cas system that is capable of targeting one or more protospacer nucleotide sequences, wherein each target sequence is comprised by the genome of said host cells, whereby the crRNAs (or gRNAs) guide Cas in host cells to modify (eg, cut) the target sequence(s), thereby killing host cells or reducing host cell population growth.

In an example, the phage comprise a HM-array or gRNA-encoding nucleotide sequence as disclosed in US20160333348, the specific disclosure of which is incorporated herein by reference.

3. The method of Statement 2, wherein when infected by the phage, the second cells do not comprise said active CRISPR/Cas system.

For example, one or more Cas is repressed, inactivated or knocked-out in the second cells, wherein the second cells comprise a defective CRISPR/Cas system that is not operable with the crRNAs or gRNAs.

In an example, the active CRISPR/Cas system is as disclosed in US20160333348, the specific disclosure of which is incorporated herein by reference.

4. The method of Statement 2 or 3, wherein the genome of each second bacterial cell does not comprise a said target sequence.

In an example, the target sequence is as disclosed in US20160333348, the specific disclosure of which is incorporated herein by reference.

5. The method of any one of Statements 2 to 4, wherein
    (a) Cas (eg, Cas3, 9, cpf1 and/or CASCADE Cas) of said second cells is not operable with said crRNAs (or gRNAs);
    (b) tracrRNA of said second cells is not operable with said crRNAs; and/or
    (c) said second cells are not operable to produce said crRNAs from said crRNA-encoding nucleotide sequence (or are not operable to produce said gRNAs from said gRNA-encoding nucleotide sequence).

6. The method of any one of Statements 2 to 5, wherein the crRNAs (or gRNAs) comprise repeat sequences that are not operable with Cas of the second cells (eg, Cas3, 9, cpf1 and/or CASCADE Cas of the second cells).

In an example, the repeat(s) is (are) as disclosed in US20160333348, the specific disclosure of which is incorporated herein by reference.

7. The method of any one of Statements 2 to 6, wherein said phage nucleotide sequence is operably connected with a promoter for transcription of crRNAs (or gRNAs) in bacteria of said host species or strain, but not in said second species or strain.

In an example, the promoter is constitutively active in the second cells.

8. The method of any preceding Statement, wherein bacteria of said host species or strain comprise an anti-phage toxin or mechanism for killing or reducing the propagation of phage of said first type that infect host bacteria, wherein the second bacteria do not comprise said toxin or mechanism.

9. The method of any preceding Statement, wherein bacteria of said host species or strain comprise a CRISPR/Cas system that is active for killing or reducing the propagation of phage of said first type that infect host bacteria, wherein the second bacteria do not comprise said system.

10. The method of any preceding Statement, wherein the second bacterial cells are engineered to produce the receptor, wherein wild-type bacteria of said second species or strain do not produce said receptor.

11. The method of any preceding Statement, wherein the phage comprise an origin of replication that is operable in said second cells and in cells of said first species or strain.

12. The method of any preceding Statement, wherein the second cells are *E coli* cells.

For example, the second cells are not pathogenic to humans. For example, the second cells are Hazard Group 1 or 2 cells (eg, such of a species noted as Group 2 in the table herein).

13. The method of any preceding Statement, wherein the first and second cells are of the same species (eg, *E coli* strains).

For example, the second cells are engineered versions of the host cells, eg, wherein the second cells comprise a defective CRISPR/Cas system as mentioned herein and/or do not comprise a said protospacer sequence and/or do not express a toxin that is expressed by host cells.

14. The method of Statement 13, wherein the strain of host cells is a human pathogenic strain (eg, *C difficile*) and the second cell strain is not human pathogenic strain (eg, a *Lactobacillus*, such as *L reuteri* or *lactis*).

15. The method of any preceding Statement, wherein the second cells are cells of a lower hazard category (eg, Hazard Group 1 or 2) compared to cells of the host species or strain (eg, Hazard Group 3 or 4). See Tables 5 and 6.

16. The method of any preceding Statement, wherein the receptor is selected from lipopolysaccharides, teichoic acids (eg, a ManNAc($\beta1\rightarrow4$)GlcNAc disaccharide with one to three glycerol phosphates attached to the C4 hydroxyl of the ManNAc residue followed by a long chain of glycerol- or ribitol phosphate repeats), proteins and flagella.

17. The method of any preceding Statement, wherein the receptor comprises an O-antigen of the host cells.

18. The method of any preceding Statement, wherein the phage are operable to express an endolysin or holin in second cells, eg, when phage replicate in second cells.

19. A cell (propagator cell) for propagating phage, wherein the phage are of a first type capable of infecting cells of a first bacterial species or strain (host cells) by binding a cell-surface receptor comprised by bacteria of said species or strain, the propagator cell comprising the receptor on the surface thereof, wherein the propagator cell is of a second species or strain, wherein the second species or strain is different from the first species or strain, whereby the propagator cell is capable of being infected by phage of said first type for propagation of phage therein.

In an example, the genome of the propagator cell (second cell in the method of the invention) comprises an exogenous nucleotide sequence that encodes the receptor, wherein wild-type cells of the species or strain of the cell do not comprise said nucleotide sequence.

20. The propagator cell of Statement 19, wherein the receptor comprises a protein that is encoded by an expressible nucleotide sequence comprised by the genome of the propagator cell, wherein wild-type cells of the same species or strain as the propagator cell do not comprise said expressible nucleotide sequence.

21. The propagator cell of Statement 19, wherein the receptor comprises a sugar moiety that is the product of the action of one or more enzymes in the propagator cell, wherein the genome of the propagator cell comprises one or expressible nucleotide sequences encoding said one or more enzymes, wherein wild-type cells of the same species or strain as the propagator cell do not comprise said expressible nucleotide sequence(s).

22. The propagator cell of Statement 19, wherein the receptor comprises a teichoic acid moiety that is the product of the action of one or more enzymes in the propagator cell, wherein the genome of the propagator cell comprises one or expressible nucleotide sequences encoding said one or more enzymes, wherein wild-type cells of the same species or strain as the propagator cell do not comprise said expressible nucleotide sequence(s).

23. The propagator cell of Statement 22, wherein the enzyme(s) are selected from TarO, TarA, TarB, TarF, TarK, and TarL (or a homologue thereof expressed by cells of the host and/or second cells).

24. The propagator cell of any one of Statements 19 to 23 in combination with phage of said first type.
25. The propagator cell of any one of Statements 19 to 24, wherein the cell comprises one or more prophage of said first type (eg, chromosomally integrated in the propagator cell).
26. The propagator cell of any one of Statements 19 to 25, wherein the propagator cell is a gram-negative bacterial cell and optionally the host cells are gram-negative bacterial cells.
27. The propagator cell of any one of Statements 19 to 25, wherein the propagator cell is a gram-positive bacterial cell and optionally the host cells are gram-positive bacterial cells.
28. A population of propagator cells according to any one of Statements 19 to 27, optionally comprised in a fermentation vessel for culturing the propagator cells and propagating phage of said first type.
29. The propagator cell or population of any one of Statements 19 to 28, wherein each propagator cell is a second cell as defined in any one of Statements 1 to 18.
30. The propagator cell or population of any one of Statements 19 to 28, wherein each host cells is a host cell as defined in any one of Statements 1 to 18.
31. The propagator cell or population of any one of Statements 19 to 28, wherein the phage are phage as defined in any one of Statements 1 to 18.
32. A method of treating or preventing a disease or condition in a human or animal subject, the disease or condition being mediated by host cells comprised by the subject (eg, comprised by the gut of the subject), the method comprising administering propagator cells to the subject (eg, to populate the gut of the subject), wherein the propagator cells are according to any one of Statements 19 to 31, wherein the propagator cells produce phage and phage infect host cells in the patient (eg, in the gut thereof), thereby killing host cells or inhibiting growth or proliferation of host cells in the subject, whereby the disease or condition is treated or prevented.
33. The method of Statement 32, wherein the propagator cells are *Lactobacillus* (eg, *L reuteri*) cells.
34. The method of Statement 32 or 33, wherein the phage encode anti-host cell crRNAs or gRNAs that guide Cas in the host cells to modify (eg, cut) host cell DNA, thereby carrying out said killing or inhibiting.

Concepts

The invention also provides the following Concepts:
1. A method of producing a population of phage, wherein the phage are of a first type capable of infecting cells of a first bacterial species or strain (host cells) by binding a cell-surface receptor comprised by bacteria of said species or strain, the method comprising
   (a) Providing a population of second bacterial cells comprising the receptor on the surface thereof, wherein the second cells are of a second species or strain, wherein the second species or strain is different from the first species or strain;
   (b) Infecting the second cells with phage of said first type;
   (c) Propagating the phage in the second cells, thereby producing the population of phage; and
   (d) Optionally isolating phage of said population.
2. A method of producing a population of transduction particles comprising nucleic acid packaged by phage coat proteins, wherein the particles are capable of infecting cells of a first bacterial species or strain (host cells) by binding a cell-surface receptor comprised by bacteria of said species or strain, whereby host cells are transduced with the nucleic acid, the method comprising
   (a) Providing a population of second bacterial cells comprising the receptor on the surface thereof, wherein the second cells are of a second species or strain, wherein the second species or strain is different from the first species or strain, and wherein the second cells comprise DNA that is capable of producing copies of said nucleic acid;
   (b) Infecting the second cells with phage by binding the phage to the receptor comprised by the second bacterial cells;
   (c) Propagating the phage in the second cells, wherein phage coat proteins are produced that package copies of said nucleic acid, thereby producing the population of particles; and
   (d) Optionally isolating particles of said population.

In an example, the nucleic acid comprised by the particles is DNA. In an example, the nucleic acid is RNA. In an example, the phage used to infect the second cells in step (b) are helper phage, optionally that are different from the transduction particles (when the transduction particles are phage). Optionally, the helper phage are defective for self-replication in the second cells.

For example, the DNA comprised by the second cells is comprised by chromosomal DNA of each second cell. In another example, the DNA is comprised by one or more episomes (eg, plasmids) comprised by each second cell.

"Transduction particles" may be phage or smaller than phage and are particles that are capable of transducing nucleic acid (eg, encoding an antibiotic or component thereof, such as a CRISPR array) into host bacterial cells.

The particles comprise phage coat proteins and optionally other phage structural proteins encoded by the phage used in step (b). Examples of structural proteins are phage proteins selected from one, more or all of the major head and tail proteins, the portal protein, tail fibre proteins, and minor tail proteins.

The particles comprise nucleic acid (eg, DNA, such as DNA encoding the array or antibiotic), wherein the nucleic acid comprises a packaging signal sequence operable with proteins encoded by the phage of step (b) to package the nucleic acid or copies thereof into transduction particles that are capable of infecting host cells.

In an example, each transduction particle is a non-self replicative transduction particle. A "non-self replicative transduction particle" refers to a particle, (eg, a phage or phage-like particle; or a particle produced from a genomic island (eg, a *S aureus* pathogenicity island (SaPI)) or a modified version thereof) capable of delivering a nucleic acid molecule of the particle (eg, encoding an antibacterial agent or component) into a bacterial cell, but does not package its own replicated genome into the transduction particle.

Optionally, the nucleic acid of each particle comprises a modified genomic island. Optionally, the genomic island is an island that is naturally found in bacterial cells of the host species or strain. In an example, the genomic island is selected from the group consisting of a SaPI, a SaPI1, a SaPI2, a SaPIbov1 and a SaPibov2 genomic island. Optionally, the nucleic acid of each particle comprises a modified pathogenicity island. Optionally, the pathogenicity island is an island that is naturally found in bacterial cells of the first species or strain, eg, a *Staphylococcus* SaPI or a Vibro PLE or a *P. aeruginosa* pathogenicity island (eg, a PAPI or a PAGI, eg, PAPI-1, PAGI-5, PAGI-6, PAGI-7, PAGI-8, PAGI-9 or PAGI-10). Optionally, the pathogenicity island is a SaPI (*S aureus* pathogenicity island).

Optionally, the transcription of transduction particle nucleic acid is under the control of an inducible promoter, for transcription of copies of the antibacterial agent or component or array in a host cell. This may be useful, for example, to control switching on of the antibacterial activity or production of anti-host cell crRNAs for use against target bacterial cells, such as in an environment (eg, soil or water) or in an industrial culture or fermentation container containing the target cells. For example, the host cells may be useful in an industrial process (eg, for fermentation, eg, in the brewing or dairy industry) and the induction enables the process to be controlled (eg, stopped or reduced) by using the antibacterial agent or crRNAs against the host bacteria.

3. The method of Concept 2, wherein the particles are non-replicative transduction particles or phage.
4. The method of any preceding Concept, wherein the phage or particles comprise a nucleotide sequence encoding crRNAs (or single guide RNAs) that are operable with Cas in bacteria of said host cell strain or species to form an active CRISPR/Cas system that is capable of targeting one or more protospacer nucleotide sequences, wherein each target sequence is comprised by the genome of said host cells, whereby the crRNAs (or gRNAs) guide Cas in host cells to modify (optionally cut) the target sequence(s), thereby killing host cells or reducing host cell population growth.
5. The method of Concept 4, wherein when infected by the phage, the second cells do not comprise said active CRISPR/Cas system.
6. The method of Concept 4 or 5, wherein the genome of each second bacterial cell does not comprise a said target sequence.
7. The method of any one of Concepts 4 to 6, wherein
   (a) Cas (optionally Cas3, 9, cpf1 and/or CASCADE Cas) of said second cells is not operable with said crRNAs (or gRNAs);
   (b) tracrRNA of said second cells is not operable with said crRNAs; and/or
   (c) said second cells are not operable to produce said crRNAs from said crRNA-encoding nucleotide sequence (or are not operable to produce said gRNAs from said gRNA-encoding nucleotide sequence).
8. The method of any one of Concepts 4 to 7, wherein the crRNAs (or gRNAs) comprise repeat sequences that are not operable with Cas of the second cells (optionally Cas3, 9, cpf1 and/or CASCADE Cas of the second cells).
9. The method of any one of Concepts 4 to 8, wherein said nucleotide sequence is operably connected with a promoter for transcription of crRNAs (or gRNAs) in bacteria of said host species or strain, but not in said second species or strain.
10. The method of any preceding Concept, wherein
    (a) the phage or particles comprise a nucleotide sequence encoding crRNAs (or single guide RNAs) that are operable with Cas in bacteria of said host cell strain or species to form an active CRISPR/Cas system that is capable of targeting one or more protospacer nucleotide sequences, wherein each target sequence is comprised by the genome of said host cells, whereby the crRNAs (or gRNAs) guide Cas in host cells to modify (optionally cut) the target sequence(s), thereby killing host cells or reducing host cell population growth;
    (b) the host and second cells are of the same species (optionally *E coli* strains); and
    (c) the genome of each second bacterial cell does not comprise a said target sequence, wherein the first and second cells are different strains of the same species.
11. The method of any preceding Concept, wherein bacteria of said host species or strain comprise an anti-phage toxin or mechanism for killing or reducing the propagation of phage of said first type or particles that infect host bacteria, wherein the second bacteria do not comprise said toxin or mechanism.
12. The method of any preceding Concept, wherein bacteria of said host species or strain comprise a CRISPR/Cas system that is active for killing or reducing the propagation of phage of said first type or particles that infect host bacteria, wherein the second bacteria do not comprise said system.
13. The method of any preceding Concept, wherein the second bacterial cells are engineered to produce the receptor, wherein wild-type bacteria of said second species or strain do not produce said receptor.
14. The method of any preceding Concept, wherein the phage or particles comprise an origin of replication that is operable in said second cells and in cells of said first species or strain.
15. The method of any preceding Concept, wherein the second cells are *E coli* cells.
16. The method of any preceding Concept, wherein the first and second cells are of the same species (optionally *E coli* strains).
17. The method of Concept 16, wherein the strain of host cells is a human pathogenic strain and the second cell strain is not human pathogenic strain.
18. The method of any preceding Concept, wherein the second cells are cells of a lower hazard category (optionally Hazard Group 1 or 2) compared to cells of the host species or strain (optionally Hazard Group 3 or 4).
19. The method of any preceding Concept, wherein the receptor is selected from lipopolysaccharides, teichoic acids (optionally a ManNAc($\beta1\rightarrow4$)GlcNAc disaccharide with one to three glycerol phosphates attached to the C4 hydroxyl of the ManNAc residue followed by a long chain of glycerol- or ribitol phosphate repeats), proteins and flagella.
20. The method of any preceding Concept, wherein the receptor comprises an O-antigen of the host cells.
21. The method of any preceding Concept, wherein the phage or particles are operable to express an endolysin or holin in second cells, optionally when phage or particles replicate in second cells.
22. A cell (propagator cell) for propagating phage or transduction particles comprising nucleic acid packaged by phage coat proteins, wherein the phage or particles are of a first type capable of infecting cells of a first bacterial species or strain (host cells) by binding a cell-surface receptor comprised by bacteria of said species or strain, the propagator cell comprising the receptor on the surface thereof, wherein the propagator cell is of a second species or strain, wherein the second species or strain is different from the first species or strain, whereby the propagator cell is capable of being infected by phage of said first type or said particles for propagation of phage or particles respectively therein.
23. The propagator cell of Concept 22, wherein the receptor comprises a protein that is encoded by an expressible nucleotide sequence comprised by the genome of the propagator cell, wherein wild-type cells of the same species or strain as the propagator cell do not comprise said expressible nucleotide sequence.
24. The propagator cell of Concept 22, wherein the receptor comprises a sugar moiety that is the product of the action of one or more enzymes in the propagator cell, wherein the genome of the propagator cell comprises one or expressible nucleotide sequences encoding said one or more enzymes, wherein wild-type cells of the same species or strain as the propagator cell do not comprise said expressible nucleotide sequence(s).
25. The propagator cell of Concept 22, wherein the receptor comprises a teichoic acid moiety that is the product of the action of one or more enzymes in the propagator cell, wherein the genome of the propagator cell comprises one or expressible nucleotide sequences encoding said one or more enzymes, wherein wild-type cells of the same species or strain as the propagator cell do not comprise said expressible nucleotide sequence(s).
26. The propagator cell of Concept 25, wherein the enzyme(s) are selected from TarO, TarA, TarB, TarF, TarK, and TarL (or a homologue thereof expressed by cells of the host and/or second cells).
27. The propagator cell of any one of Concepts 22 to 26 in combination with phage of said first type or a said transduction particle.
28. The propagator cell of any one of Concepts 22 to 27, wherein the cell comprises one or more prophage of said first type (optionally chromosomally integrated in the propagator cell) or DNA that is capable of producing copies of said nucleic acid of the transducing particles (optionally chromosomally integrated in the propagator cell).
29. The propagator cell of any one of Concepts 22 to 28, wherein the propagator cell is a gram-negative bacterial cell and optionally the host cells are gram-negative bacterial cells.
30. The propagator cell of any one of Concepts 22 to 28, wherein the propagator cell is a gram-positive bacterial cell and optionally the host cells are gram-positive bacterial cells.
31. A population of propagator cells according to any one of Concepts 22 to 30, optionally comprised in a fermentation vessel for culturing the propagator cells and propagating phage of said first type or said transduction particles.
32. The propagator cell or population of any one of Concepts 22 to 31, wherein each propagator cell is a second cell as defined in any one of Concepts 1 to 21.
33. The propagator cell or population of any one of Concepts 22 to 31, wherein each host cells is a host cell as defined in any one of Concepts 1 to 21.
34. The propagator cell or population of any one of Concepts 22 to 31, wherein the phage or particles are phage or particles as defined in any one of Concepts 1 to 21.
35. A method of treating or preventing a disease or condition in a human or animal subject, the disease or condition being mediated by host cells comprised by the subject (optionally comprised by the gut of the subject), the method comprising administering propagator cells to the subject (optionally to populate the gut of the subject), wherein the propagator cells are according to any one of Concepts 22 to 34, wherein the propagator cells produce phage or transduction partiles and phage or particles respectively infect host cells in the patient (optionally in the gut thereof), thereby killing host cells or inhibiting growth or proliferation of host cells in the subject, whereby the disease or condition is treated or prevented.
36. The method of Concept 35, wherein the propagator cells are *Lactobacillus* (optionally L *reuteri*) cells.
37. The method of Concept 35 or 36, wherein the phage encode anti-host cell crRNAs or gRNAs that guide Cas in the host cells to modify (optionally cut) host cell DNA, thereby carrying out said killing or inhibiting.

Example 1: Engineering of Production Strain to Become Susceptible to Helper Phage Summary:

We engineered a production strain of bacteria (in this case an *E coli* production strain) to express a phage receptor rendering the strain susceptible to infection by a helper phage. The production bacteria harboured a vector containing a CRISPR array and a phage packaging site so that the vector could be packaged in cells that had been infected by the helper (but not in cells that are not so infected), thereby enabling use of the bacteria as a production strain for phage-like particles encoding crRNAs. We further showed that a lysate produced by such production strain contains phage-like particles that could be used to deliver the CRISPR array to other related *E coli* target populations. Here we call the vectors CRISPR Guided Vectors (CGVs™).

Advantageously, to produce CGV-charged phage-like particles (CGV-PLP) targeting a specific bacterial population, it may be beneficial to produce the CGV-PLPs in a strain related to the target strain, for example to produce CGV-PLPs that avoid host defence mechanisms in the target strain. For example, modification of the DNA of CGV-PLPs by methyltransferases in the production bacteria can be useful to shield the DNA against restriction modification once the PLP subsequently infects the target cells where the species or strains of the production and target bacteria are the same or closely related (or at any rate comprise common methyltransferases). By adapting the production strain as per the invention to display a surface receptor, the invention enables PLP production in a strain that may display beneficial DNA modification against restriction modification subsequently by the target bacteria. Usefully, the protospacer sequence(s) to which crRNAs of the PLP are targeted in the target bacteria may be deleted or naturally absent in the genome of the production bacteria, such that Cas-mediated cutting of the production bacteria genomes does not take place during the production of the PLPs.

Methods and Results:

As a production strain, we used the *Escherichia coli* strain MG1655 that was transformed with a plasmid expressing the receptor for helper phage M13KO7 (FIG. 1_X) while a strain line not receiving the receptor (FIG. 1_Y) served as control. The receptor was a F-pilus expressed from the plasmid pCJ105 obtained from New England Biolabs. Both strains were transformed with a CGV (FIG. 1_3) and infected with helper phage M13KO7 for the production of CGV-PLP.

In line X, CGV-PLP lysate was produced due to presence of receptor while in line Y no lysate was produced (FIG. 1_4). The resulting lysate was shown to be able to deliver the CGV to different target populations related to the production strain and harbouring the phage receptor (FIG. 1_5 and FIG.

Figure 2:
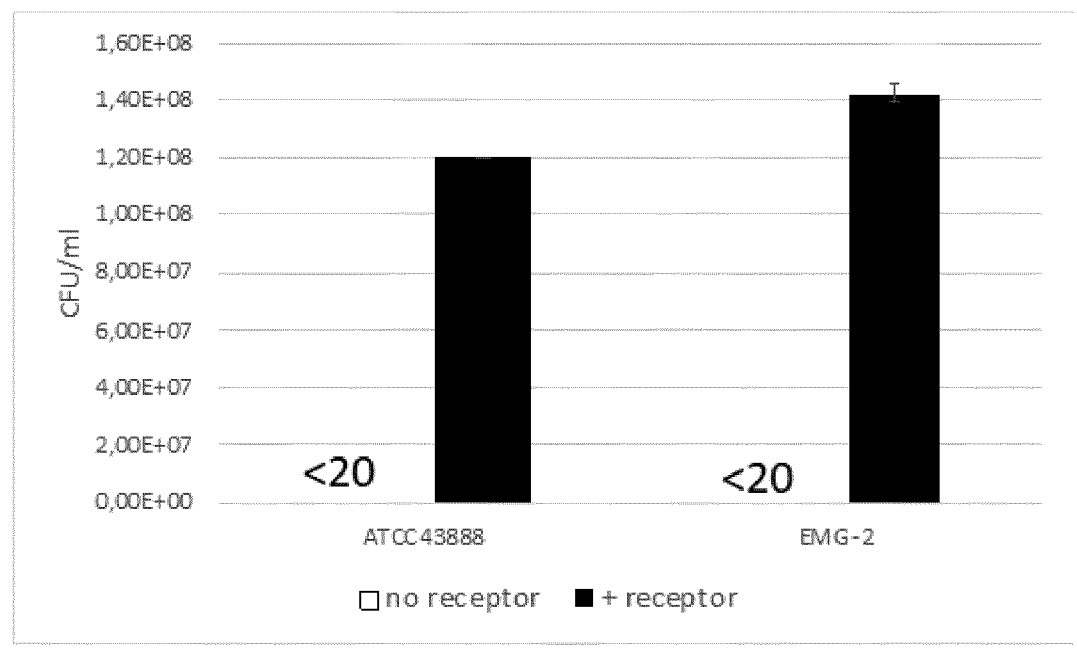

2). The control strain line did not produce CGV-PLP that was able to deliver the CGV to the target population (FIG. 2).

TABLE 5

HAZARD GROUPS

| | |
|---|---|
| Group 1 | Unlikely to cause human disease. |
| Group 2 | Can cause human disease and may be a hazard to employees; it is unlikely to spread to the community and there is usually effective prophylaxis or treatment available. |
| Group 3 | Can cause severe human disease and may be a serious hazard to employees; it may spread to the community, but there is usually effective prophylaxis or treatment available. |
| Group 4 | Causes severe human disease and is a serious hazard to employees; it is likely to spread to the community and there is usually no effective prophylaxis or treatment available. |

TABLE 6

THE APPROVED LIST OF BIOLOGICAL AGENTS (HSE CLASSIFICATION)

| BACTERIA | HAZARD GROUP |
|---|---|
| Arcobacter butzleri (formerly Campylobacter butzleri) | 2 |
| Actinobacillus actinomycetemcomitans | 2 |
| Actinomadura madurae | 2 |
| Actinomadura pelletieri | 2 |
| Actinomyces gerencseriae | 2 |
| Actinomyces israelii | 2 |
| Actinomyces pyogenes | 2 |
| Actinomyces spp | 2 |
| Alcaligenes spp | 2 |
| Arcanobacterium haemolyticum (Corynebacterium haemolyticum) | 2 |
| Arcanobacterium pyogenes (formerly Actinomyces pyogenes) | 2 |
| Bacillus anthracis | 3 |
| Bacillus cereus | 2 |
| Bacteroides fragilis | 2 |
| Bacteroides spp | 2 |
| Bartonella bacilliformis | 2 |
| Bartonella quintana (Rochalimaea quintana) | 2 |
| Bartonella spp (Rochalimaea spp) | 2 |
| Bordetella bronchiseptica | 2 |
| Bordetella parapertussis | 2 |
| Bordetella pertussis | 2 |
| Bordetella spp | 2 |
| Borrelia burgdorferi | 2 |
| Borrelia duttonii | 2 |
| Borrelia recurrentis | 2 |
| Borrelia spp | 2 |
| Brachispira spp (formerly Serpulina spp) | 2 |
| Brucella abortus | 3 |
| Brucella canis | 3 |
| Brucella melitensis | 3 |
| Brucella suis | 3 |
| Burkholderia cepacia | 2 |
| Burkholderia mallei (formerly Pseudomonas mallei) | 3 |
| Burkholderia pseudomallei (formerly Pseudomonas pseudomallei) | 3 |
| Campylobacter fetus | 2 |
| Campylobacter jejuni | 2 |
| Campylobacter spp | 2 |
| Cardiobacterium hominis | 2 |

TABLE 6-continued

THE APPROVED LIST OF BIOLOGICAL AGENTS (HSE CLASSIFICATION)

| BACTERIA | HAZARD GROUP |
|---|---|
| Chlamydophila pneumoniae | 2 |
| Chlamydophila psittaci (avian strains) | 3 |
| Chlamydophila psittaci (non-avian strains) | 2 |
| Chlamydophila trachomatis | 2 |
| Clostridium botulinum | 2 |
| Clostridium perfringens | 2 |
| Clostridium spp | 2 |
| Clostridium tetani | 2 |
| Corynebacterium diphtheriae | 2 |
| Corynebacterium haemolyticum | 2 |
| Corynebacterium minutissimum | 2 |
| Corynebacterium pseudotuberculosis | 2 |
| Corynebacterium pyogenes | 2 |
| Corynebacterium spp | 2 |
| Corynebacterium ulcerans | 2 |
| Coxiella burnetti | 3 |
| Edwardsiella tarda | 2 |
| Ehrlichia sennetsu (Rickettsia sennetsu) | 3 |
| Ehrlichia spp | 2 |
| Eikenella corrodens | 2 |
| Elizabethkingia meningoseptica (formerly Flavobacterium meningosepticum) | 2 |
| Enterobacter aerogenes/cloacae | 2 |
| Enterobacter spp | 2 |
| Enterococcus spp | 2 |
| Erysipelothrix rhusiopathiae | 2 |
| Escherichia coli (with the exception of non-pathogenic strains) | 2 |
| Escherichia coli, verocytotoxigenic strains (eg O157:H7 or O103) | 3 |
| Flavobacterium meningosepticum | 2 |
| Fluoribacter bozemanae (formerly Legionella) | 2 |
| Francisella tularensis (Type A) | 3 |
| Francisella tularensis (Type B) | 2 |
| Fusobacterium necrophorum | 2 |
| Fusobacterium spp | 2 |
| Gardnerella vaginalis | 2 |
| Haemophilus ducreyi | 2 |
| Haemophilus influenzae | 2 |
| Haemophilus spp | 2 |
| Helicobacter pylori | 2 |
| Klebsiella oxytoca | 2 |
| Klebsiella pneumoniae | 2 |
| Klebsiella spp | 2 |
| Legionella pneumophila | 2 |
| Legionella spp | 2 |
| Leptospira interrogans (all serovars) | 2 |
| Listeria ivanovii | 2 |
| Listeria monocytogenes | 2 |
| Moraxella catarrhalis | 2 |
| Morganella morganii | 2 |
| Mycobacterium africanum | 3 |
| Mycobacterium avium/intracellulare | 2 |
| Mycobacterium bovis | 3 |
| Mycobacterium bovis (BCG strain) | 2 |
| Mycobacterium chelonae | 2 |
| Mycobacterium fortuitum | 2 |
| Mycobacterium kansasii | 2 |
| Mycobacterium leprae | 3 |
| Mycobacterium malmoense | 3 |
| Mycobacterium marinum | 2 |
| Mycobacterium microti | 3 |
| Mycobacterium paratuberculosis | 2 |
| Mycobacterium scrofulaceum | 2 |
| Mycobacterium simiae | 2 |
| Mycobacterium szulgai | 3 |
| Mycobacterium tuberculosis | 3 |
| Mycobacterium ulcerans | 3 |
| Mycobacterium xenopi | 2 |
| Mycoplasma caviae | 2 |

TABLE 6-continued

THE APPROVED LIST OF BIOLOGICAL
AGENTS (HSE CLASSIFICATION)

| BACTERIA | HAZARD GROUP | |
|---|---|---|
| Mycoplasma hominis | 2 | |
| Mycoplasma pneumoniae | 2 | |
| Neisseria gonorrhoeae | 2 | |
| Neisseria meningitidis | 2 | |
| Nocardia asteroids | 2 | |
| Nocardia braziliensis | 2 | |
| Nocardia farcinica | 2 | |
| Nocardia nova | 2 | |
| Nocardia otitidiscaviarum | 2 | |
| Pasteurella multocida | 2 | |
| Pasteurella spp | 2 | |
| Peptostreptococcus anaerobius | 2 | |
| Peptostreptococcus spp | 2 | |
| Plesiomonas shigelloides | 2 | |
| Porphyromonas spp | 2 | |
| Prevotella spp | 2 | |
| Proteus mirabilis | 2 | |
| Proteus penneri | 2 | |
| Proteus vulgaris | 2 | |
| Providencia alcalifaciens | 2 | |
| Providencia rettgeri | 2 | |
| Providencia spp | 2 | |
| Pseudomonas aeruginosa | 2 | |
| Pseudomonas mallei | 3 | |
| Pseudomonas pseudomallei | 3 | |
| Rhodococcus equi | 2 | |
| Rickettsia akari | 3 | |
| Rickettsia canada | 3 | |
| Rickettsia conorii | 3 | |
| Rickettsia montana | 3 | |
| Rickettsia mooseri | 3 | |
| Rickettsia prowazekii | 3 | |
| Rickettsia rickettsii | 3 | |
| Rickettsia sennetsu | 3 | |
| Rickettsia spp | 3 | |
| Rickettsia tsutsugamushi | 3 | |
| Rickettsia typhi (Rickettsia mooseri) | 3 | |
| Rochalimaea quintana | 2 | |
| Rochalimaea spp | 2 | |
| Salmonella arizonae | 2 | |
| Salmonella enterica serovar enteritidis | 2 | |
| Salmonella enterica serovar typhimurium 2 | 2 | |
| Salmonella paratyphi A | 3 | |
| Salmonella paratyphi B/java | 3 | |
| Salmonella paratyphi C/Choleraesuis | 3 | |
| Salmonella spp | 2 | Serovars other than arizonae, enterica serovar enteritidis, enterica serovar typhimurium 2, paratyphi A, B, C, typhi |
| Salmonella typhi | 3 | Serovars arizonae, enterica serovar enteritidis, enterica serovar typhimurium 2, paratyphi A, B, C, typhi |
| Serpulina spp | 2 | |
| Shigella boydii | 2 | |
| Shigella dysenteriae (other than Type 1) | 2 | |
| Shigella dysenteriae (Type 1) | 3 | |
| Shigella flexneri | 2 | |
| Shigella sonnei | 2 | |
| Staphylococcus aureus | 2 | |
| Streptobacillus moniliformis | 2 | |
| Streptococcus agalactiae | 2 | |
| Streptococcus dysgalactiaeequisimilis | 2 | |
| Streptococcus pneumoniae | 2 | |
| Streptococcus pyogenes | 2 | |
| Streptococcus spp | 2 | |
| Streptococcus suis | 2 | |
| Treponema carateum | 2 | |
| Treponema pallidum | 2 | |
| Treponema pertenue | 2 | |
| Treponema spp | 2 | |
| Ureaplasma parvum | 2 | |
| Ureaplasma urealyticum | 2 | |
| Vibrio cholerae (including El Tor) | 2 | |
| Vibrio parahaemolyticus | 2 | |
| Vibrio spp | 2 | |
| Yersinia enterocolitica | 2 | |
| Yersinia pestis | 3 | |
| Yersinia pseudotuberculosis | 2 | |
| Yersinia spp | 2 | |

TABLE 7

Example Bacteria

Abiotrophia

*Abiotrophia defectiva*
Acaricomes

*Acaricomes phytoseiuli*
Acetitomaculum

*Acetitomaculum ruminis*
Acetivibrio

*Acetivibrio cellulolyticus*
*Acetivibrio ethanolgignens*
*Acetivibrio multivorans*
Acetoanaerobium

*Acetoanaerobium noterae*
Acetobacter

*Acetobacter aceti*
*Acetobacter cerevisiae*
*Acetobacter cibinongensis*
*Acetobacter estunensis*
*Acetobacter fabarum*
*Acetobacter ghanensis*
*Acetobacter indonesiensis*
*Acetobacter lovaniensis*
*Acetobacter malorum*
*Acetobacter nitrogenifigens*
*Acetobacter oeni*
*Acetobacter orientalis*
*Acetobacter orleanensis*
*Acetobacter pasteurianus*
*Acetobacter pomorum*
*Acetobacter senegalensis*
*Acetobacter xylinus*
Acetobacterium

*Acetobacterium bakii*
*Acetobacterium carbinolicum*
*Acetobacterium dehalogenans*
*Acetobacterium fimetarium*
*Acetobacterium malicum*
*Acetobacterium paludosum*
*Acetobacterium tundrae*
*Acetobacterium wieringae*
*Acetobacterium woodii*
Acetofilamentum

*Acetofilamentum rigidum*

TABLE 7-continued

| Example Bacteria |
|---|
| Acetohalobium |
| *Acetohalobium arabaticum* |
| Acetomicrobium |
| *Acetomicrobium faecale* |
| *Acetomicrobium flavidum* |
| Acetonema |
| *Acetonema longum* |
| Acetothermus |
| *Acetothermus paucivorans* |
| Acholeplasma |
| *Acholeplasma axanthum* |
| *Acholeplasma brassicae* |
| *Acholeplasma cavigenitalium* |
| *Acholeplasma equifetale* |
| *Acholeplasma granularum* |
| *Acholeplasma hippikon* |
| *Acholeplasma laidlawii* |
| *Acholeplasma modicum* |
| *Acholeplasma morum* |
| *Acholeplasma multilocale* |
| *Acholeplasma oculi* |
| *Acholeplasma palmae* |
| *Acholeplasma parvum* |
| *Acholeplasma pleciae* |
| *Acholeplasma vituli* |
| Achtomobacter |
| *Achtomobacter denitrificans* |
| *Achtomobacter insolitus* |
| *Achtomobacter piechaudii* |
| *Achtomobacter ruhlandii* |
| *Achtomobacter spanius* |
| Acidaminobacter |
| *Acidaminobacter hydrogenoformans* |
| Acidaminococcus |
| *Acidaminococcus fermentans* |
| *Acidaminococcus intestini* |
| Acidicaldus |
| *Acidicaldus organivorans* |
| Acidimicrobium |
| *Acidimicrobium ferrooxidans* |
| Acidiphilium |
| *Acidiphilium acidophilum* |
| *Acidiphilium angustum* |
| *Acidiphilium cryptum* |
| *Acidiphilium multivorum* |
| *Acidiphilium organovorum* |
| *Acidiphilium rubrum* |
| Acidisoma |
| *Acidisoma sibiricum* |
| *Acidisoma tundrae* |
| Acidisphaera |
| *Acidisphaera rubrifaciens* |
| Acidithiobacillus |
| *Acidithiobacillus albertensis* |
| *Acidithiobacillus caldus* |
| *Acidithiobacillus ferrooxidans* |
| *Acidithiobacillus thiooxidans* |
| Acidobacterium |
| *Acidobacterium capsulatum* |

TABLE 7-continued

| Example Bacteria |
|---|
| Acidocella |
| *Acidocella aminolytica* |
| *Acidocella facilis* |
| Acidomonas |
| *Acidomonas methanolica* |
| Acidothermus |
| *Acidothermus cellulolyticus* |
| Acidovorax |
| *Acidovorax anthurii* |
| *Acidovorax caeni* |
| *Acidovorax cattleyae* |
| *Acidovorax citrulli* |
| *Acidovorax defluvii* |
| *Acidovorax delafieldii* |
| *Acidovorax facilis* |
| *Acidovorax konjaci* |
| *Acidovorax temperans* |
| *Acidovorax valerianellae* |
| Acinetobacter |
| *Acinetobacter baumannii* |
| *Acinetobacter baylyi* |
| *Acinetobacter bouvetii* |
| *Acinetobacter calcoaceticus* |
| *Acinetobacter gerneri* |
| *Acinetobacter haemolyticus* |
| *Acinetobacter johnsonii* |
| *Acinetobacter junii* |
| *Acinetobacter lwoffi* |
| *Acinetobacter parvus* |
| *Acinetobacter radioresistens* |
| *Acinetobacter schindleri* |
| *Acinetobacter soli* |
| *Acinetobacter tandoii* |
| *Acinetobacter tjernbergiae* |
| *Acinetobacter towneri* |
| *Acinetobacter ursingii* |
| *Acinetobacter venetianus* |
| Acrocarpospora |
| *Acrocarpospora corrugata* |
| *Acrocarpospora macrocephala* |
| *Acrocarpospora pleiomorpha* |
| Actibacter |
| *Actibacter sediminis* |
| Actinoalloteichus |
| *Actinoalloteichus cyanogriseus* |
| *Actinoalloteichus hymeniacidonis* |
| *Actinoalloteichus spitiensis* |
| Actinobacillus |
| *Actinobacillus capsulatus* |
| *Actinobacillus delphinicola* |
| *Actinobacillus hominis* |
| *Actinobacillus indolicus* |
| *Actinobacillus lignieresii* |
| *Actinobacillus minor* |
| *Actinobacillus muris* |
| *Actinobacillus pleuropneumoniae* |
| *Actinobacillus porcinus* |
| *Actinobacillus rossii* |
| *Actinobacillus scotiae* |
| *Actinobacillus seminis* |
| *Actinobacillus succinogenes* |
| *Actinobacillus suis* |
| *Actinobacillus ureae* |

TABLE 7-continued

Example Bacteria

Actinobaculum

Actinobaculum massiliense
Actinobaculum schaalii
Actinobaculum suis
Actinomyces urinale
Actinocatenispora Actinocatenispora rupis
Actinocatenispora thailandica
Actinocatenispora sera
Actinocorallia Actinocorallia aurantiaca
Actinocorallia aurea
Actinocorallia cavernae
Actinocorallia glomerata
Actinocorallia herbida
Actinocorallia libanotica
Actinocorallia longicatena
Actinomadura Actinomadura alba
Actinomadura atramentaria
Actinomadura bangladeshensis
Actinomadura catellatispora
Actinomadura chibensis
Actinomadura chokoriensis
Actinomadura citrea
Actinomadura coerulea
Actinomadura echinospora
Actinomadura fibrosa
Actinomadura formosensis
Actinomadura hibisca
Actinomadura kijaniata
Actinomadura latina
Actinomadura livida
Actinomadura luteofluorescens
Actinomadura macra
Actinomadura madurae
Actinomadura oligospora
Actinomadura pelletieri
Actinomadura rubrobrunea
Actinomadura rugatobispora
Actinomadura umbrina
Actinomadura verrucosospora
Actinomadura vinacea
Actinomadura viridilutea
Actinomadura viridix
Actinomadura yumaensis
Actinomyces Actinomyces denticolens
Actinomyces europaeus
Actinomyces bovis
Actinomyces georgiae
Actinomyces gerencseriae
Actinomyces hordeovulneris
Actinomyces howellii
Actinomyces hyovaginalis
Actinomyces israelii
Actinomyces johnsonii
Actinomyces meyeri
Actinomyces naeslundii
Actinomyces neuii
Actinomyces odontolyticus
Actinomyces oris
Actinomyces radingae
Actinomyces slackii
Actinomyces turicensis
Actinomyces viscosus TABLE 7-continued Example Bacteria Actinoplanes Actinoplanes auranticolor
Actinoplanes brasiliensis
Actinoplanes consettensis
Actinoplanes deccanensis
Actinoplanes derwentensis
Actinoplanes digitatis
Actinoplanes durhamensis
Actinoplanes ferrugineus
Actinoplanes globisporus
Actinoplanes humidus
Actinoplanes italicus
Actinoplanes liguriensis
Actinoplanes lobatus
Actinoplanes missouriensis
Actinoplanes palleronii
Actinoplanes philippinensis
Actinoplanes rectilineatus
Actinoplanes regularis
Actinoplanes teichomyceticus
Actinoplanes utahensis
Actinopolyspora Actinopolyspora halophila
Actinopolyspora mortivallis
Actinosynnema Actinosynnema mirum
Actinotalea Actinotalea fermentans
Aerococcus Aerococcus sanguinicola
Aerococcus urinae
Aerococcus urinaeequi
Aerococcus urinaehominis
Aerococcus viridans
Aeromicrobium Aeromicrobium erythreum
Aeromonas Aeromonas allosaccharophila
Aeromonas bestiarum
Aeromonas caviae
Aeromonas encheleia
Aeromonas enteropelogenes
Aeromonas eucrenophila
Aeromonas ichthiosmia
Aeromonas jandaei
Aeromonas media
Aeromonas popoffii
Aeromonas sobria
Aeromonas veronii
Agrobacterium Agrobacterium gelatinovorum
Agrococcus Agrococcus citreus
Agrococcus jenensis
Agromonas Agromonas oligotrophica
Agromyces Agromyces fucosus
Agromyces hippuratus
Agromyces luteolus
Agromyces mediolanus

TABLE 7-continued

Example Bacteria

*Agromyces ramosus*
*Agromyces rhizospherae*
Akkermansia

*Akkermansia muciniphila*
Albidiferax

*Albidiferax ferrireducens*
Albidovulum

*Albidovulum inexpectatum*
Alcaligenes

*Alcaligenes denitrificans*
*Alcaligenes faecalis*
Alcanivorax

*Alcanivorax borkumensis*
*Alcanivorax jadensis*
Algicola

*Algicola bacteriolytica*
Alicyclobacillus

*Alicyclobacillus disulfidooxidans*
*Alicyclobacillus sendaiensis*
*Alicyclobacillus vulcanalis*
Alishewanella

*Alishewanella fetalis*
Alkalibacillus

*Alkalibacillus haloalkaliphilus*
Alkalilimnicola

*Alkalilimnicola ehrlichii*
Alkaliphilus

*Alkaliphilus oremlandii*
*Alkaliphilus transvaalensis*
Allochromatium

*Allochromatium vinosum*
Alloiococcus

*Alloiococcus otitis*
Allokutzneria

*Allokutzneria albata*
Altererythrobacter

*Altererythrobacter ishigakiensis*
Alteromonas

*Alteromonas haloplanktis*
*Alteromonas macleodii*
Alysiella

*Alysiella crassa*
*Alysiella filiformis*
Aminobacter

*Aminobacter aganoensis*
*Aminobacter aminovorans*
*Aminobacter niigataensis*
Aminobacterium

*Aminobacterium mobile*
Aminomonas

*Aminomonas paucivorans*

TABLE 7-continued

Example Bacteria

Ammoniphilus

*Ammoniphilus oxalaticus*
*Ammoniphilus oxalivorans*
Amphibacillus

*Amphibacillus xylanus*
Amphritea

*Amphritea balenae*
*Amphritea japonica*
Amycolatopsis

*Amycolatopsis alba*
*Amycolatopsis albidoflavus*
*Amycolatopsis azurea*
*Amycolatopsis coloradensis*
*Amycolatopsis lurida*
*Amycolatopsis mediterranei*
*Amycolatopsis rifamycinica*
*Amycolatopsis rubida*
*Amycolatopsis sulphurea*
*Amycolatopsis tolypomycina*
Anabaena

*Anabaena cylindrica*
*Anabaena flos-aquae*
*Anabaena variabilis*
Anaeroarcus

*Anaeroarcus burkinensis*
Anaerobaculum

*Anaerobaculum mobile*
Anaerobiospirillum

*Anaerobiospirillum succiniciproducens*
*Anaerobiospirillum thomasii*
Anaerococcus

*Anaerococcus hydrogenalis*
*Anaerococcus lactolyticus*
*Anaerococcus prevotii*
*Anaerococcus tetradius*
*Anaerococcus vaginalis*
Anaerofustis

*Anaerofustis stercorihominis*
Anaeromusa

*Anaeromusa acidaminophila*
Anaeromyxobacter

*Anaeromyxobacter dehalogenans*
Anaerorhabdus

*Anaerorhabdus furcosa*
Anaerosinus

*Anaerosinus glycerini*
Anaerovirgula

*Anaerovirgula multivorans*
Ancalomicrobium

*Ancalomicrobium adetum*
Ancylobacter

*Ancylobacter aquaticus*
Aneurinibacillus

*Aneurinibacillus aneurinilyticus*
*Aneurinibacillus migulanus*
*Aneurinibacillus thermoaerophilus*

TABLE 7-continued

Example Bacteria

Angiococcus

*Angiococcus disciformis*
Angulomicrobium

*Angulomicrobium tetraedrale*
Anoxybacillus

*Anoxybacillus pushchinoensis*
Aquabacterium

*Aquabacterium commune*
*Aquabacterium parvum*
Aquaspirillum

*Aquaspirillum polymorphum*
*Aquaspirillum putridiconchylium*
*Aquaspirillum serpens*
Aquimarina

*Aquimarina latercula*
Arcanobacterium

*Arcanobacterium haemolyticum*
*Arcanobacterium pyogenes*
Archangium

*Archangium gephyra*
Arcobacter

*Arcobacter butzleri*
*Arcobacter cryaerophilus*
*Arcobacter halophilus*
*Arcobacter nitrofigilis*
*Arcobacter skirrowii*
Arhodomonas

*Arhodomonas aquaeolei*
Arsenophonus

*Arsenophonus nasoniae*
Arthrobacter

*Arthrobacter agilis*
*Arthrobacter albus*
*Arthrobacter aurescens*
*Arthrobacter chlorophenolicus*
*Arthrobacter citreus*
*Arthrobacter crystallopoietes*
*Arthrobacter cumminsii*
*Arthrobacter globiformis*
*Arthrobacter histidinolovorans*
*Arthrobacter ilicis*
*Arthrobacter luteus*
*Arthrobacter methylotrophus*
*Arthrobacter mysorens*
*Arthrobacter nicotianae*
*Arthrobacter nicotinovorans*
*Arthrobacter oxydans*
*Arthrobacter pascens*
*Arthrobacter phenanthrenivorans*
*Arthrobacter polychromogenes*
*Atrhrobacter protophormiae*
*Arthrobacter psychrolactophilus*
*Arthrobacter ramosus*
*Arthrobacter sulfonivorans*
*Arthrobacter sulfureus*
*Arthrobacter uratoxydans*
*Arthrobacter ureafaciens*
*Arthrobacter viscosus*
*Arthrobacter woluwensis*

TABLE 7-continued

Example Bacteria

Asaia

*Asaia bogorensis*
Asanoa

*Asanoa ferruginea*
Asticcacaulis

*Asticcacaulis biprosthecium*
*Asticcacaulis excentricus*
Atopobacter

*Atopobacter phocae*
Atopobium

*Atopobium fossor*
*Atopobium minutum*
*Atopobium parvulum*
*Atopobium rimae*
*Atopobium vaginae*
Aureobacterium

*Aureobacterium barkeri*
Aurobacterium

*Aurobacterium liquefaciens*
Avibacterium

*Avibacterium avium*
*Avibacterium gallinarum*
*Avibacterium paragallinarum*
*Avibacterium volantium*
Azoarcus

*Azoarcus indigens*
*Azoarcus tolulyticus*
*Azoarcus toluvorans*
Azohydromonas

*Azohydromonas australica*
*Azohydromonas lata*
Azomonas

*Azomonas agilis*
*Azomonas insignis*
*Azomonas macrocytogenes*
Azorhizobium

*Azorhizobium caulinodans*
Azorhizophilus

*Azorhizophilus paspali*
Azospirillum

*Azospirillum brasilense*
*Azospirillum halopraeferens*
*Azospirillum irakense*
Azotobacter

*Azotobacter beijerinckii*
*Azotobacter chroococcum*
*Azotobacter nigricans*
*Azotobacter salinestris*
*Azotobacter vinelandii*
Bacillus

[see below]
Bacteriovorax

*Bacteriovorax stolpii*
Bacteroides

*Bacteroides caccae*
*Bacteroides coagulans*
*Bacteroides eggerthii*
*Bacteroides fragilis*
*Bacteroides galacturonicus*
*Bacteroides helcogenes*
*Bacteroides ovatus*
*Bacteroides pectinophilus*

TABLE 7-continued

Example Bacteria

*Bacteroides pyogenes*
*Bacteroides salyersiae*
*Bacteroides stercoris*
*Bacteroides suis*
*Bacteroides tectus*
*Bacteroides thetaiotaomicron*
*Bacteroides uniformis*
*Bacteroides ureolyticus*
*Bacteroides vulgatus*
Balnearium

*Balnearium lithotrophicum*
Balneatrix

*Balneatrix alpica*
Balneola

*Balneola vulgaris*
Barnesiella

*Barnesiella viscericola*
Bartonella

*Bartonella alsatica*
*Bartonella bacilliformis*
*Bartonella clarridgeiae*
*Bartonella doshiae*
*Bartonella elizabethae*
*Bartonella grahamii*
*Bartonella henselae*
*Bartonella rochalimae*
*Bartonella vinsonii*
Bavariicoccus

*Bavariicoccus seileri*
Bdellovibrio

*Bdellovibrio bacteriovorus*
*Bdellovibrio exovorus*
Beggiatoa

*Beggiatoa alba*
Beijerinckia

*Beijerinckia derxii*
*Beijerinckia fluminensis*
*Beijerinckia indica*
*Beijerinckia mobilis*
Belliella

*Belliella baltica*
Bellilinea

*Bellilinea caldifistulae*
Belnapia

*Belnapia moabensis*
Bergeriella

Bergeriella denitrificans
Beutenbergia

*Beutenbergia cavernea*
Bibersteinia

*Bibersteinia trehalosi*
Bifidobacterium

*Bifidobacterium adolescentis*
*Bifidobacterium angulatum*
*Bifidobacterium animalis*
*Bifidobacterium asteroides*
*Bifidobacterium bifidum*
*Bifidobacterium boum*
*Bifidobacterium breve*
*Bifidobacterium catenulatum*
*Bifidobacterium choerinum*
*Bifidobacterium coryneforme*

*Bifidobacterium cuniculi*
*Bifidobacterium dentium*
*Bifidobacterium gallicum*
*Bifidobacterium gallinarum*
*Bifidobacterium indicum*
*Bifidobacterium longum*
*Bifidobacterium magnumBifidobacterium merycicum*
*Bifidobacterium minimum*
*Bifidobacterium pseudocatenulatum*
*Bifidobacterium pseudolongum*
*Bifidobacterium pullorum*
*Bifidobacterium ruminantium*
*Bifidobacterium saeculare*
*Bifidobacterium subtile*
*Bifidobacterium thermophilum*
Bilophila

*Bilophila wadsworthia*
Biostraticola

*Biostraticola tofi*
Bizionia

*Bizionia argentinensis*
Blastobacter

*Blastobacter capsulatus*
*Blastobacter denitrificans*
Blastococcus

*Blastococcus aggregatus*
*Blastococcus saxobsidens*
Blastochloris

*Blastochloris viridis*
Blastomonas

*Blastomonas natatoria*
Blastopirellula

*Blastopirellula marina*
Blautia

*Blautia coccoides*
*Blautia hansenii*
*Blautia producta*
*Blautia wexlerae*
Bogoriella

*Bogoriella caseilytica*
Bordetella

*Bordetella avium*
*Bordetella bronchiseptica*
*Bordetella hinzii*
*Bordetella holmesii*
*Bordetella parapertussis*
*Bordetella pertussis*
*Bordetella petrii*
*Bordetella trematum*
Borrelia

*Borrelia afzelii*
*Borrelia americana*
*Borrelia burgdorferi*
*Borrelia carolinensis*
*Borrelia coriaceae*
*Borrelia garinii*
*Borrelia japonica*
Bosea

*Bosea minatitlanensis*
*Bosea thiooxidans*

TABLE 7-continued

Example Bacteria

Brachybacterium

*Brachybacterium alimentarium*
*Brachybacterium faecium*
*Brachybacterium paraconglomeratum*
*Brachybacterium rhamnosum*
*Brachybacterium tyrofermentans*
Brachyspira

*Brachyspira alvinipulli*
*Brachyspira hyodysenteriae*
*Brachyspira innocens*
*Brachyspira murdochii*
*Brachyspira pilosicoli*
Bradyrhizobium

*Bradyrhizobium canariense*
*Bradyrhizobium elkanii*
*Bradyrhizobium japonicum*
*Bradyrhizobium liaoningense*
Brenneria

*Brenneria alni*
*Brenneria nigrifluens*
*Brenneria quercina*
*Brenneria quercina*
*Brenneria salicis*
Brevibacillus

*Brevibacillus agri*
*Brevibacillus borstelensis*
*Brevibacillus brevis*
*Brevibacillus centrosporus*
*Brevibacillus choshinensis*
*Brevibacillus invocatus*
*Brevibacillus laterosporus*
*Brevibacillus parabrevis*
*Brevibacillus reuszeri*
Brevibacterium

*Brevibacterium abidum*
*Brevibacterium album*
*Brevibacterium aurantiacum*
*Brevibacterium celere*
*Brevibacterium epidermidis*
*Brevibacterium frigoritolerans*
*Brevibacterium halotolerans*
*Brevibacterium iodinum*
*Brevibacterium linens*
*Brevibacterium lyticum*
*Brevibacterium mcbrellneri*
*Brevibacterium otitidis*
*Brevibacterium oxydans*
*Brevibacterium paucivorans*
*Brevibacterium stationis*
Brevinema

*Brevinema andersonii*
Brevundimonas

*Brevundimonas alba*
*Brevundimonas aurantiaca*
*Brevundimonas diminuta*
*Brevundimonas intermedia*
*Brevundimonas subvibrioides*
*Brevundimonas vancanneytii*
*Brevundimonas variabilis*
*Brevundimonas vesicularis*
Brochothrix

*Brochothrix campestris*
*Brochothrix thermosphacta*

Brucella

*Brucella canis*
*Brucella neotomae*
Bryobacter

*Bryobacter aggregatus*
Burkholderia

*Burkholderia ambifaria*
*Burkholderia andropogonis*
*Burkholderia anthina*
*Burkholderia caledonica*
*Burkholderia caryophylli*
*Burkholderia cenocepacia*
*Burkholderia cepacia*
*Burkholderia cocovenenans*
*Burkholderia dolosa*
*Burkholderia fungorum*
*Burkholderia glathei*
*Burkholderia glumae*
*Burkholderia graminis*
*Burkholderia kururiensis*
*Burkholderia multivorans*
*Burkholderia phenazinium*
*Burkholderia plantarii*
*Burkholderia pyrrocinia*
*Burkholderia silvatlantica*
*Burkholderia stabilis*
*Burkholderia thailandensis*
*Burkholderia tropica*
*Burkholderia unamae*
*Burkholderia vietnamiensis*
Buttiauxella

*Buttiauxella agrestis*
*Buttiauxella brennerae*
*Buttiauxella ferragutiae*
*Buttiauxella gaviniae*
*Buttiauxella izardii*
*Buttiauxella noackiae*
*Buttiauxella warmboldiae*
Butyrivibrio

*Butyrivibrio fibrisolvens*
*Butyrivibrio hungatei*
*Butyrivibrio proteoclasticus*
Bacillus

*B. acidiceler*
*B. acidicola*
*B. acidiproducens*
*B. acidocaldarius*
*B. acidoterrestris*
*B. aeolius*
*B. aerius*
*B. aerophilus*
*B. agaradhaerens*
*B. agri*
*B. aidingensis*
*B. akibai*
*B. alcalophilus*
*B. algicola*
*B. alginolyticus*
*B. alkalidiazotrophicus*
*B. alkalinitrilicus*
*B. alkalisediminis*
*B. alkalitelluris*
*B. altitudinis*
*B. alveayuensis*
*B. alvei*
*B. amyloliquefaciens*
  *B. a. subsp. amyloliquefaciens*
  *B. a. subsp. plantarum*
*B. dipsosauri*
*B. drentensis*
*B. edaphicus*

TABLE 7-continued

Example Bacteria

B. ehimensis
B. eiseniae
B. enclensis
B. endophyticus
B. endoradicis
B. farraginis
B. fastidiosus
B. fengqiuensis
B. firmus
B. flexus
B. foraminis
B. fordii
B. fortis
B. fumarioli
B. funiculus
B. fusiformis
B. galactophilus
B. galactosidilyticus
B. galliciensis
B. gelatini
B. gibsonii
B. ginsengi
B. ginsengihumi
B. ginsengisoli
B. glodisporus (eg, B. g. subsp. Globisporus; or B. g. subsp. Marinus)
B. aminovorans
B. amylolyticus
B. andreesenii
B. aneurinilyticus
B. anthracis
B. aquimaris
B. arenosi
B. arseniciselenatis
B. arsenicus
B. aurantiacus
B. arvi
B. aryabhattai
B. asahii
B. atrophaeus
B. axarquiensis
B. azotofixans
B. azotoformans
B. badius
B. barbaricus
B. bataviensis
B. beijingensis
B. benzoevorans
B. beringensis
B. berkeleyi
B. beveridgei
B. bogoriensis
B. boroniphilus 00
B. borstelensis
B. brevis Migula
B. butanolivorans
B. canaveralius
B. carboniphilus
B. cecembensis
B. cellulosilyticus
B. centrosporus
B. cereus
B. chagannorensis
B. chitinolyticus
B. chondroitinus
B. choshinensis
B. chungangensis
B. cibi
B. circulans
B. clarkii
B. clausii
B. coagulans
B. coahuilensis
B. cohnii
B. composti
B. curdlanolyticus
B. cycloheptanicus TABLE 7-continued Example Bacteria B. cytotoxicus
B. daliensis
B. decisifrondis
B. decolorationis
B. deserti
B. glucanolyticus
B. gordonae
B. gottheilii
B. graminis
B. halmapalus
B. haloalkaliphilus
B. halochares
B. halodenitrificans
B. halodurans
B. halophilus
B. halosaccharovorans
B. hemicellulosilyticus
B. hemicentroti
B. herbersteinensis
B. horikoshii
B. horneckiae
B. horti
B. huizhouensis
B. humi
B. hwajinpoensis
B. idriensis
B. indicus
B. infantis
B. infernus
B. insolitus
B. invictae
B. iranensis
B. isabeliae
B. isronensis
B. jeotgali
B. kaustophilus
B. kobensis
B. kochii
B. kokeshiiformis
B. koreensis
B. korlensis
B. kribbensis
B. krulwichiae
B. laevolacticus
B. larvae
B. laterosporus
B. lautus
B. lehensis
B. lentimorbus
B. lentus
B. licheniformis
B. ligniniphilus
B. litoralis
B. locisalis
B. luciferensis
B. luteolus
B. luteus
B. macauensis
B. macerans
B. macquariensis
B. macyae
B. malacitensis
B. mannanilyticus
B. marisflavi
B. marismortui
B. marmarensis
B. massiliensis
B. megaterium
B. mesonae
B. methanolicus
B. methylotrophicus
B. migulanus
B. mojavensis
B. mucilaginosus
B. muralis
B. murimartini
B. mycoides
B. naganoensis TABLE 7-continued Example Bacteria B. nanhaiensis
B. nanhaiisediminis
B. nealsonii
B. neidei
B. neizhouensis
B. niabensis
B. niacini
B. novalis
B. oceanisediminis
B. odysseyi
B. okhensis
B. okuhidensis
B. oleronius
B. oryzaecorticis
B. oshimensis
B. pabuli
B. pakistanensis
B. pallidus
B. pallidus
B. panacisoli
B. panaciterrae
B. pantothenticus
B. parabrevis
B. paraflexus
B. pasteurii
B. patagoniensis
B. peoriae
B. persepolensis
B. persicus
B. pervagus
B. plakortidis
B. pocheonensis
B. polygoni
B. polymyxa
B. popilliae
B. pseudalcalophilus
B. pseudofirmus
B. pseudomycoides
B. psychrodurans
B. psychrophilus
B. psychrosaccharolyticus
B. psychrotolerans
B. pulvifaciens
B. pumilus
B. purgationiresistens
B. pycnus
B. qingdaonensis
B. qingshengii
B. reuszeri
B. rhizosphaerae
B. rigui
B. ruris
B. safensis
B. salarius
B. salexigens
B. saliphilus
B. schlegelii
B. sediminis
B. selenatarsenatis
B. selenitireducens
B. seohaeanensis
B. shacheensis
B. shackletonii
B. siamensis
B. silvestris
B. simplex
B. siralis
B. smithii
B. soli
B. solimangrovi
B. solisalsi
B. songklensis
B. sonorensis
B. sphaericus
B. sporothermodurans
B. stearothermophilus
B. stratsphericus
B. subterranueus
B. subtilis (eg, B. s. subsp. Inaquosorum; or B. s. subsp. Spizizeni; or B. s. subsp. Subtilis)
B. taeanensis
B. tequilensis
B. thermantarcticus
B. thermoaerophilus
B. thermoamylovorans
B. thermocatenulatus
B. thermocloacae
B. thermocopriae
B. thermodenitrificans
B. thermoglucosidasius
B. thermolactis
B. thermoleovorans
B. thermophilus
B. thermoruber
B. thermosphaericus
B. thiaminolyticus
B. thioparans
B. thuringiensis
B. tianshenii
B. trypoxylicola
B. tusciae
B. validus
B. vallismortis
B. vedderi
B. velezensis
B. vietnamensis
B. vireti
B. vulcani
B. wakoensis
B. weihenstephanensis
B. xiamenensis
B. xiaoxiensis
B. zhanjiangensis
Caenimonas
Caenimonas koreensis
Caldalkalibacillus
Caldalkalibacillus uzonensis
Caldanaerobacter
Caldanaerobacter subterraneus
Caldanaerobius
Caldanaerobius fijiensis
Caldanaerobius polysaccharolyticus
Caldanaerobius zeae
Caldanaerovirga
Caldanaerovirga acetigignens
Caldicellulosiruptor
Caldicellulosiruptor bescii
Caldicellulosiruptor kristjanssonii
Caldicellulosiruptor owensensis
Campylobacter
Campylobacter coli
Campylobacter concisus
Campylobacter curvus
Campylobacter fetus
Campylobacter gracilis
Campylobacter helveticus
Campylobacter hominis
Campylobacter hyointestinalis
Campylobacter jejuni
Campylobacter lari
Campylobacter mucosalis
Campylobacter rectus
Campylobacter showae
Campylobacter sputorum
Campylobacter upsaliensis TABLE 7-continued Example Bacteria Capnocytophaga Capnocytophaga canimorsus
Capnocytophaga cynodegmi
Capnocytophaga gingivalis
Capnocytophaga granulosa
Capnocytophaga haemolytica
Capnocytophaga ochracea
Capnocytophaga sputigena
Cardiobacterium Cardiobacterium hominis
Carnimonas Carnimonas nigrificans
Carnobacterium Carnobacterium alterfunditum
Carnobacterium divergens
Carnobacterium funditum
Carnobacterium gallinarum
Carnobacterium maltaromaticum
Carnobacterium mobile
Carnobacterium viridans
Caryophanon Caryophanon latum
Caryophanon tenue
Catellatospora Catellatospora citrea
Catellatospora methionotrophica
Catenococcus Catenococcus thiocycli
Catenuloplanes Catenuloplanes atrovinosus
Catenuloplanes castaneus
Catenuloplanes crispus
Catenuloplanes indicus
Catenuloplanes japonicus
Catenuloplanes nepalensis
Catenuloplanes niger
Carnobacterium Carnobacterium alterfunditum
Carnobacterium divergens
Carnobacterium funditum
Carnobacterium gallinarum
Carnobacterium maltaromaticum
Carnobacterium mobile
Carnobacterium virdans
Caryophanon Caryophanon latum
Caryophanon tenue
Catellatospora Catellatospora citrea
Catellatospora methionotrophica
Catenococcus Catenococcus thiocycli
Chryseobacterium Chryseobacterium balustinum
Citrobacter C. amalonaticus
C. braakii
C. diversus
C. farmeri
C. freundii
C. gillenii
C. koseri
C. murliniae
C. pasteurii[1]
C. rodentium
C. sedlakii
C. werkmanii
C. youngae
Clostridium (see below)
Coccochloris Coccochloris elabens
Corynebacterium Corynebacterium flavescens
Corynebacterium variable
Curtobacterium Curtobacterium albidum
Curtobacterium citreus
Clostridium Clostridium absonum,
Clostridium aceticum,
Clostridium acetireducens,
Clostridium acetobutylicum,
Clostridium acidisoli,
Clostridium aciditolerans,
Clostridium acidurici,
Clostridium aerotolerans,
Clostridium aestuarii,
Clostridium akagii,
Clostridium aldenense,
Clostridium aldrichii,
Clostridium algidicarni,
Clostridium algidixylanolyticum,
Clostridium algifaecis,
Clostridium algoriphilum,
Clostridium alkalicellulosi,
Clostridium aminophilum,
Clostridium aminovalericum,
Clostridium amygdalinum,
Clostridium amylolyticum,
Clostridium arbusti,
Clostridium arcticum,
Clostridium argentinense,
Clostridium asparagiforme,
Clostridium aurantibutyricum,
Clostridium autoethanogenum,
Clostridium baratii,
Clostridium barkeri,
Clostridium bartlettii,
Clostridium beijerinckii,
Clostridium bifermentans,
Clostridium bolteae,
Clostridium bornimense,
Clostridium botulinum,
Clostridium bowmanii,
Clostridium bryantii,
Clostridium butyricum,
Clostridium cadaveris,
Clostridium caenicola,
Clostridium caminithermale,
Clostridium carboxidivorans,
Clostridium carnis,
Clostridium cavendishii,
Clostridium celatum,
Clostridium celerecrescens,
Clostridium cellobioparum,
Clostridium cellulofermentans,
Clostridium cellulolyticum,
Clostridium cellulosi,
Clostridium cellulovorans,
Clostridium chartatabidum,
Clostridium chauvoei,

TABLE 7-continued

Example Bacteria

Clostridium chromiireducens,
Clostridium citroniae,
Clostridium clariflavum,
Clostridium clostridioforme,
Clostridium coccoides,
Clostridium cochlearium,
Clostridium colletant,
Clostridium colicanis,
Clostridium colinum,
Clostridium collagenovorans,
Clostridium cylindrosporum,
Clostridium difficile,
Clostridium diolis,
Clostridium disporicum,
Clostridium drakei,
Clostridium durum,
Clostridium estertheticum,
Clostridium estertheticum estertheticum,
Clostridium estertheticum laramiense,
Clostridium fallax,
Clostridium felsineum,
Clostridium fervidum,
Clostridium fimetarium,
Clostridium formicaceticum,
Clostridium frigidicarnis,
Clostridium frigoris,
Clostridium ganghwense,
Clostridium gasigenes,
Clostridium ghonii,
Clostridium glycolicum,
Clostridium glycyrrhizinilyticum,
Clostridium grantii,
Clostridium haemolyticum,
Clostridium halophilum,
Clostridium hastiforme,
Clostridium hathewayi,
Clostridium herbivorans,
Clostridium hiranonis,
Clostridium histolyticum,
Clostridium homopropionicum,
Clostridium huakuii,
Clostridium hungatei,
Clostridium hydrogeniformans,
Clostridium hydroxybenzoicum,
Clostridium hylemonae,
Clostridium jejuense,
Clostridium indolis,
Clostridium innocuum,
Clostridium intestinale,
Clostridium irregulare,
Clostridium isatidis,
Clostridium josui,
Clostridium kluyveri,
Clostridium lactatifermentans,
Clostridium lacusfryxellense,
Clostridium laramiense,
Clostridium lavalense,
Clostridium lentocellum,
Clostridium lentoputrescens,
Clostridium leptum,
Clostridium limosum,
Clostridium litorale,
Clostridium lituseburense,
Clostridium ljungdahlii,
Clostridium lortetii,
Clostridium lundense,
Clostridium magnum,
Clostridium malenominatum,
Clostridium mangenotii,
Clostridium mayombei,
Clostridium methoxy benzovorans,
Clostridium methylpentosum,
Clostridium neopropionicum,
Clostridium nexile,
Clostridium nitrophenolicum,
Clostridium novyi,
Clostridium oceanicum,
Clostridium orbiscindens,
Clostridium oroticum,
Clostridium oxalicum,
Clostridium papyrosolvens,
Clostridium paradoxum,
Clostridium paraperfringens (Alias: C. welchii),
Clostridium paraputrificum,
Clostridium pascui,
Clostridium pasteurianum,
Clostridium peptidivorans,
Clostridium perenne,
Clostridium perfringens,
Clostridium pfennigii,
Clostridium phytofermentans,
Clostridium piliforme,
Clostridium polysaccharolyticum,
Clostridium populeti,
Clostridium propionicum,
Clostridium proteoclasticum,
Clostridium proteolyticum,
Clostridium psychrophilum,
Clostridium puniceum,
Clostridium purinilyticum,
Clostridium putrefaciens,
Clostridium putrificum,
Clostridium quercicolum,
Clostridium quinii,
Clostridium ramosum,
Clostridium rectum,
Clostridium roseum,
Clostridium saccharobutylicum,
Clostridium saccharogumia,
Clostridium saccharolyticum,
Clostridium saccharoperbutylacetonicum,
Clostridium sardiniense,
Clostridium sartagoforme,
Clostridium scatologenes,
Clostridium schirmacherense,
Clostridium scindens,
Clostridium septicum,
Clostridium sordellii,
Clostridium sphenoides,
Clostridium spiroforme,
Clostridium sporogenes,
Clostridium sporosphaeroides,
Clostridium stercorarium,
Clostridium stercorarium leptospartum,
Clostridium stercorarium stercorarium,
Clostridium stercorarium thermolacticum,
Clostridium sticklandii,
Clostridium straminisolvens,
Clostridium subterminale,
Clostridium sufflavum,
Clostridium sulfidigenes,
Clostridium symbiosum,
Clostridium tagluense,
Clostridium tepidiprofundi,
Clostridium termitidis,
Clostridium tertium,
Clostridium tetani,
Clostridium tetanomorphum,
Clostridium thermaceticum,
Clostridium thermautotrophicum,
Clostridium thermoalcaliphilum,
Clostridium thermobutyricum,
Clostridium thermocellum,
Clostridium thermocopriae,
Clostridium thermohydrosulfuricum,
Clostridium thermolacticum,
Clostridium thermopalmarium,
Clostridium thermopapyrolyticum,
Clostridium thermosaccharolyticum,
Clostridium thermosuccinogenes,
Clostridium thermosulfurigenes,
Clostridium thiosulfatireducens,
Clostridium tyrobutyricum,
Clostridium uliginosum,
Clostridium ultunense,
Clostridium villosum, TABLE 7-continued

| Example Bacteria |
|---|
| *Clostridium vincentii,* |
| *Clostridium viride,* |
| *Clostridium xylanolyticum,* |
| *Clostridium xylanovorans* |
| Dactylosporangium |
| |
| *Dactylosporangium aurantiacum* |
| *Dactylosporangium fulvum* |
| *Dactylosporangium matsuzakiense* |
| *Dactylosporangium roseum* |
| *Dactylosporangium thailandense* |
| *Dactylosporangium vinaceum* |
| Deinococcus |
| |
| *Deinococcus aerius* |
| *Deinococcus apachensis* |
| *Deinococcus aquaticus* |
| *Deinococcus aquatilis* |
| *Deinococcus caeni* |
| *Deinococcus radiodurans* |
| *Deinococcus radiophilus* |
| Delftia |
| |
| *Delftia acidovorans* |
| Desulfovibrio |
| |
| *Desulfovibrio desulfuricans* |
| Diplococcus |
| |
| *Diplococcus pneumoniae* |
| Echinicola |
| |
| *Echinicola pacifica* |
| *Echinicola vietnamensis* |
| Enterobacter |
| |
| *E. aerogenes* |
| *E. amnigenus* |
| *E. agglomerans* |
| *E. arachidis* |
| *E. asburiae* |
| *E. cancerogenous* |
| *E. cloacae* |
| *E. cowanii* |
| *E. dissolvens* |
| *E. gergoviae* |
| *E. helveticus* |
| *E. hormaechei* |
| *E. intermedius* |
| Enterobacter kobei |
| *E. ludwigii* |
| *E. mori* |
| *E. nimipressuralis* |
| *E. oryzae* |
| *E. pulveris* |
| *E. pyrinus* |
| *E. radicincitans* |
| *E. taylorae* |
| *E. turicensis* |
| Faecalibacterium |
| |
| *Faecalibacterium prausnitzii* |
| Fangia |
| |
| *Fangia hongkongensis* |
| Fastidiosipila |
| |
| *Fastidiosipila sanguinis* |
| Flavobacterium |
| |
| *Flavobacterium antarcticum* |
| *Flavobacterium aquatile* |
| *Flavobacterium aquidurense* |
| *Flavobacterium balustinum* |
| *Flavobacterium croceum* |
| *Flavobacterium cucumis* |
| *Flavobacterium daejeonense* |
| *Flavobacterium defluvii* |
| *Flavobacterium degerlachei* |
| *Flavobacterium denitrificans* |
| *Flavobacterium filum* |
| *Flavobacterium flevense* |
| *Flavobacterium frigidarium* |
| *Flavobacterium mizutaii* |
| *Flavobacterium okeanokoites* |
| Fusobacterium |
| |
| *Fusobacterium nucleatum* |
| Gaetbulibacter |
| |
| *Gaetbulibacter saemankumensis* |
| Gallibacterium |
| |
| *Gallibacterium anatis* |
| Gallicola |
| |
| *Gallicola barnesae* |
| Garciella |
| |
| *Garciella nitratireducens* |
| Geobacillus |
| |
| *Geobacillus thermoglucosidasius* |
| *Geobacillus stearothermophilus* |
| Geobacter |
| |
| *Geobacter bemidjiensis* |
| *Geobacter bremensis* |
| *Geobacter chapellei* |
| *Geobacter grbiciae* |
| *Geobacter hydrogenophilus* |
| *Geobacter lovleyi* |
| *Geobacter metallireducens* |
| *Geobacter pelophilus* |
| *Geobacter pickeringii* |
| *Geobacter sulfurreducens* |
| Geodermatophilus |
| |
| *Geodermatophilus obscurus* |
| Gluconacetobacter |
| |
| *Gluconacetobacter xylinus* |
| Gordonia |
| |
| *Gordonia rubripertincta* |
| Haemophilus |
| |
| *Haemophilus aegyptius* |
| *Haemophilus aphrophilus* |
| *Haemophilus felis* |
| *Haemophilus gallinarum* |
| *Haemophilus haemolyticus* |
| *Haemophilus influenzae* |
| *Haemophilus paracuniculus* |
| *Haemophilus parahaemolyticus* |
| *Haemophilus parainfluenzae* |
| *Haemophilus paraphrohaemolyticus* |
| *Haemophilus parasuis* |
| *Haemophilus pittmaniae* |
| Hafnia |
| |
| *Hafnia alvei* |
| Hahella |
| |
| *Hahella ganghwensis* |
| Halalkalibacillus |
| |
| *Halalkalibacillus halophilus* |
| Helicobacter |
| |
| *Helicobacter pylori* |

TABLE 7-continued

Example Bacteria

Ideonella

*Ideonella azotifigens*
Idiomarina

*Idiomarina abyssalis*
*Idiomarina baltica*
*Idiomarina fontislapidosi*
*Idiomarina loihiensis*
*Idiomarina ramblicola*
*Idiomarina seosinensis*
*Idiomarina zobellii*
Ignatzschineria

*Ignatzschineria larvae*
Ignavigranum

*Ignavigranum ruoffiae*
Ilumatobacter

*Ilumatobacter fluminis*
Ilyobacter

*Ilyobacter delafieldii*
*Ilyobacter insuetus*
*Ilyobacter polytropus*
*Ilyobacter tartaricus*
Janibacter

*Janibacter anophelis*
*Janibacter corallicola*
*Janibacter limosus*
*Janibacter melonis*
*Janibacter terrae*
Jannaschia

*Jannaschia cystaugens*
*Jannaschia helgolandensis*
*Jannaschia pohangensis*
*Jannaschia rubra*
Janthinobacterium

*Janthinobacterium agaricidamnosum*
*Janthinobacterium lividum*
Jejuia

*Jejuia pallidilutea*
Jeotgalibacillus

*Jeotgalibacillus alimentarius*
Jeotgalicoccus

*Jeotgalicoccus halotolerans*
Kaistia

*Kaistia adipata*
*Kaistia soli*
Kangiella

*Kangiella aquimarina*
*Kangiella koreensis*
Kerstersia

*Kerstersia gyiorum*
Kiloniella

*Kiloniella laminariae*
Klebsiella

*K. granulomatis*
*K. oxytoca*
*K. pneumoniae*
*K. terrigena*
*K. variicola*

TABLE 7-continued

Example Bacteria

Kluyvera

*Kluyvera ascorbata*
Kocuria

*Kocuria roasea*
*Kocuria varians*
Kurthia

*Kurthia zopfii*
Labedella

*Labedella gwakjiensis*
Labrenzia

*Labrenzia aggregata*
*Labrenzia alba*
*Labrenzia alexandrii*
*Labrenzia marina*
Labrys

*Labrys methylaminiphilus*
*Labrys miyagiensis*
*Labrys monachus*
*Labrys okinawensis*
*Labrys portucalensis*
Lactobacillus

[see below]
Laceyella

*Laceyella putida*
Lechevalieria

*Lechevalieria aerocolonigenes*
Legionella

[see below]
Listeria

*L. aquatica*
*L. booriae*
*L. cornellensis*
*L. fleischmannii*
*L. floridensis*
*L. grandensis*
*L. grayi*
*L. innocua*
*Listeria ivanovii*
*L. marthii*
*L. monocytogenes*
*L. newyorkensis*
*L. riparia*
*L. rocourtiae*
*L. seeligeri*
*L. weihenstephanensis*
*L. welshimeri*
Listonella

*Listonella anguillarum*
Macrococcus

*Macrococcus bovicus*
Marinobacter

*Marinobacter algicola*
*Marinobacter bryozoorum*
*Marinobacter flavimaris*
Meiothermus

*Meiothermus ruber*
Methylophilus

*Methylophilus methylotrophus*

TABLE 7-continued

| Example Bacteria |
|---|
| Microbacterium |
| |
| *Microbacterium ammoniaphilum* |
| *Microbacterium arborescens* |
| *Microbacterium liquefaciens* |
| *Microbacterium oxydans* |
| Micrococcus |
| |
| *Micrococcus luteus* |
| *Micrococcus lylae* |
| Moraxella |
| |
| *Moraxella bovis* |
| *Moraxella nonliquefaciens* |
| *Moraxella osloensis* |
| Nakamurella |
| |
| *Nakamurella multipartita* |
| Nannocystis |
| |
| *Nannocystis pusilla* |
| Natranaerobius |
| |
| *Natranaerobius thermophilus* |
| *Natranaerobius trueperi* |
| Naxibacter |
| |
| *Naxibacter alkalitolerans* |
| Neisseria |
| |
| *Neisseria cinerea* |
| *Neisseria denitrificans* |
| *Neisseria gonorrhoeae* |
| *Neisseria lactamica* |
| *Neisseria mucosa* |
| *Neisseria sicca* |
| *Neisseria subflava* |
| Neptunomonas |
| |
| *Neptunomonas japonica* |
| Nesterenkonia |
| |
| *Nesterenkonia holobia* |
| Nocardia |
| |
| *Nocardia argentinensis* |
| *Nocardia corallina* |
| *Nocardia otitidiscaviarum* |
| Lactobacillus |
| |
| *L. acetotolerans* |
| *L. acidifarinae* |
| *L. acidipiscis* |
| *L. acidophilus* |
| *Lactobacillus agilis* |
| *L. algidus* |
| *L. alimentarius* |
| *L. amylolyticus* |
| *L. amylophilus* |
| *L. amylotrophicus* |
| *L. amylovorus* |
| *L. animalis* |
| *L. antri* |
| *L. apodemi* |
| *L. aviarius* |
| *L. bifermentans* |
| *L. brevis* |
| *L. buchneri* |
| *L. camelliae* |
| *L. casei* |
| *L. kitasatonis* |
| *L. kunkeei* |
| *L. leichmannii* |
| *L. lindneri* |
| *L. malefermentans* |
| *L. catenaformis* |
| *L. ceti* |
| *L. coleohominis* |
| *L. collinoides* |
| *L. composti* |
| *L. concavus* |
| *L. coryniformis* |
| *L. crispatus* |
| *L. crustorum* |
| *L. curvatus* |
| *L. delbrueckii subsp. bulgaricus* |
| *L. delbrueckii subsp. delbrueckii* |
| *L. delbrueckii subsp. lactis* |
| *L. dextrinicus* |
| *L. diolivorans* |
| *L. equi* |
| *L. equigenerosi* |
| *L. farraginis* |
| *L. farciminis* |
| *L. fermentum* |
| *L. fornicalis* |
| *L. fructivorans* |
| *L. frumenti* |
| *L. mali* |
| *L. manihotivorans* |
| *L. mindensis* |
| *L. mucosae* |
| *L. murinus* |
| *L. nagelii* |
| *L. namurensis* |
| *L. nantensis* |
| *L. oligofermentans* |
| *L. oris* |
| *L. panis* |
| *L. pantheris* |
| *L. parabrevis* |
| *L. parabuchneri* |
| *L. paracasei* |
| *L. paracollinoides* |
| *L. parafarraginis* |
| *L. homohiochii* |
| *L. iners* |
| *L. ingluviei* |
| *L. intestinalis* |
| *L. fuchuensis* |
| *L. gallinarum* |
| *L. gasseri* |
| *L. parakefiri* |
| *L. paralimentarius* |
| *L. paraplantarum* |
| *L. pentosus* |
| *L. perolens* |
| *L. plantarum* |
| *L. pontis* |
| *L. protectus* |
| *L. psittaci* |
| *L. rennini* |
| *L. reuteri* |
| *L. rhamnosus* |
| *L. rimae* |
| *L. rogosae* |
| *L. rossiae* |
| *L. ruminis* |
| *L. saerimneri* |
| *L. jensenii* |
| *L. johnsonii* |
| *L. kalixensis* |
| *L. kefiranofaciens* |
| *L. kefiri* |
| *L. kimchii* |
| *L. helveticus* |
| *L. hilgardii* |
| *L. sakei* |
| *L. salivarius* |
| *L. sanfranciscensis* |
| *L. satsumensis* |

TABLE 7-continued

Example Bacteria

*L. secaliphilus*
*L. sharpeae*
*L. siliginis*
*L. spicheri*
*L. suebicus*
*L. thailandensis*
*L. ultunensis*
*L. vaccinostercus*
*L. vaginalis*
*L. versmoldensis*
*L. vini*
*L. vitulinus*
*L. zeae*
*L. zymae*
*L. gastricus*
*L. ghanensis*
*L. graminis*
*L. hammesii*
*L. hamsteri*
*L. harbinensis*
*L. hayakitensis*
Legionella

*Legionella adelaidensis*
*Legionella anisa*
*Legionella beliardensis*
*Legionella birminghamensis*
*Legionella bozemanae*
*Legionella brunensis*
*Legionella busanensis*
*Legionella cardiaca*
*Legionella cherrii*
*Legionella cincinnatiensis*
*Legionella clemsonensis*
*Legionella donaldsonii*
*Legionella drancourtii*
*Legionella dresdenensis*
*Legionella drozanskii*
*Legionella dumoffii*
*Legionella erythra*
*Legionella fairfieldensis*
*Legionella fallonii*
*Legionella feeleii*
*Legionella geestiana*
*Legionella* genomospecies
*Legionella gormanii*
*Legionella gratiana*
*Legionella gresilensis*
*Legionella hackeliae*
*Legionella impletisoli*
*Legionella israelensis*
*Legionella jamestowniensis*
*Candidatus* Legionella jeonii
*Legionella jordanis*
*Legionella lansingensis*
*Legionella londiniensis*
*Legionella longbeachae*
*Legionella lytica*
*Legionella maceachernii*
*Legionella massiliensis*
*Legionella micdadei*
*Legionella monrovica*
*Legionella moravica*
*Legionella nagasakiensis*
*Legionella nautarum*
*Legionella norrlandica*
*Legionella oakridgensis*
*Legionella parisiensis*
*Legionella pittsburghensis*
*Legionella pneumophila*
*Legionella quateirensis*
*Legionella quinlivanii*
*Legionella rowbothamii*
*Legionella rubrilucens*
*Legionella sainthelensi*
*Legionella santicrucis*
*Legionella shakespearei*
*Legionella spiritensis*
*Legionella steelei*
*Legionella steigerwaltii*
*Legionella taurinensis*
*Legionella tucsonensis*
*Legionella tunisiensis*
*Legionella wadswothii*
*Legionella waltersii*
*Legionella worsleiensis*
*Legionella yabuuchiae*
Oceanibulbus

*Oceanibulbus indolifex*
Oceanicaulis

*Oceanicaulis alexandrii*
Oceanicola

*Oceanicola batsensis*
*Oceanicola granulosus*
*Oceanicola nanhaiensis*
Oceanimonas

*Oceanimonas baumannii*
Oceaniserpentilla

*Oceaniserpentilla haliotis*
Oceanisphaera

*Oceanisphaera donghaensis*
*Oceanisphaera litoralis*
Oceanithermus

*Oceanithermus desulfurans*
*Oceanithermus profundus*
Oceanobacillus

*Oceanobacillus caeni*
Oceanospirillum

*Oceanospirillum linum*
Paenibacillus

*Paenibacillus thiaminolyticus*
Pantoea

*Pantoea agglomerans*
Paracoccus

*Paracoccus alcaliphilus*
Paucimonas

*Paucimonas lemoignei*
Pectobacterium

*Pectobacterium aroidearum*
*Pectobacterium atrosepticum*
*Pectobacterium betavasculorum*
*Pectobacterium cacticida*
*Pectobacterium carnegieana*
*Pectobacterium carotovorum*
*Pectobacterium chrysanthemi*
*Pectobacterium cypripedii*
*Pectobacterium rhapontici*
*Pectobacterium wasabiae*
Planococcus

*Planococcus citreus*
Planomicrobium

*Planomicrobium okeanokoites*
Plesiomonas

*Plesiomonas shigelloides*
Proteus

*Proteus vulgaris*

TABLE 7-continued

| Example Bacteria |
|---|
| Prevotella |
| *Prevotella albensis* |
| *Prevotella amnii* |
| *Prevotella bergensis* |
| *Prevotella bivia* |
| *Prevotella brevis* |
| *Prevotella bryantii* |
| *Prevotella buccae* |
| *Prevotella buccalis* |
| *Prevotella copri* |
| *Prevotella dentalis* |
| *Prevotella denticola* |
| *Prevotella disiens* |
| *Prevotella histicola* |
| *Prevotella intermedia* |
| *Prevotella maculosa* |
| *Prevotella marshii* |
| *Prevotella melaninogenica* |
| *Prevotella micans* |
| *Prevotella multiformis* |
| *Prevotella nigrescens* |
| *Prevotella oralis* |
| *Prevotella oris* |
| *Prevotella oulorum* |
| *Prevotella pallens* |
| *Prevotella salivae* |
| *Prevotella stercorea* |
| *Prevotella tannerae* |
| *Prevotella timonensis* |
| *Prevotella veroralis* |
| Providencia |
| *Providencia stuartii* |
| Pseudomonas |
| *Pseudomonas aeruginosa* |
| *Pseudomonas alcaligenes* |
| *Pseudomonas anguillispetica* |
| *Pseudomonas fluorescens* |
| *Pseudoalteromonas haloplanktis* |
| *Pseudoalteromonas mendocina* |
| *Pseudoalteromonas pseudoalcaligenes* |
| *Pseudoalteromonas putida* |
| *Pseudoalteromonas tutzeri* |
| *Pseudoalteromonas syringae* |
| Psychrobacter |
| *Psychrobacter faecalis* |
| *Psychrobacter phenylpyruvicus* |
| Quadrisphaera |
| *Quadrisphaera granulorum* |
| Quatrionicoccus |
| *Quatrionicoccus australiensis* |
| Quinella |
| *Quinella ovalis* |
| Ralstonia |
| *Ralstonia eutropha* |
| *Ralstonia insidiosa* |
| *Ralstonia mannitolilytica* |
| *Ralstonia pickettii* |
| *Ralstonia pseudosolanacearum* |
| *Ralstonia syzygii* |
| *Ralstonia solanacearum* |
| Ramlibacter |
| *Ramlibacter henchirensis* |
| *Ramlibacter tataouinensis* |
| Raoultella |
| *Raoultella ornithinolytica* |
| *Raoultella planticola* |
| *Raoultella terrigena* |
| Rathayibacter |
| *Rathayibacter caricis* |
| *Rathayibacter festucae* |
| *Rathayibacter iranicus* |
| *Rathayibacter rathayi* |
| *Rathayibacter toxicus* |
| *Rathayibacter tritici* |
| Rhodobacter |
| *Rhodobacter sphaeroides* |
| Ruegeria |
| *Ruegeria gelatinovorans* |
| Saccharococcus |
| *Saccharococcus thermophilus* |
| Saccharomonospora |
| *Saccharomonospora azurea* |
| *Saccharomonospora cyanea* |
| *Saccharomonospora viridis* |
| Saccharophagus |
| *Saccharophagus degradans* |
| Saccharopolyspora |
| *Saccharopolyspora erythraea* |
| *Saccharopolyspora gregorii* |
| *Saccharopolyspora hirsuta* |
| *Saccharopolyspora hordei* |
| *Saccharopolyspora rectivirgula* |
| *Saccharopolyspora spinosa* |
| *Saccharopolyspora taberi* |
| Saccharothrix |
| *Saccharothrix australiensis* |
| *Saccharothrix coeruleofusca* |
| *Saccharothrix espanaensis* |
| *Saccharothrix longispora* |
| *Saccharothrix mutabilis* |
| *Saccharothrix syringae* |
| *Saccharothrix tangerinus* |
| *Saccharothrix texasensis* |
| Sagittula |
| *Sagittula stellata* |
| Salegentibacter |
| *Salegentibacter salegens* |
| Salimicrobium |
| *Salimicrobium album* |
| Salinibacter |
| *Salinibacter ruber* |
| Salinicoccus |
| *Salinicoccus alkaliphilus* |
| *Salinicoccus hispanicus* |
| *Salinicoccus roseus* |
| Salinispora |
| *Salinispora arenicola* |
| *Salinispora tropica* |
| Salinivibrio |
| *Salinivibrio costicola* |

TABLE 7-continued

Example Bacteria

Salmonella

*Salmonella bongori*
*Salmonella enterica*
*Salmonella subterranea*
*Salmonella typhi*
Sanguibacter

*Sanguibacter keddieii*
*Sanguibacter suarezii*
Saprospira

*Saprospira grandis*
Sarcina

*Sarcina maxima*
*Sarcina ventriculi*
Sebaldella

*Sebaldella termitidis*
Serratia

*Serratia fonticola*
*Serratia marcescens*
Sphaerotilus

*Sphaerotilus natans*
Sphingobacterium

*Sphingobacterium multivorum*
Staphylococcus

[see below]
Stenotrophomonas

*Stenotrophomonas maltophilia*
Streptococcus

[also see below]
Streptomyces

*Streptomyces achromogenes*
*Streptomyces cesalbus*
*Streptomyces cescaepitosus*
*Streptomyces cesdiastaticus*
*Streptomyces cesexfoliatus*
*Streptomyces fimbriatus*
*Streptomyces fradiae*
*Streptomyces fulvissimus*
*Streptomyces griseoruber*
*Streptomyces griseus*
*Streptomyces lavendulae*
*Streptomyces phaeochromogenes*
*Streptomyces thermodiastaticus*
*Streptomyces tubercidicus*
Tatlockia

*Tatlockia maceachernii*
*Tatlockia micdadei*
Tenacibaculum

*Tenacibaculum amylolyticum*
*Tenacibaculum discolor*
*Tenacibaculum gallaicum*
*Tenacibaculum lutimaris*
*Tenacibaculum mesophilum*
*Tenacibaculum skagerrakense*

TABLE 7-continued

Example Bacteria

Tepidanaerobacter

*Tepidanaerobacter syntrophicus*
Tepidibacter

*Tepidibacter formicigenes*
*Tepidibacter thalassicus*
Thermus

*Thermus aquaticus*
*Thermus filiformis*
*Thermus thermophilus*
Staphylococcus

*S. arlettae*
*S. agnetis*
*S. aureus*
*S. auricularis*
*S. capitis*
*S. caprae*
*S. carnosus*
*S. caseolyticus*
*S. chromogenes*
*S. cohnii*
*S. condimenti*
*S. delphini*
*S. devriesei*
*S. epidermidis*
*S. equorum*
*S. felis*
*S. fleurettii*
*S. gallinarum*
*S. haemolyticus*
*S. hominis*
*S. hyicus*
*S. intermedius*
*S. kloosii*
*S. leei*
*S. lentus*
*S. lugdunensis*
*S. lutrae*
*S. lyticans*
*S. massiliensis*
*S. microti*
*S. muscae*
*S. nepalensis*
*S. pasteuri*
*S. petrasii*
*S. pettenkoferi*
*S. piscifermentans*
*S. pseudintermedius*
*S. pseudolugdunensis*
*S. pulvereri*
*S. rostri*
*S. saccharolyticus*
*S. saprophyticus*
*S. schleiferi*
*S. sciuri*
*S. simiae*
*S. simulans*
*S. stepanovicii*
*S. succinus*
*S. vitulinus*
*S. warneri*
*S. xylosus*
Streptococcus

*Streptococcus agalactiae*
*Streptococcus anginosus*
*Streptococcus bovis*
*Streptococcus canis*
*Streptococcus constellatus*
*Streptococcus downei*
*Streptococcus dysgalactiae*
*Streptococcus equines*

TABLE 7-continued

Example Bacteria

*Streptococcus faecalis*
*Streptococcus ferus*
*Streptococcus infantarius*
*Streptococcus iniae*
*Streptococcus intermedius*
*Streptococcus lactarius*
*Streptococcus milleri*
*Streptococcus mitis*
*Streptococcus mutans*
*Streptococcus oralis*
*Streptococcus tigurinus*
*Streptococcus orisratti*
*Streptococcus parasanguinis*
*Streptococcus peroris*
*Streptococcus pneumoniae*
*Streptococcus pseudopneumoniae*
*Streptococcus pyogenes*
*Streptococcus ratti*
*Streptococcus salivariu*
*Streptococcus thermophilus*
*Streptococcus sanguinis*
*Streptococcus sobrinus*
*Streptococcus suis*
*Streptococcus uberis*
*Streptococcus vestibularis*
*Streptococcus viridans*
*Streptococcus zooepidemicus*
Uliginosibacterium

*Uliginosibacterium gangwonense*
Ulvibacter

*Ulvibacter litoralis*
Umezawaea

*Umezawaea tangerina*
Undibacterium

*Undibacterium pigrum*
Ureaplasma

*Ureaplasma urealyticum*
Ureibacillus

*Ureibacillus composti*
*Ureibacillus suwonensis*
*Ureibacillus terrenus*
*Ureibacillus thermophilus*
*Ureibacillus thermosphaericus*
Vagococcus

*Vagococcus carniphilus*
*Vagococcus elongatus*
*Vagococcus fessus*
*Vagococcus fluvialis*
*Vagococcus lutrae*
*Vagococcus salmoninarum*
Variovorax

*Variovorax boronicumulans*
*Variovorax dokdonensis*
*Variovorax paradoxus*
*Variovorax soli*
Veillonella

*Veillonella atypica*
*Veillonella caviae*
*Veillonella criceti*
*Veillonella dispar*
*Veillonella montpellierensis*
*Veillonella parvula*
*Veillonella ratti*
*Veillonella rodentium*

TABLE 7-continued

Example Bacteria

Venenivibrio

*Venenivibrio stagnispumantis*
Verminephrobacter

*Verminephrobacter eiseniae*
Verrucomicrobium

*Verrucomicrobium spinosum*
Vibrio

*Vibrio aerogenes*
*Vibrio aestuarianus*
*Vibrio albensis*
*Vibrio alginolyticus*
*Vibrio campbellii*
*Vibrio cholerae*
*Vibrio cincinnatiensis*
*Vibrio coralliilyticus*
*Vibrio cyclitrophicus*
*Vibrio diazotrophicus*
*Vibrio fluvialis*
*Vibrio furnissii*
*Vibrio gazogenes*
*Vibrio halioticoli*
*Vibrio harveyi*
*Vibrio ichthyoenteri*
*Vibrio mediterranei*
*Vibrio metschnikovii*
*Vibrio mytili*
*Vibrio natriegens*
*Vibrio navarrensis*
*Vibrio nereis*
*Vibrio nigripulchritudo*
*Vibrio ordalii*
*Vibrio orientalis*
*Vibrio parahaemolyticus*
*Vibrio pectenicida*
*Vibrio penaeicida*
*Vibrio proteolyticus*
*Vibrio shilonii*
*Vibrio splendidus*
*Vibrio tubiashii*
*Vibrio vulnificus*
Virgibacillus

*Virgibacillus halodenitrificans*
*Virgibacillus pantothenticus*
Weissella

*Weissella cibaria*
*Weissella confusa*
*Weissella halotolerans*
*Weissella hellenica*
*Weissella kandleri*
*Weissella koreensis*
*Weissella minor*
*Weissella paramesenteroides*
*Weissella soli*
*Weissella thailandensis*
*Weissella viridescens*
Williamsia

*Williamsia marianensis*
*Williamsia maris*
*Williamsia serinedens*
Winogradskyella

*Winogradskyella thalassocola*
Wolbachia

*Wolbachia persica*

TABLE 7-continued

Example Bacteria

Wolinella

*Wolinella succinogenes*
Xanthobacter

*Xanthobacter agilis*
*Xanthobacter aminoxidans*
*Xanthobacter autotrophicus*
*Xanthobacter flavus*
*Xanthobacter tagetidis*
*Xanthobacter viscosus*
Xanthomonas

*Xanthomonas albilineans*
*Xanthomonas alfalfae*
*Xanthomonas arboricola*
*Xanthomonas axonopodis*
*Xanthomonas campestris*
*Xanthomonas citri*
*Xanthomonas codiaei*
*Xanthomonas cucurbitae*
*Xanthomonas euvesicatoria*
*Xanthomonas fragariae*
*Xanthomonas fuscans*
*Xanthomonas gardneri*
*Xanthomonas hortorum*
*Xanthomonas hyacinthi*
*Xanthomonas perforans*
*Xanthomonas phaseoli*
*Xanthomonas pisi*
*Xanthomonas populi*
*Xanthomonas theicola*
*Xanthomonas translucens*
Xenophilus

*Xenophilus azovorans*
Xenorhabdus

*Xenorhabdus beddingii*
*Xenorhabdus bovienii*
*Xenorhabdus cabanillasii*
*Xenorhabdus doucetiae*
*Xenorhabdus griffiniae*
*Xenorhabdus hominickii*
*Xenorhabdus koppenhoeferi*
*Xenorhabdus nematophila*
*Xenorhabdus poinarii*
Xylanibacter

*Xylanibacter oryzae*
Xylanibacterium

*Xylanibacterium ulmi*
Yangia

*Yangia pacifica*
Yaniella

*Yaniella flava*
*Yaniella halotolerans*
Yeosuana

*Yeosuana aromativorans*
Yersinia

*Yersinia aldovae*
*Yersinia bercovieri*
*Yersinia enterocolitica*
*Yersinia entomophaga*
*Yersinia frederiksenii*
*Yersinia intermedia*
*Yersinia kristensenii*
*Yersinia mollaretii*
*Yersinia philomiragia*
*Yersinia pestis*
*Yersinia pseudotuberculosis*
*Yersinia rohdei*
*Yersinia ruckeri*
Yokenella

*Yokenella regensburgei*
Yonghaparkia

*Yonghaparkia alkaliphila*
Zavarzinia

*Zavarzinia compransoris*
Zobellella

*Zobellella denitrificans*
*Zobellella taiwanensis*
Zobellia

*Zobellia galactanivorans*
*Zobellia uliginosa*
Zoogloea

*Zoogloea ramigera*
*Zoogloea resiniphila*
Zooshikella

*Zooshikella ganghwensis*
Zunongwangia

*Zunongwangia profunda*
Zymobacter

*Zymobacter palmae*
Zymomonas

*Zymomonas mobilis*
Zymophilus

*Zymophilus paucivorans*
*Zymophilus raffinosivorans*
Zeaxanthinibacter

*Zeaxanthinibacter enoshimensis*
Zhihengliuella

*Zhihengliuella halotolerans*

REFERENCES

1. Ainsworth S Sadovskaya I Vinogradov E et al Differences in lactococcal cell wall polysaccharide structure are major determining factors in bacteriophage sensitivity mBio 2014 5 e0088014
2. Bae H Cho Y Complete genome sequence of *Pseudomonas aeruginosa* podophage MPK7, which requires type IV pili for infection Genome Announc 2013 1 1
3. Baptista C Santos M A Sáo-José C Phage SPP1 reversible adsorption to *Bacillus subtilis* cell wall teichoic acids accelerates virus recognition of membrane receptor YueB J Bacteriol 2008 190 498996
4. Bebeacua C Tremblay D Farenc C et al Structure, adsorption to host, and infection mechanism of virulent Lactococcal phage p2 J Virol 2013 87 1230212
5. Beveridge T J Graham L L Surface layers of bacteria Microbiol Rev 1991 55 684705

6. Black P N The fadL gene product of *Escherichia coli* is an outer membrane protein required for uptake of long-chain fatty acids and involved in sensitivity to bacteriophage T2 J Bacteriol 1988 170 28504
7. Bradbeer C Woodrow M L Khalifah L I Transport of vitamin B12 in *Escherichia coli*: common receptor system for vitamin B12 and bacteriophage BF23 on the outer membrane of the cell envelope J Bacteriol 1976 125 10329
8. Braun V Schaller K Wolff H A common receptor protein for phage T5 and colicin M in the outer membrane of *Escherichia coli* B Biochim Biophys Acta 1973 323 8797
9. Braun V Wolff H Characterization of the receptor protein for phage T5 and colicin M in the outer membrane of *E. coli* B FEBS Lett 1973 34 7780
10. Budzik J M Rosche W A Rietsch A et al Isolation and characterization of a generalized transducing phage for *Pseudomonas aeruginosa* strains PAO1 and PA14 J Bacteriol 2004 186 32703
11. Caro L G Schnos M The attachment of the male-specific bacteriophage F1 to sensitive strains of *Escherichia coli* P Natl Acad Sci USA 1966 56 12632
12. Chapot-Chartier M-P Vinogradov E Sadovskaya I et al Cell surface of *Lactococcus lactis* is covered by a protective polysaccharide pellicle J Biol Chem 2010 285 1046471
13. Chatterjee S Rothenberg E Interaction of bacteriophage λ with its *E. coli* receptor, LamB Viruses 2012 4 316278
14. Chaturongakul S Ounjai P Phage-host interplay: examples from tailed phages and Gram-negative bacterial pathogens Front Microbiol 2014 5 18
15. Choi Y Shin H Le J-H et al Identification and characterization of a novel flagellum-dependent *Salmonella*-infecting bacteriophage, iEPS5 Appl Environ Microb 2013 79 482937
16. Click E M Webster R E The TolQRA proteins are required for membrane insertion of the major capsid protein of the filamentous phage f1 during infection J Bacteriol 1998 180 17238
17. Clokie M R J Millard A D Letarov A V et al Phages in nature Bacteriophage 20111 3145
18. Cvirkaite-Krupovic V Entry of the membrane-containing bacteriophages into their hosts Ph.D. Dissertation 2010 University of Helsinki
19. Datta D B Arden B Henning U Major proteins of the *Escherichia coli* outer cell envelope membrane as bacteriophage receptors J Bacteriol 1977 131 8219
20. Daugelavicius R Bamford J K H Grahn A M et al The IncP plasmid-encoded cell envelope-associated DNA transfer complex increases cell permeability J Bacteriol 1997 179 5195202
21. Daugelavicius R Cvirkaite V Gaidelyte A et al Penetration of enveloped double-stranded RNA bacteriophages φ13 and φ6 into *Pseudomonas syringae* cells J Virol 2005 79 501726
22. Davison S Couture-Tosi E Candela T et al Identification of the *Bacillus anthracis* γphage receptor J Bacteriol 2005 187 67429
23. Douglas J L Wolin M J Cell wall polymers and phage lysis of *Lactobacillus plantarum* Biochemistry 1971 10 15515
24. Duckworth D H History and basic properties of bacterial viruses Goyal S M Gerba C P Bitton G Phage Ecology New York John Wiley & Sons 1987 143
25. Edwards P Smit J A transducing bacteriophage for *Caulobacter crescentus* uses the paracrystalline surface layer protein as a receptor J Bacteriol 1991 173 556872
26. Fehmel F Feige U Niemann H et al *Escherichia coli* capsule bacteriophages VII. Bacteriophage 29-host capsular polysaccharide interactions J Virol 1975 16 591601
27. Feige U Stirm S On the structure of the *Escherichia coli* C cell wall lipopolysaccharide core and on its φX174 receptor region Biochem Bioph Res Co 1976 71 56673
28. Filippov A A Sergueev K V He Y et al Bacteriophage-resistant mutants in *Yersinia pestis*: identification of phage receptors and attenuation for mice PLoS One 2011 6 e25486
29. Frost L Conjugative pili and pilus-specific phages Clewell D B Bacterial Conjugation New York Plenum Press 1993 189222
30. Gaidelyte A Cvirkaite-Krupovic V Daugelavicius R et al The entry mechanism of membrane-containing phage Bam35 infecting *Bacillus thuringiensis* J Bacteriol 2006 188 592534
31. Garbe J Bunk B Rohde M et al Sequencing and characterization of *Pseudomonas aeruginosa* phage JG004 BMC Microbiol 2011 11 102
32. Garen A Puck T T The first two steps of the invasion of host cells by bacterial viruses J Exp Med 1951 94 17789
33. German G J Misra R The TolC protein of *Escherichia coli* serves as a cell-surface receptor for the newly characterized TLS bacteriophage J Mol Biol 2001 308 57985
34. Ghannad M S Mohammadi A Bacteriophage: time to re-evaluate the potential of phage therapy as a promising agent to control multidrug-resistant bacteria Iran J Basic Med Sci 2012 15 693701
35. Goldberg E Grinius L Letellier L Recognition, attachment and injection Karam J D Molecular Biology of Bacteriophage T4 Washington American Society for Microbiology 1994 34756
36. Guerrero-Ferreira R C Viollier P H Ely B et al Alternative mechanism for bacteriophage adsorption to the motile bacterium *Caulobacter crescentus* P Natl Acad Sci USA 2011 108 99638
37. Hancock R E W Braun V Nature of the energy requirement for the irreversible adsorption of bacteriophages T1 and φ80 to *Escherichia coli* J Bacteriol 1976 125 40915
38. Hantke K Major outer membrane proteins of *E. coli* K12 serve as receptors for the phages T2 (Protein Ia) and 434 (Protein Ib) Mol Gen Genet 1978 164 1315
39. Hantke K Braun V Membrane receptor dependent iron transport in *Escherichia coli* FEBS Lett 1975 49 3015
40. Hantke K Braun V Functional interaction of the tonA/tonB receptor system in *Escherichia coli* J Bacteriol 1978 135 1907
41. Hashemolhosseini S Holmes Z Mutschler B et al Alterations of receptor specificities of coliphages of the T2 family J Mol Biol 1994 240 10510
42. Heller K J Identification of the phage gene for host receptor specificity by analyzing hybrid phages of T5 and BF23 Virology 1984 139 1121
43. Heller K J Molecular interaction between bacteriophage and the gram-negative cell envelope Arch Microbiol 1992 158 23548
44. Heller K Braun V Polymannose O-antigens of *Escherichia coli*, the binding sites for the reversible adsorption of bacteriophage T5+ via the L-shaped tail fibers J Virol 1982 41 2227
45. Henning U Hashemolhosseini S Receptor recognition by T-even-type coliphages Karam J D Molecular Biology of Bacteriophage T4 Washington American Society for Microbiology 1994 2918
46. Heo Y-J Chung I-Y Choi K B et al Genome sequence comparison and superinfection between two related

*Pseudomonas aeruginosa* phages, D3112 and MP22 Microbiology 2007 153 288595
47. Ho T D Slauch J M OmpC is the receptor for Gifsy-1 and Gifsy-2 bacteriophages of *Salmonella* J Bacteriol 2001 183 14958
48. Hyman P Abedon S T Bacteriophage host range and bacterial resistance Laskin A I Sariaslani S Gadd G M Advances in Applied Microbiology Vol. 70 San Diego Elsevier Inc. 2010 21748
49. Iwashita S Kanegasaki S Smooth specific phage adsorption: endorhamnosidase activity of tail parts of P22 Biochem Bioph Res Co 1973 55 4039
50. Iwashita S Kanegasaki S Deacetylation reaction catalyzed by *Salmonella* phage c341 and its baseplate parts J Biol Chem 1976 251 53615
51. Jarrell K F Kropinski A M B Isolation and characterization of a bacteriophage specific for the lipopolysaccharide of rough derivatives of *Pseudomonas aeruginosa* strain PAO J Virol 1981 38 52938
52. Kaneko J Narita-Yamada S Wakabayashi Y et al Identification of ORF636 in phage φSLT carrying pantonvalentine leukocidin genes, acting as an adhesion protein for a poly(glycerophosphate) chain of lipoteichoic acid on the cell surface of *Staphylococcus aureus* J Bacteriol 2009 191 467480
53. Killmann H Braun M Herrmann C et al FhuA barrel-cork hybrids are active transporters and receptors J Bacteriol 2001 183 347687
54. Kim M Ryu S Spontaneous and transient defence against bacteriophage by phase-variable glucosylation of O-antigen in *Salmonella enterica* serovar *Typhimurium* Mol Microbiol 2012 86 41125
55. Kivela H M Madonna S Krupovic M et al Genetics for *Pseudoalteromonas* provides tools to manipulate marine bacterial virus PM2 J Bacteriol 2008 190 1298307
56. Kokjohn T A Miller R V Gene transfer in the environment: transduction Fry J C Day M J Release of Genetically Engineered and Other Micro-Organisms Cambridge Cambridge University Press 1992 5481
57. Labrie S J Samson J E Moineau S Bacteriophage resistance mechanisms Nat Rev Microbiol 2010 8 31727
58. Letellier L Boulanger P Plançon L et al Main features on tailed phage, host recognition and DNA uptake Front Biosci 2004 9 122839
59. Lindberg A A Bacteriophage receptors Annu Rev Microbiol 1973 27 20541
60. Lindberg A A Bacterial surface carbohydrates and bacteriophage adsorption Sutherland I Surface Carbohydrates of the Prokaryotic Cell London Academic Press 1977 289356
61. Lindberg A A Wollin R Gemski P et al Interaction between bacteriophage Sf6 and *Shigella flexneri* J Virol 1978 27 3844
62. Loeb T Isolation of a bacteriophage specific for the F+ and Hfr mating types of *Escherichia coli* K-12 Science 1960 131 9323
63. Madigan M T Martinko J M Stahl D A et al Brock Biology of Microorganisms San Francisco Benjamin Cummings 2012
64. Mahony J van Sinderen D Gram-positive phage-host interactions Front Microbiol 2015 6 12
65. Manning P A Reeves P Outer membrane of *Escherichia coli* K-12: differentiation of proteins 3A and 3B on acrylamide gels and further characterization of con (tolG) mutants J Bacteriol 1976 127 10709
66. Manning P A Reeves P Outer membrane proteins of *Escherichia coli* K-12: isolation of a common receptor protein for bacteriophage T6 and colicin K Mol Gen Genet 1978 158 27986
67. Marti R Zurfluh K Hagens S et al Long tail fibres of the novel broad-host-range T-even bacteriophage S16 specifically recognize *Salmonella* OmpC Mol Microbiol 2013 87 81834
68. Meadow P M Wells P L Receptor sites for R-type pyocins and bacteriophage E79 in the core part of the lipopolysaccharide of *Pseudomonas aeruginosa* PACi J Gen Microbiol 1978 108 33943
69. Mindich L Qiao X Qiao J et al Isolation of additional bacteriophages with genomes of segmented double-stranded RNA J Bacteriol 1999 181 45058
70. Moineau S Lévesque C Control of bacteriophages in industrial fermentations Kutter E Sulakvelidze A Bacteriophages: Biology and Applications Boca Raton CRC Press 2005
71. Molineux I J No syringes please, ejection of phage T7 DNA from the virion is enzyme driven Mol Microbiol 2001 40 18
72. Molineux U Panja D Popping the cork: mechanism of phage genome ejection Nat Rev Microbiol 2013 11 194204
73. Monteville M R Ardestani B Geller B L Lactococcal bacteriophages require a host cell wall carbohydrate and a plasma membrane protein for adsorption and ejection of DNA Appl Environ Microb 1994 60 320411
74. Morona R Henning U Host range mutants of bacteriophage O×2 can use two different outer membrane proteins of *Escherichia coli* K-12 as receptors J Bacteriol 1984 159 57982
75. Morona R Henning U New locus (ttr) in *Escherichia coli* K-12 affecting sensitivity to bacteriophage T2 and growth on oleate as the sole carbon source J Bacteriol 1986 168 53440
76. Munsch-Alatossava P Alatossava T The extracellular phage-host interactions involved in the bacteriophage LL-H infection of *Lactobacillus delbrueckii* ssp. *lactis* ATCC 15808 Front Microbiol 2013 4 15
77. Mutoh N Furukawa H Mizushima S Role of lipopolysaccharide and outer membrane protein of *Escherichia coli* K-12 in the receptor activity for bacteriophage T4 J Bacteriol 1978 136 6939
78. Pickard D Toribio A L Petty N K et al A conserved acetyl esterase domain targets diverse bacteriophage to the Vi capsular receptor of *Salmonella enterica* serovar *Typhi* J Bacteriol 2010 192 574654
79. Picken R N Beacham I R Bacteriophage-resistant mutants of *Escherichia coli* K12. Location of receptors within the lipopolysaccharide J Gen Microbiol 1977 102 30518
80. Pommerville J C Alcamo's Fundamentals of Microbiology Sudbury Jones & Barlett Publishers 2010
81. Prehm P Jann B Jann K et al On a bacteriophage T3 and T4 receptor region within the cell wall lipopolysaccharide of *Escherichia coli* B J Mol Biol 1976 101 27781
82. Rakhuba D V Kolomiets E I Szwajcer Dey E et al Bacteriophage receptors, mechanisms of phage adsorption and penetration into host cell Pol J Microbiol 2010 59 14555
83. Randall-Hazelbauer L Schwartz M Isolation of the bacteriophage lambda receptor from *Escherichia coli* J Bacteriol 1973 116 143646

84. Reske K Wallenfels B Jann K Enzymatic degradation of O-antigenic lipopolysaccharides by coliphage Ω8 Eur J Biochem 1973 36 16771
85. Riede I Receptor specificity of the short tail fibres (gp12) of T-even type *Escherichia coli* phages Mol Gen Genet 1987 206 1105
86. Roa M Interaction of bacteriophage K10 with its receptor, the lamB protein of *Escherichia coli* J Bacteriol 1979 140 6806
87. Russel M Whirlow H Sun T-P et al Low-frequency infection of F-bacteria by transducing particles of filamentous bacteriophages J Bacteriol 1988 170 53126
88. Sandulache R Prehm P Expert D et al The cell wall receptor for bacteriophage Mu G(−) in *Erwinia* and *Escherichia coli* C FEMS Microbiol Lett 1985 28 30710
89. Sandulache R Prehm P Kamp D Cell wall receptor for bacteriophage Mu G(+) J Bacteriol 1984 160 299303
90. Sio-José C Baptista C Santos M A *Bacillus subtilis* operon encoding a membrane receptor for bacteriophage SPP1 J Bacteriol 2004 186 833746
91. Schade S Z Adler J Ris H How bacteriophage λ attacks motile bacteria J Virol 1967 1 599609
92. Schwartz M Interaction of phages with their receptor proteins Randall L L Philipson L Virus Receptors-Part 1 London Chapman & Hall 1980 5994
93. Shaw D R D Chatterjee A N O-Acetyl groups as a component of the bacteriophage receptor on *Staphylococcus aureus* cell walls J Bacteriol 1971 108 5845
94. Shin H Lee J-H Kim H et al Receptor diversity and host interaction of bacteriophages infecting *Salmonella enterica* Serovar *Typhimurium* PLoS One 2012 7 e43392
95. Skurray R A Hancock R E W Reeves P Con-mutants: Class of mutants in *Escherichia coli* K-12 lacking a major cell wall protein and defective in conjugation and adsorption of a bacteriophage J Bacteriol 1974 119 72635
96. Stirm S Bessler W Fehmel F et al Bacteriophage particles with endo-glycosidase activity J Virol 1971 8 3436
97. Sukupolvi S Role of lipopolysaccharide in the receptor function for bacteriophage O×2 FEMS Microbiol Lett 1984 21 837
98. Takeda K Uetake H Receptor splitting enzyme of *Salmonella* phage ε34 Annu Rep Inst Virus Res 1973 16 256
99. Thurow H Niemann H Stirm S Bacteriophage-borne enzymes in carbohydrate chemistry: Part 1-on the glycanase activity associated with particles of *Klebsiella* bacteriophage no 11 Carbohyd Res 1975 41 25771
100. Tortora G J Funke B R Case CLMicrobiology: An Introduction San Francisco Benjamin Cummings 2007
101. Van Alphen L Havekes L Lugtenberg B Major outer membrane protein d of *Escherichia coli* K12. Purification and in vitro activity of bacteriophage k3 and f-pilus mediated conjugation FEBS Lett 1977 75 28590
102. Verhoef C de Graaff P J Lugtenberg E J J Mapping of a gene for a major outer membrane protein of Escberichia *coli* K12 with the aid of a newly isolated bacteriophage Mol Gen Genet 1977 150 1035
103. Vidaver A K Koski R K Van Etten J L Bacteriophage 6: a lipid-containing virus of *Pseudomonas phaseolicola* J Virol 1973 11 799805
104. Vinga I Baptista C Auzat I et al Role of bacteriophage SPP1 tail spike protein gp21 on host cell receptor binding and trigger of phage DNA ejection Mol Microbiol 2012 83 289303
105. Vinga I Sáo-José C Tavares P et al Bacteriophage entry in the host cell Wegrzyn G Modern Bacteriophage Biology and Biotechnology Trivandrum: Research Signpost 2006 165205
106. Wayne R Neilands J B Evidence for common binding sites for ferrichrome compounds and bacteriophage φ80 in the cell envelope of *Escherichia coli* J Bacteriol 1975 121 497503
107. Wendlinger G Loessner M J Scherer S Bacteriophage receptors on *Listeria monocytogenes* cells are the N-acetylglucosamine and rhamnose substituents of teichoic acids or the peptidoglycan itself Microbiology 1996 142 98592
108. Willey J M Sherwood L M Woolverton C J Prescott, Harley, and Klein's Microbiology New York McGraw-Hill 2008
109. Wright A McConnell M Kanegasaki S Lipopolysaccharide as a bacteriophage receptor Randall L L Philipson L Virus Receptors-Part 1 London Chapman & Hall 1980 2757
110. Xia G Corrigan R M Winstel V et al Wall teichoic acid-dependent adsorption of Staphylococcal siphovirus and myovirus J Bacteriol 2011 193 40069
111. Xiang Y Leiman P G Li L et al Crystallographic insights into the autocatalytic assembly mechanism of a bacteriophage tail spike Mol Cell 2009 34 37586
112. Yokota S-I Hayashi T Matsumoto H Identification of the lipopolysaccharide core region as the receptor site for a cytotoxin-converting phage, φCTX, of *Pseudomonas aeruginosa* J Bacteriol 1994 176 52629

The invention claimed is:
1. A method of producing a population of phages, wherein the phages are of a first type capable of infecting host cells of a first bacterial species or strain by binding a cell-surface receptor comprised by bacteria of the first species or strain, the method comprising:
(a) providing a population of second bacterial cells comprising the receptor on the surface of the second cells, wherein the second cells are of a second species or strain, wherein the second species or strain is different from the first species or strain;
(b) infecting the second cells with the phages of the first type; and
(c) propagating the phages in the second cells, thereby producing the population of phages,
wherein the phages comprise a nucleotide sequence encoding crRNAs that are operable with a Cas in bacteria of the host cell strain or species to form an active CRISPR/Cas system that is capable of targeting one or more protospacer nucleotide sequences, wherein each target sequence is comprised by the genome of the host cells, whereby the crRNAs guide the Cas in host cells to modify the target sequence, thereby killing host cells or reducing host cell population growth; and
wherein the genome of each second bacterial cell does not comprise the target sequence.
2. A method of producing a population of phages, wherein the phages are of a first type capable of infecting host cells of a first bacterial species or strain by binding a cell-surface receptor comprised by bacteria of the first species or strain, the method comprising
(a) providing a population of second bacterial cells comprising the receptor on the surface of the second cells, wherein the second cells are of a second species or strain, wherein the second species or strain is different from the first species or strain;

(b) infecting the second cells with the phages of the first type; and
(c) propagating the phages in the second cells, thereby producing the population of phages;
wherein the phages comprise a nucleotide sequence encoding crRNAs that are operable with a Cas in bacteria of the host cell strain or species to form an active CRISPR/Cas system that is capable of targeting one or more protospacer nucleotide sequences, wherein each target sequence is comprised by the genome of the host cells, whereby the crRNAs guide the Cas in host cells to modify the target sequence, thereby killing host cells or reducing host cell population growth; and
wherein when infected by the phage, the second cells do not comprise the active CRISPR/Cas system.

3. The method of claim 1, wherein
(a) a Cas of the second cells is not operable with the crRNAs;
(b) a tracrRNA of the second cells is not operable with the crRNAs; and/or
(c) the second cells are not operable to produce the crRNAs from the crRNA-encoding nucleotide sequence.

4. A method of producing a population of phages, wherein the phages are of a first type capable of infecting host cells of a first bacterial species or strain by binding a cell-surface receptor comprised by bacteria of the first species or strain, the method comprising
(a) providing a population of second bacterial cells comprising the receptor on the surface of the second cells, wherein the second cells are of a second species or strain, wherein the second species or strain is different from the first species or strain;
(b) infecting the second cells with the phages of the first type; and
(c) propagating the phages in the second cells, thereby producing the population of phages;
wherein the phages comprise a nucleotide sequence encoding crRNAs that are operable with a Cas in bacteria of the host cell strain or species to form an active CRISPR/Cas system that is capable of targeting one or more protospacer nucleotide sequences, wherein each target sequence is comprised by the genome of the host cells, whereby the crRNAs guide the Cas in host cells to modify the target sequence, thereby killing host cells or reducing host cell population growth; and
wherein the crRNAs comprise repeat sequences that are not operable with a Cas of the second cells.

5. The method of claim 1, wherein the nucleotide sequence is operably connected with a promoter for transcription of crRNAs in bacteria of the host species or strain, but not in the second species or strain.

6. The method of claim 1, wherein
the host cells and the second cells are different strains of the same species.

7. The method of claim 1, wherein bacteria of the host species or strain comprise an anti-phage toxin or mechanism for reducing the propagation of phages of the first type that infect host bacteria, wherein the second bacteria do not comprise the toxin or mechanism.

8. The method of claim 1, wherein bacteria of the host species or strain comprise a CRISPR/Cas system that is active for reducing the propagation of phages of the first type that infect host bacteria, wherein the second bacteria do not comprise the CRISPR/Cas system.

9. A method of producing a population of phages, wherein the phages are of a first type capable of infecting host cells of a first bacterial species or strain by binding a cell-surface receptor comprised by bacteria of the first species or strain, the method comprising
(a) providing a population of second bacterial cells comprising the receptor on the surface of the second cells, wherein the second cells are of a second species or strain, wherein the second species or strain is different from the first species or strain;
(b) infecting the second cells with the phages of the first type; and
(c) propagating the phages in the second cells, thereby producing the population of phages;
wherein the second bacterial cells are engineered to produce the receptor, wherein wild-type bacteria of the second species or strain do not produce the receptor.

10. The method of claim 1, wherein the second cells are *Escherichia coli* cells.

11. The method of claim 1, wherein the host cells and the second cells are of the same species.

12. The method of claim 11, wherein the strain of host cells is a human pathogenic strain and the second cell strain is not a human pathogenic strain.

13. The method of claim 1, wherein the receptor is selected from the group consisting of lipopolysaccharides, teichoic acids, proteins and flagella.

14. The method of claim 1, wherein the receptor comprises an O-antigen of the host cells.

15. The method of claim 1, wherein the phages are operable to express an endolysin or holin in the second cells.

16. A method of producing a population of phages, wherein the phages are of a first type capable of infecting host cells of a first bacterial species or strain by binding a cell-surface receptor comprised by bacteria of the first species or strain, the method comprising
(a) providing a population of second bacterial cells comprising the receptor on the surface of the second cells, wherein the second cells are of a second species or strain, wherein the second species or strain is different from the first species or strain;
(b) infecting the second cells with phages of the first type; and
(c) propagating the phages in the second cells, thereby producing the population of phages; and
wherein the receptor comprises a teichoic acid moiety that is the product of the action of one or more enzymes in the second cell, wherein the genome of the second cell comprises one or more expressible nucleotide sequences encoding the one or more enzymes, wherein wild-type cells of the second species or strain do not comprise the expressible nucleotide sequences.

17. The method of claim 16, wherein the enzymes are selected from the group consisting of TarO, TarA, TarB, TarF, TarK, and TarL.

18. The method of claim 2, wherein the second cells are *Escherichia coli* cells.

19. The method of claim 2, wherein the host cells and the second cells are of the same species.

20. The method of claim 4, wherein the second cells are *Escherichia coli* cells.

21. The method of claim 4, wherein the host cells and the second cells are of the same species.

* * * * *